US005702917A

United States Patent [19]
Kilgannon et al.

[11] Patent Number: 5,702,917
[45] Date of Patent: Dec. 30, 1997

[54] POLYNUCLEOTIDES ENCODING HUMAN ICAM-4

[75] Inventors: Patrick D. Kilgannon, Bothell; W. Michael Gallatin, Mercer Island, both of Wash.

[73] Assignee: ICOS Corporation, Bothell, Wash.

[21] Appl. No.: 481,130

[22] Filed: Jun. 7, 1995

Related U.S. Application Data

[63] Continuation-in-part of Ser. No. 245,295, May 18, 1994, which is a continuation-in-part of Ser. No. 102,852, Aug. 5, 1993, abandoned, which is a continuation-in-part of Ser. No. 9,266, Jan. 22, 1993, abandoned, which is a continuation-in-part of Ser. No. 894,061, Jun. 5, 1992, abandoned, which is a continuation-in-part of Ser. No. 889,724, May 26, 1992, abandoned, which is a continuation-in-part of Ser. No. 827,689, Jan. 27, 1992, abandoned.

[51] Int. Cl.$^6$ ................................................. C12N 15/12
[52] U.S. Cl. ................. 435/69.1; 435/252.3; 435/320.1; 435/325; 536/23.5
[58] Field of Search ........................... 56/23.5; 435/69.1, 435/240.2, 252.3, 320.1, 325

[56] References Cited

FOREIGN PATENT DOCUMENTS

| | | |
|---|---|---|
| 0289949 | 11/1988 | European Pat. Off. . |
| 468257 A | 1/1992 | European Pat. Off. . |
| WO 89/02922 | 4/1989 | WIPO . |
| WO 90/13300 | 11/1990 | WIPO . |
| WO 91/10683 | 7/1991 | WIPO . |
| WO 91/16928 | 11/1991 | WIPO . |
| WO 92/04034 | 3/1992 | WIPO . |
| WO 93/14776 | 8/1993 | WIPO . |

OTHER PUBLICATIONS

Ashkenazi, et al., *Proc.Natl.Acad.Sci.* (*USA*) 88:10535–10539 (1991) "Protection against endotoxic shock by tumor necrosis factor receptor immunoadhesin".
Capecchi, *Science* 244:1288–1292 (1989) "Altering the genome by homologous recombination."
Capon, et al., *Nature* 337:525–531 (1989) "Designing CD4 immunoadhesins for AIDS therapy."
de Fourgerolles, et al., *J.Exp.Med.* 175:185–190 (1992) "Intercellular adhesion molecule 3, a third adhesion counter–receptor for lymphocyte function associated molecule 1 on resting lymphocytes."
Dustin, et al., *J. Immunol.* 137:245–254 (1986) "Induction by IL–1 and interferon–γ: tissue distribution, biochemistry, and function of a natural adherence molecule (ICAM–1)".
Edwards, *Curr.Opin.Ther.Pat.* 1:1627–1630 (1991) "Cell adhesion molecules as a target for therapy."
Frohman, *PCR Protocols*, Innis (ed), pp.28–38 (1990) "RACE: rapid amplification of cDNA ends."
Imamura, et al., *Neurosci.Letts.* 119:118–121 (1990) "Variations by layers and developmental changes in expression of telencephalin."
Kita, et al., *Biochem.Biophys.Acta* 1131:108–110 (1992) "Sequence and expression of rt ICAM–1".
Mori, et al., *Proc.Natl.Acad.Sci.* (*USA*) 84:3921–3925 (1987) "Telencephalon–specific antigen identified by monoclonal antibody".
Newman, et al., *Science* 247:1219–1222 (1990) "PECAM–1 (CD31) cloning and relation to adhesion molecules of the immunoglobulin gene superfamily."
Oka, et al., *Neuroscience* 35:93–103 (1990) "Mammalian telencephalic neurons express a segment–specific membrane glycoprotein, telencephalin."
Sonderegger et al., *J.Cell.Biol.* 119:1387–1394 (1992) "Regulation of axonal growth in the vertebrate nervous system by interactions between glycoproteins belonging to two subgroups of the immunoglobulin superfamily."
Springer, *Nature* 346:425–434 (1990) "Adhesion receptors of the immune system."
Stauton, et al., *Nature* 339:61–64 (1989) "Functional cloning of ICAM–2, a cell adhesion ligand for LFA–1 homologous to ICAM–1."
Vonderheide, et al., *J.Cell.Biol* 125:215–222 (1994) "Residues within a conserved amino acid motif of domains 1 and 4 of VCAM–1 are required for binding to VLA–4".
Xu, et al., *J.Immunol.* 149:2560–2565 (1992) "Isolation, characterization, and expression of mouse ICAM–2 complementary and genomic DNA".
Yoshihara, et al., *Neurosci.Res.* 10:83–105 (1991) "Immunoglobulin superfamily molecules in the nervous system."
Yoshihiro, et al., *Neuron* 12:543–553 (1994) "An ICAM–related neuronal glycoprotein, telencephalin, with brain segment–specific expression".
Yoshihiro, et al., *Neuroscience* Supp. 18, p.S83 (1994) "Primary structure of telencephalon–specific neuronal adhesion molecule telencephalin."
Yoshihiro, et al., *Soc.Neurosci.Abstr.* 19(1–3) p.646 (1993) "Telencephanlin, a brian segment–specific dendritic glycoprotein, is a novel member of immunoglobulin superfamily."
Voraberger et al. (1991) J. Immunol. 147.2777–2786.
Genbank—EMBL: Locus—MMU06483, Accession—U06483 Definition—Mus Musculus BALB/C Telencephalin Precursor mRNA, 1994.
Genbank—EMBL: Locus—RABTELCEPH Accession—L13199 Definition—Rabbit Telencephalin mRNA, 1994.

*Primary Examiner*—Stephen Walsh
*Assistant Examiner*—Karen E. Brown
*Attorney, Agent, or Firm*—Marshall, O'Toole, Gerstein, Murray & Borun

[57] ABSTRACT

DNA sequences encoding a novel intercellular adhesion molecule polypeptide (designated "ICAM-4") and variants thereof are disclosed along with methods and materials for production of the same by recombinant procedures.

10 Claims, No Drawings

5,702,917

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:

-continued ( A ) LENGTH: 2988 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 61..2814

( x i ) SEQUENCE DESCRIPTION: SEQ ID NO:1:

```
AATTCGATCA CTCGCGCTCC CCTCGCCTTC TGCGCTCTCC CCTCCCTGGC AGCGGCGGCA            60

ATG CCG GGG CCT TCA CCA GGG CTG CGC CGA ACG CTC CTC GGC CTC TGG            108
Met Pro Gly Pro Ser Pro Gly Leu Arg Arg Thr Leu Leu Gly Leu Trp
 1               5                  10                  15

GCT GCC CTG GGC CTG GGG ATC CTA GGC ATC TCA GCG GTC GCG CTA GAA            156
Ala Ala Leu Gly Leu Gly Ile Leu Gly Ile Ser Ala Val Ala Leu Glu
             20                  25                  30

CCT TTC TGG GCG GAC CTT CAG CCC CGC GTG GCG CTC GTG GAG CGC GGG            204
Pro Phe Trp Ala Asp Leu Gln Pro Arg Val Ala Leu Val Glu Arg Gly
         35                  40                  45

GGC TCG CTG TGG CTC AAC TGC AGC ACT AAC TGT CCG AGG CCG GAG CGC            252
Gly Ser Leu Trp Leu Asn Cys Ser Thr Asn Cys Pro Arg Pro Glu Arg
     50                  55                  60

GGT GGC CTG GAG ACC TCG CTA CGC CGA AAC GGG ACC CAG AGG GGT CTG            300
Gly Gly Leu Glu Thr Ser Leu Arg Arg Asn Gly Thr Gln Arg Gly Leu
 65                  70                  75                  80

CGC TGG CTG GCT CGA CAG CTG GTG GAC ATC CGA GAG CCT GAA ACC CAG            348
Arg Trp Leu Ala Arg Gln Leu Val Asp Ile Arg Glu Pro Glu Thr Gln
                 85                  90                  95

CCG GTC TGC TTC TTC CGC TGC GCG CGC CGC ACA CTC CAA GCG CGT GGG            396
Pro Val Cys Phe Phe Arg Cys Ala Arg Arg Thr Leu Gln Ala Arg Gly
            100                 105                 110

CTC ATC CGA ACT TTC CAG CGA CCG GAT CGG GTA GAG CTA GTG CCT CTG            444
Leu Ile Arg Thr Phe Gln Arg Pro Asp Arg Val Glu Leu Val Pro Leu
        115                 120                 125

CCT CCT TGG CAG CCT GTA GGT GAG AAC TTC ACC TTG AGC TGC AGG GTC            492
Pro Pro Trp Gln Pro Val Gly Glu Asn Phe Thr Leu Ser Cys Arg Val
    130                 135                 140

CCG GGG GCA GGA CCC CGA GCG AGC CTC ACA TTG ACC TTG CTG CGA GGC            540
Pro Gly Ala Gly Pro Arg Ala Ser Leu Thr Leu Thr Leu Leu Arg Gly
145                 150                 155                 160

GGC CAG GAG CTG ATT CGC CGA AGT TTC GTA GGC GAG CCA CCC CGA GCT            588
Gly Gln Glu Leu Ile Arg Arg Ser Phe Val Gly Glu Pro Pro Arg Ala
                165                 170                 175

CGG GGT GCG ATG CTC ACC GCC ACG GTC CTG GCG CGC AGA GAG GAT CAC            636
Arg Gly Ala Met Leu Thr Ala Thr Val Leu Ala Arg Arg Glu Asp His
            180                 185                 190

AGG GCC AAT TTC TCA TGC CTC GCG GAG CTT GAC CTG CGG CCA CAC GGC            684
Arg Ala Asn Phe Ser Cys Leu Ala Glu Leu Asp Leu Arg Pro His Gly
        195                 200                 205

TTG GGA CTG TTT GCA AAC AGC TCA GCC CCC AGA CAG CTC CGC ACG TTT            732
Leu Gly Leu Phe Ala Asn Ser Ser Ala Pro Arg Gln Leu Arg Thr Phe
    210                 215                 220

GCC ATG CCT CCA CTT TCC CCG AGC CTT ATT GCC CCA CGA TTC TTA GAA            780
Ala Met Pro Pro Leu Ser Pro Ser Leu Ile Ala Pro Arg Phe Leu Glu
225                 230                 235                 240

GTG GGC TCA GAA AGG CCG GTG ACT TGC ACT TTG GAT GGA CTG TTT CCT            828
Val Gly Ser Glu Arg Pro Val Thr Cys Thr Leu Asp Gly Leu Phe Pro
                245                 250                 255

GCC CCA GAA GCC GGG GTT TAC CTC TCT CTG GGA GAT CAG AGG CTT CAT            876
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ala | Pro | Glu | Ala     | Gly | Val | Tyr | Leu     | Ser | Leu | Gly | Asp | Gln     | Arg | Leu | His |      |
|     |     |     | 260     |     |     |     | 265     |     |     |     |     | 270     |     |     |     |      |
| CCT | AAT | GTG | ACC | CTC | GAC | GGG | GAG | AGC | CTT | GTG | GCC | ACT | GCC | ACA | GCT | 924  |
| Pro | Asn | Val | Thr | Leu | Asp | Gly | Glu | Ser | Leu | Val | Ala | Thr | Ala | Thr | Ala |      |
|     |     | 275 |     |     |     |     | 280 |     |     |     |     | 285 |     |     |     |      |
| ACA | GCA | AGT | GAA | GAA | CAG | GAA | GGC | ACC | AAA | CAG | CTG | ATG | TGC | ATC | GTG | 972  |
| Thr | Ala | Ser | Glu | Glu | Gln | Glu | Gly | Thr | Lys | Gln | Leu | Met | Cys | Ile | Val |      |
|     | 290 |     |     |     |     | 295 |     |     |     |     | 300 |     |     |     |     |      |
| ACC | CTC | GGG | GGC | GAA | AGC | AGG | GAG | ACC | CAG | GAA | AAC | CTG | ACT | GTC | TAC | 1020 |
| Thr | Leu | Gly | Gly | Glu | Ser | Arg | Glu | Thr | Gln | Glu | Asn | Leu | Thr | Val | Tyr |      |
| 305 |     |     |     |     | 310 |     |     |     |     | 315 |     |     |     |     | 320 |      |
| AGC | TTC | CCG | GCT | CCT | CTT | CTG | ACT | TTA | AGT | GAG | CCA | GAA | GCC | CCC | GAG | 1068 |
| Ser | Phe | Pro | Ala | Pro | Leu | Leu | Thr | Leu | Ser | Glu | Pro | Glu | Ala | Pro | Glu |      |
|     |     |     | 325 |     |     |     |     | 330 |     |     |     |     | 335 |     |     |      |
| GGA | AAG | ATG | GTG | ACC | GTA | AGC | TGC | TGG | GCA | GGG | GCC | CGA | GCC | CTT | GTC | 1116 |
| Gly | Lys | Met | Val | Thr | Val | Ser | Cys | Trp | Ala | Gly | Ala | Arg | Ala | Leu | Val |      |
|     |     |     | 340 |     |     |     | 345 |     |     |     |     | 350 |     |     |     |      |
| ACC | TTG | GAG | GGA | ATT | CCA | GCT | GCG | GTC | CCT | GGG | CAG | CCC | GCT | GAG | CTC | 1164 |
| Thr | Leu | Glu | Gly | Ile | Pro | Ala | Ala | Val | Pro | Gly | Gln | Pro | Ala | Glu | Leu |      |
|     |     | 355 |     |     |     |     | 360 |     |     |     |     | 365 |     |     |     |      |
| CAG | TTA | AAT | GTC | ACA | AAG | AAT | GAC | GAC | AAG | CGG | GGC | TTC | TTC | TGC | GAC | 1212 |
| Gln | Leu | Asn | Val | Thr | Lys | Asn | Asp | Asp | Lys | Arg | Gly | Phe | Phe | Cys | Asp |      |
|     | 370 |     |     |     |     | 375 |     |     |     |     | 380 |     |     |     |     |      |
| GCT | GCC | CTC | GAT | GTG | GAC | GGG | GAA | ACT | CTG | AGA | AAG | AAC | CAG | AGC | TCT | 1260 |
| Ala | Ala | Leu | Asp | Val | Asp | Gly | Glu | Thr | Leu | Arg | Lys | Asn | Gln | Ser | Ser |      |
| 385 |     |     |     |     | 390 |     |     |     |     | 395 |     |     |     |     | 400 |      |
| GAG | CTT | CGT | GTT | CTG | TAC | GCA | CCT | CGG | CTG | GAT | GAC | TTG | GAC | TGT | CCC | 1308 |
| Glu | Leu | Arg | Val | Leu | Tyr | Ala | Pro | Arg | Leu | Asp | Asp | Leu | Asp | Cys | Pro |      |
|     |     |     |     | 405 |     |     |     |     | 410 |     |     |     |     | 415 |     |      |
| AGG | AGC | TGG | ACG | TGG | CCA | GAG | GGT | CCA | GAG | CAG | ACC | CTC | CAC | TGC | GAG | 1356 |
| Arg | Ser | Trp | Thr | Trp | Pro | Glu | Gly | Pro | Glu | Gln | Thr | Leu | His | Cys | Glu |      |
|     |     |     | 420 |     |     |     |     | 425 |     |     |     |     | 430 |     |     |      |
| GCC | CGT | GGA | AAC | CCT | GAG | CCC | TCC | GTG | CAC | TGT | GCA | AGG | CCT | GAC | GGT | 1404 |
| Ala | Arg | Gly | Asn | Pro | Glu | Pro | Ser | Val | His | Cys | Ala | Arg | Pro | Asp | Gly |      |
|     |     | 435 |     |     |     |     | 440 |     |     |     |     | 445 |     |     |     |      |
| GGG | GCG | GTG | CTA | GCG | CTG | GGC | CTG | TTG | GGT | CCA | GTG | ACC | CGT | GCC | CTC | 1452 |
| Gly | Ala | Val | Leu | Ala | Leu | Gly | Leu | Leu | Gly | Pro | Val | Thr | Arg | Ala | Leu |      |
|     | 450 |     |     |     |     | 455 |     |     |     |     | 460 |     |     |     |     |      |
| GCG | GGC | ACT | TAC | CGA | TGT | ACA | GCA | ATC | AAT | GGG | CAA | GGC | CAG | GCG | GTC | 1500 |
| Ala | Gly | Thr | Tyr | Arg | Cys | Thr | Ala | Ile | Asn | Gly | Gln | Gly | Gln | Ala | Val |      |
| 465 |     |     |     |     | 470 |     |     |     |     | 475 |     |     |     |     | 480 |      |
| AAG | GAT | GTG | ACC | CTG | ACT | GTG | GAA | TAT | GCC | CCA | GCG | CTG | GAC | AGT | GTA | 1548 |
| Lys | Asp | Val | Thr | Leu | Thr | Val | Glu | Tyr | Ala | Pro | Ala | Leu | Asp | Ser | Val |      |
|     |     |     |     | 485 |     |     |     |     | 490 |     |     |     |     | 495 |     |      |
| GGC | TGC | CCA | GAA | CGT | ATT | ACT | TGG | CTG | GAG | GGG | ACA | GAG | GCA | TCG | CTT | 1596 |
| Gly | Cys | Pro | Glu | Arg | Ile | Thr | Trp | Leu | Glu | Gly | Thr | Glu | Ala | Ser | Leu |      |
|     |     |     | 500 |     |     |     |     | 505 |     |     |     |     | 510 |     |     |      |
| AGC | TGT | GTG | GCA | CAC | GGG | GTC | CCA | CCA | CCT | AGC | GTG | AGC | TGT | GTG | CGC | 1644 |
| Ser | Cys | Val | Ala | His | Gly | Val | Pro | Pro | Pro | Ser | Val | Ser | Cys | Val | Arg |      |
|     |     | 515 |     |     |     |     | 520 |     |     |     |     | 525 |     |     |     |      |
| TCT | GGA | AAG | GAG | GAA | GTC | ATG | GAA | GGG | CCC | CTG | CGT | GTG | GCC | CGG | GAG | 1692 |
| Ser | Gly | Lys | Glu | Glu | Val | Met | Glu | Gly | Pro | Leu | Arg | Val | Ala | Arg | Glu |      |
|     | 530 |     |     |     |     | 535 |     |     |     |     | 540 |     |     |     |     |      |
| CAC | GCT | GGC | ACT | TAC | CGA | TGC | GAA | GCC | ATC | AAC | GCC | AGG | GGA | TCA | GCG | 1740 |
| His | Ala | Gly | Thr | Tyr | Arg | Cys | Glu | Ala | Ile | Asn | Ala | Arg | Gly | Ser | Ala |      |
| 545 |     |     |     |     | 550 |     |     |     |     | 555 |     |     |     |     | 560 |      |
| GCC | AAA | AAT | GTG | GCT | GTC | ACG | GTG | GAA | TAT | GGT | CCC | AGT | TTT | GAG | GAG | 1788 |
| Ala | Lys | Asn | Val | Ala | Val | Thr | Val | Glu | Tyr | Gly | Pro | Ser | Phe | Glu | Glu |      |
|     |     |     |     | 565 |     |     |     |     | 570 |     |     |     |     | 575 |     |      |
| TTG | GGC | TGC | CCC | AGC | AAC | TGG | ACT | TGG | GTA | GAA | GGA | TCT | GGA | AAA | CTG | 1836 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Leu | Gly | Cys | Pro | Ser | Asn | Trp | Thr | Trp | Val | Glu | Gly | Ser | Gly | Lys | Leu |  |
|  |  |  | 580 |  |  |  | 585 |  |  |  |  |  | 590 |  |  |  |
| TTT | TCC | TGT | GAA | GTT | GAT | GGG | AAG | CCG | GAA | CCA | CGC | GTG | GAG | TGC | GTG | 1884 |
| Phe | Ser | Cys | Glu | Val | Asp | Gly | Lys | Pro | Glu | Pro | Arg | Val | Glu | Cys | Val |  |
|  |  | 595 |  |  |  | 600 |  |  |  |  | 605 |  |  |  |  |  |
| GGC | TCG | GAG | GGT | GCA | AGC | GAA | GGG | GTA | GTG | TTG | CCC | CTG | GTG | TCC | TCG | 1932 |
| Gly | Ser | Glu | Gly | Ala | Ser | Glu | Gly | Val | Val | Leu | Pro | Leu | Val | Ser | Ser |  |
|  | 610 |  |  |  |  | 615 |  |  |  |  | 620 |  |  |  |  |  |
| AAC | TCT | GGT | TCC | AGA | AAC | TCT | ATG | ACT | CCT | GGT | AAC | CTG | TCA | CCG | GGT | 1980 |
| Asn | Ser | Gly | Ser | Arg | Asn | Ser | Met | Thr | Pro | Gly | Asn | Leu | Ser | Pro | Gly |  |
| 625 |  |  |  |  | 630 |  |  |  |  | 635 |  |  |  |  | 640 |  |
| ATT | TAC | CTC | TGC | AAC | GCC | ACC | AAC | CGG | CAT | GGC | TCC | ACA | GTC | AAA | ACA | 2028 |
| Ile | Tyr | Leu | Cys | Asn | Ala | Thr | Asn | Arg | His | Gly | Ser | Thr | Val | Lys | Thr |  |
|  |  |  | 645 |  |  |  |  | 650 |  |  |  |  | 655 |  |  |  |
| GTC | GTC | GTG | AGC | GCG | GAA | TCA | CCG | CCA | CAG | ATG | GAT | GAA | TCC | AGT | TGC | 2076 |
| Val | Val | Val | Ser | Ala | Glu | Ser | Pro | Pro | Gln | Met | Asp | Glu | Ser | Ser | Cys |  |
|  |  |  | 660 |  |  |  |  | 665 |  |  |  |  | 670 |  |  |  |
| CCG | AGT | CAC | CAG | ACA | TGG | CTG | GAA | GGA | GCC | GAG | GCT | ACT | GCG | CTG | GCC | 2124 |
| Pro | Ser | His | Gln | Thr | Trp | Leu | Glu | Gly | Ala | Glu | Ala | Thr | Ala | Leu | Ala |  |
|  |  | 675 |  |  |  |  | 680 |  |  |  |  | 685 |  |  |  |  |
| TGC | AGT | GCC | AGA | GGC | CGC | CCC | TCT | CCA | CGC | GTG | CGC | TGT | TCC | AGG | GAA | 2172 |
| Cys | Ser | Ala | Arg | Gly | Arg | Pro | Ser | Pro | Arg | Val | Arg | Cys | Ser | Arg | Glu |  |
|  | 690 |  |  |  |  | 695 |  |  |  |  | 700 |  |  |  |  |  |
| GGT | GCA | GCC | AGG | CTG | GAG | AGG | CTA | CAG | GTG | TCC | CGA | GAG | GAT | GCG | GGG | 2220 |
| Gly | Ala | Ala | Arg | Leu | Glu | Arg | Leu | Gln | Val | Ser | Arg | Glu | Asp | Ala | Gly |  |
| 705 |  |  |  |  | 710 |  |  |  |  | 715 |  |  |  |  | 720 |  |
| ACC | TAC | CTG | TGT | GTG | GCT | ACC | AAC | GCG | CAT | GGC | ACG | GAT | TCA | CGG | ACC | 2268 |
| Thr | Tyr | Leu | Cys | Val | Ala | Thr | Asn | Ala | His | Gly | Thr | Asp | Ser | Arg | Thr |  |
|  |  |  |  | 725 |  |  |  |  | 730 |  |  |  |  | 735 |  |  |
| GTC | ACT | GTG | GGT | GTG | GAA | TAC | CGG | CCT | GTG | GTG | GCT | GAG | CTG | GCA | GCC | 2316 |
| Val | Thr | Val | Gly | Val | Glu | Tyr | Arg | Pro | Val | Val | Ala | Glu | Leu | Ala | Ala |  |
|  |  |  | 740 |  |  |  |  | 745 |  |  |  |  | 750 |  |  |  |
| TCG | CCC | CCA | AGC | GTG | CGG | CCT | GGC | GGA | AAC | TTC | ACT | CTG | ACC | TGC | CGT | 2364 |
| Ser | Pro | Pro | Ser | Val | Arg | Pro | Gly | Gly | Asn | Phe | Thr | Leu | Thr | Cys | Arg |  |
|  |  | 755 |  |  |  |  | 760 |  |  |  |  | 765 |  |  |  |  |
| GCA | GAG | GCC | TGG | CCT | CCA | GCC | CAG | ATC | AGC | TGG | CGC | GCG | CCC | CCG | GGA | 2412 |
| Ala | Glu | Ala | Trp | Pro | Pro | Ala | Gln | Ile | Ser | Trp | Arg | Ala | Pro | Pro | Gly |  |
| 770 |  |  |  |  | 775 |  |  |  |  | 780 |  |  |  |  |  |  |
| GCT | CTC | AAC | CTC | GGT | CTC | TCC | AGC | AAC | AAC | AGC | ACG | CTG | AGC | GTG | GCG | 2460 |
| Ala | Leu | Asn | Leu | Gly | Leu | Ser | Ser | Asn | Asn | Ser | Thr | Leu | Ser | Val | Ala |  |
| 785 |  |  |  |  | 790 |  |  |  |  | 795 |  |  |  |  | 800 |  |
| GGT | GCC | ATG | GGC | AGC | CAT | GGT | GGC | GAG | TAT | GAG | TGC | GCA | GCC | ACC | AAT | 2508 |
| Gly | Ala | Met | Gly | Ser | His | Gly | Gly | Glu | Tyr | Glu | Cys | Ala | Ala | Thr | Asn |  |
|  |  |  |  | 805 |  |  |  |  | 810 |  |  |  |  | 815 |  |  |
| GCG | CAT | GGG | CGC | CAC | GCA | CGG | CGC | ATC | ACG | GTG | CGC | GTG | GCC | GGT | CCA | 2556 |
| Ala | His | Gly | Arg | His | Ala | Arg | Arg | Ile | Thr | Val | Arg | Val | Ala | Gly | Pro |  |
|  |  |  | 820 |  |  |  |  | 825 |  |  |  |  | 830 |  |  |  |
| TGG | CTG | TGG | GTC | GCT | GTG | GGC | GGT | GCG | GCA | GGG | GGC | GCG | GCG | CTG | CTG | 2604 |
| Trp | Leu | Trp | Val | Ala | Val | Gly | Gly | Ala | Ala | Gly | Gly | Ala | Ala | Leu | Leu |  |
|  |  | 835 |  |  |  |  | 840 |  |  |  |  | 845 |  |  |  |  |
| GCC | GCA | GGG | GCC | GGC | CTG | GCC | TTC | TAC | GTG | CAG | TCC | ACC | GCT | TGC | AAG | 2652 |
| Ala | Ala | Gly | Ala | Gly | Leu | Ala | Phe | Tyr | Val | Gln | Ser | Thr | Ala | Cys | Lys |  |
|  | 850 |  |  |  |  | 855 |  |  |  |  | 860 |  |  |  |  |  |
| AAG | GGA | GAG | TAC | AAC | GTC | CAG | GAG | GCT | GAG | AGC | TCA | GGC | GAG | GCG | GTG | 2700 |
| Lys | Gly | Glu | Tyr | Asn | Val | Gln | Glu | Ala | Glu | Ser | Ser | Gly | Glu | Ala | Val |  |
| 865 |  |  |  |  | 870 |  |  |  |  | 875 |  |  |  |  | 880 |  |
| TGT | CTC | AAT | GGC | GCG | GGC | GGG | ACA | CCG | GGT | GCA | GAA | GGC | GGA | GCA | GAG | 2748 |
| Cys | Leu | Asn | Gly | Ala | Gly | Gly | Thr | Pro | Gly | Ala | Glu | Gly | Gly | Ala | Glu |  |
|  |  |  |  | 885 |  |  |  |  | 890 |  |  |  |  | 895 |  |  |
| ACC | CCC | GGC | ACT | GCC | GAG | TCA | CCT | GCA | GAT | GGC | GAG | GTT | TTC | GCC | ATC | 2796 |

-continued

```
Thr  Pro  Gly  Thr  Ala  Glu  Ser  Pro  Ala  Asp  Gly  Glu  Val  Phe  Ala  Ile
          900                      905                      910

CAG CTG ACA TCT TCC TGAGCCTGTA TCCAGCTCCC CCAGGGGCCT CGAAAGCACA                    2851
Gln Leu Thr Ser Ser
        915

GGGGTGGACG TATGTATTGT TCACTCTCTA TTTATTCAAC TCCAGGGGCG TCGTCCCCGT                  2911

TTTCTACCCA TTCCCTTAAT AAAGTTTTA TAGGAGAAAA AAAAAAAAAA AAAAAAAAA                    2971

AAAAAAAAAA AAAAAA                                                                  2988
```

( 2 ) INFORMATION FOR SEQ ID NO:2:

( i ) SEQUENCE CHARACTERISTICS:
        ( A ) LENGTH: 917 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Gly  Pro  Ser  Pro  Gly  Leu  Arg  Arg  Thr  Leu  Leu  Gly  Leu  Trp
 1                    5                      10                       15

Ala  Ala  Leu  Gly  Leu  Gly  Ile  Leu  Gly  Ile  Ser  Ala  Val  Ala  Leu  Glu
               20                      25                       30

Pro  Phe  Trp  Ala  Asp  Leu  Gln  Pro  Arg  Val  Ala  Leu  Val  Glu  Arg  Gly
          35                      40                       45

Gly  Ser  Leu  Trp  Leu  Asn  Cys  Ser  Thr  Asn  Cys  Pro  Arg  Pro  Glu  Arg
     50                    55                      60

Gly  Gly  Leu  Glu  Thr  Ser  Leu  Arg  Arg  Asn  Gly  Thr  Gln  Arg  Gly  Leu
65                    70                      75                        80

Arg  Trp  Leu  Ala  Arg  Gln  Leu  Val  Asp  Ile  Arg  Glu  Pro  Glu  Thr  Gln
                85                      90                       95

Pro  Val  Cys  Phe  Phe  Arg  Cys  Ala  Arg  Arg  Thr  Leu  Gln  Ala  Arg  Gly
               100                     105                      110

Leu  Ile  Arg  Thr  Phe  Gln  Arg  Pro  Asp  Arg  Val  Glu  Leu  Val  Pro  Leu
          115                     120                      125

Pro  Pro  Trp  Gln  Pro  Val  Gly  Glu  Asn  Phe  Thr  Leu  Ser  Cys  Arg  Val
     130                    135                     140

Pro  Gly  Ala  Gly  Pro  Arg  Ala  Ser  Leu  Thr  Leu  Thr  Leu  Leu  Arg  Gly
145                    150                     155                       160

Gly  Gln  Glu  Leu  Ile  Arg  Arg  Ser  Phe  Val  Gly  Glu  Pro  Pro  Arg  Ala
                165                     170                      175

Arg  Gly  Ala  Met  Leu  Thr  Ala  Thr  Val  Leu  Ala  Arg  Arg  Glu  Asp  His
               180                     185                      190

Arg  Ala  Asn  Phe  Ser  Cys  Leu  Ala  Glu  Leu  Asp  Leu  Arg  Pro  His  Gly
          195                     200                      205

Leu  Gly  Leu  Phe  Ala  Asn  Ser  Ser  Ala  Pro  Arg  Gln  Leu  Arg  Thr  Phe
     210                     215                     220

Ala  Met  Pro  Pro  Leu  Ser  Pro  Ser  Leu  Ile  Ala  Pro  Arg  Phe  Leu  Glu
225                    230                     235                       240

Val  Gly  Ser  Glu  Arg  Pro  Val  Thr  Cys  Thr  Leu  Asp  Gly  Leu  Phe  Pro
                245                     250                      255

Ala  Pro  Glu  Ala  Gly  Val  Tyr  Leu  Ser  Leu  Gly  Asp  Gln  Arg  Leu  His
               260                     265                      270

Pro  Asn  Val  Thr  Leu  Asp  Gly  Glu  Ser  Leu  Val  Ala  Thr  Ala  Thr  Ala
          275                     280                      285

Thr  Ala  Ser  Glu  Glu  Gln  Glu  Gly  Thr  Lys  Gln  Leu  Met  Cys  Ile  Val
```

-continued

```
                    290                     295                         300
Thr Leu Gly Gly Glu Ser Arg Glu Thr Gln Glu Asn Leu Thr Val Tyr
305                 310                 315                 320
Ser Phe Pro Ala Pro Leu Leu Thr Leu Ser Glu Pro Glu Ala Pro Glu
                325                 330                 335
Gly Lys Met Val Thr Val Ser Cys Trp Ala Gly Ala Arg Ala Leu Val
            340                 345                 350
Thr Leu Glu Gly Ile Pro Ala Ala Val Pro Gly Gln Pro Ala Glu Leu
        355                 360                 365
Gln Leu Asn Val Thr Lys Asn Asp Asp Lys Arg Gly Phe Phe Cys Asp
370                 375                 380
Ala Ala Leu Asp Val Asp Gly Glu Thr Leu Arg Lys Asn Gln Ser Ser
385                 390                 395                 400
Glu Leu Arg Val Leu Tyr Ala Pro Arg Leu Asp Asp Leu Asp Cys Pro
                405                 410                 415
Arg Ser Trp Thr Trp Pro Glu Gly Pro Glu Gln Thr Leu His Cys Glu
            420                 425                 430
Ala Arg Gly Asn Pro Glu Pro Ser Val His Cys Ala Arg Pro Asp Gly
        435                 440                 445
Gly Ala Val Leu Ala Leu Gly Leu Leu Gly Pro Val Thr Arg Ala Leu
450                 455                 460
Ala Gly Thr Tyr Arg Cys Thr Ala Ile Asn Gly Gln Gly Gln Ala Val
465                 470                 475                 480
Lys Asp Val Thr Leu Thr Val Glu Tyr Ala Pro Ala Leu Asp Ser Val
                485                 490                 495
Gly Cys Pro Glu Arg Ile Thr Trp Leu Glu Gly Thr Glu Ala Ser Leu
            500                 505                 510
Ser Cys Val Ala His Gly Val Pro Pro Ser Val Ser Cys Val Arg
        515                 520                 525
Ser Gly Lys Glu Glu Val Met Glu Gly Pro Leu Arg Val Ala Arg Glu
530                 535                 540
His Ala Gly Thr Tyr Arg Cys Glu Ala Ile Asn Ala Arg Gly Ser Ala
545                 550                 555                 560
Ala Lys Asn Val Ala Val Thr Val Glu Tyr Gly Pro Ser Phe Glu Glu
                565                 570                 575
Leu Gly Cys Pro Ser Asn Trp Thr Trp Val Glu Gly Ser Gly Lys Leu
            580                 585                 590
Phe Ser Cys Glu Val Asp Gly Lys Pro Glu Pro Arg Val Glu Cys Val
        595                 600                 605
Gly Ser Glu Gly Ala Ser Glu Gly Val Val Leu Pro Leu Val Ser Ser
610                 615                 620
Asn Ser Gly Ser Arg Asn Ser Met Thr Pro Gly Asn Leu Ser Pro Gly
625                 630                 635                 640
Ile Tyr Leu Cys Asn Ala Thr Asn Arg His Gly Ser Thr Val Lys Thr
                645                 650                 655
Val Val Val Ser Ala Glu Ser Pro Pro Gln Met Asp Glu Ser Ser Cys
            660                 665                 670
Pro Ser His Gln Thr Trp Leu Glu Gly Ala Glu Ala Thr Ala Leu Ala
        675                 680                 685
Cys Ser Ala Arg Gly Arg Pro Ser Pro Arg Val Arg Cys Ser Arg Glu
690                 695                 700
Gly Ala Ala Arg Leu Glu Arg Leu Gln Val Ser Arg Glu Asp Ala Gly
705                 710                 715                 720
```

| | | | | | | | | | | | | | | |
|---|---|---|---|---|---|---|---|---|---|---|---|---|---|---|
|Thr|Tyr|Leu|Cys|Val|Ala|Thr|Asn|Ala|His|Gly|Thr|Asp|Ser|Arg|Thr|
| | | | |725| | | |730| | | | |735| |
|Val|Thr|Val|Gly|Val|Glu|Tyr|Arg|Pro|Val|Val|Ala|Glu|Leu|Ala|Ala|
| | | |740| | | |745| | | | |750| | |
|Ser|Pro|Pro|Ser|Val|Arg|Pro|Gly|Gly|Asn|Phe|Thr|Leu|Thr|Cys|Arg|
| | |755| | | |760| | | | |765| | | |
|Ala|Glu|Ala|Trp|Pro|Pro|Ala|Gln|Ile|Ser|Trp|Arg|Ala|Pro|Pro|Gly|
| |770| | | |775| | | | |780| | | | |
|Ala|Leu|Asn|Leu|Gly|Leu|Ser|Ser|Asn|Asn|Ser|Thr|Leu|Ser|Val|Ala|
|785| | | |790| | | | |795| | | | |800| |
|Gly|Ala|Met|Gly|Ser|His|Gly|Gly|Glu|Tyr|Glu|Cys|Ala|Ala|Thr|Asn|
| | | |805| | | | |810| | | | |815| | |
|Ala|His|Gly|Arg|His|Ala|Arg|Arg|Ile|Thr|Val|Arg|Val|Ala|Gly|Pro|
| | |820| | | | |825| | | | |830| | | |
|Trp|Leu|Trp|Val|Ala|Val|Gly|Gly|Ala|Ala|Gly|Gly|Ala|Ala|Leu|Leu|
| |835| | | | |840| | | | |845| | | | |
|Ala|Ala|Gly|Ala|Gly|Leu|Ala|Phe|Tyr|Val|Gln|Ser|Thr|Ala|Cys|Lys|
|850| | | | |855| | | | |860| | | | | |
|Lys|Gly|Glu|Tyr|Asn|Val|Gln|Glu|Ala|Glu|Ser|Ser|Gly|Glu|Ala|Val|
|865| | | |870| | | | |875| | | | |880| |
|Cys|Leu|Asn|Gly|Ala|Gly|Gly|Thr|Pro|Gly|Ala|Glu|Gly|Gly|Ala|Glu|
| | | |885| | | |890| | | | |895| | | |
|Thr|Pro|Gly|Thr|Ala|Glu|Ser|Pro|Ala|Asp|Gly|Glu|Val|Phe|Ala|Ile|
| | |900| | | |905| | | | |910| | | | |
|Gln|Leu|Thr|Ser|Ser| | | | | | | | | | | |
| | |915| | | | | | | | | | | | | |

( 2 ) INFORMATION FOR SEQ ID NO:3:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..315

( x i ) SEQUENCE DESCRIPTION: SEQ ID NO:3:

| | | | | | | | | | | | | | | | | |
|---|---|---|---|---|---|---|---|---|---|---|---|---|---|---|---|---|
|CCG|GAT|CGG|GTA|GAG|CTA|GTG|CCT|CTG|CCT|CCT|TGG|CAG|CCT|GTA|GGT|48|
|Pro|Asp|Arg|Val|Glu|Leu|Val|Pro|Leu|Pro|Pro|Trp|Gln|Pro|Val|Gly| |
|1| | | |5| | | | |10| | | | |15| | |
|GAG|AAC|TTC|ACC|TTG|AGC|TGC|AGG|GTC|CCG|GGG|GCA|GGA|CCC|CGA|GCG|96|
|Glu|Asn|Phe|Thr|Leu|Ser|Cys|Arg|Val|Pro|Gly|Ala|Gly|Pro|Arg|Ala| |
| | | |20| | | | |25| | | | |30| | | |
|AGC|CTC|ACA|TTG|ACC|TTG|CTG|CGA|GGC|GGA|CAG|GAG|CTG|ATT|CGC|CGA|144|
|Ser|Leu|Thr|Leu|Thr|Leu|Leu|Arg|Gly|Gly|Gln|Glu|Leu|Ile|Arg|Arg| |
| | |35| | | | |40| | | | |45| | | | |
|AGT|TTC|GTA|GGC|GAG|CCA|CCC|CGA|GCT|CGG|TGT|GCG|ATG|CTC|ACC|GCC|192|
|Ser|Phe|Val|Gly|Glu|Pro|Pro|Arg|Ala|Arg|Cys|Ala|Met|Leu|Thr|Ala| |
| |50| | | | |55| | | | |60| | | | | |
|ACG|GTC|CTG|GCG|CGC|AGA|GAG|GAT|CAC|AGG|GAC|AAT|TTC|TCA|TGC|CTC|240|
|Thr|Val|Leu|Ala|Arg|Arg|Glu|Asp|His|Arg|Asp|Asn|Phe|Ser|Cys|Leu| |
|65| | | | |70| | | | |75| | | | |80| |
|GCG|GAG|CTT|GAC|CTG|CGG|ACA|CAC|GGC|TTG|GGA|CTG|TTT|GCA|AAC|AGC|288|
|Ala|Glu|Leu|Asp|Leu|Arg|Thr|His|Gly|Leu|Gly|Leu|Phe|Ala|Asn|Ser| |
| | | |85| | | | |90| | | | |95| | | |

```
TCA GCC CCC AGA CAG CTC CGC ACG TTT                                          315
Ser Ala Pro Arg Gln Leu Arg Thr Phe
            100                 105
```

( 2 ) INFORMATION FOR SEQ ID NO:4:

( i ) SEQUENCE CHARACTERISTICS:
        ( A ) LENGTH: 1781 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 16..1659

( x i ) SEQUENCE DESCRIPTION: SEQ ID NO:4:

```
CAGCTCTCTG TCAGA ATG GCC ACC ATG GTA CCA TCC GTG TTG TGG CCC AGG            51
               Met Ala Thr Met Val Pro Ser Val Leu Trp Pro Arg
                 1           5                      10

GCC TGC TGG ACT CTG CTG GTC TGC TGT CTG CTG ACC CCA GGT GTC CAG             99
Ala Cys Trp Thr Leu Leu Val Cys Cys Leu Leu Thr Pro Gly Val Gln
            15                  20                  25

GGG CAG GAG TTC CTT TTG CGG GTG GAG CCC CAG AAC CCT GTG CTC TCT            147
Gly Gln Glu Phe Leu Leu Arg Val Glu Pro Gln Asn Pro Val Leu Ser
        30                  35                  40

GCT GGA GGG TCC CTG TTT GTG AAC TGC AGT ACT GAT TGT CCC AGC TCT            195
Ala Gly Gly Ser Leu Phe Val Asn Cys Ser Thr Asp Cys Pro Ser Ser
45                  50                  55                  60

GAG AAA ATC GCC TTG GAG ACG TCC CTA TCA AAG GAG CTG GTG GCC AGT            243
Glu Lys Ile Ala Leu Glu Thr Ser Leu Ser Lys Glu Leu Val Ala Ser
                65                  70                  75

GGC ATG GGC TGG GCA GCC TTC AAT CTC AGC AAC GTG ACT GGC AAC AGT            291
Gly Met Gly Trp Ala Ala Phe Asn Leu Ser Asn Val Thr Gly Asn Ser
            80                  85                  90

CGG ATC CTC TGC TCA GTG TAC TGC AAT GGC TCC CAG ATA ACA GGC TCC            339
Arg Ile Leu Cys Ser Val Tyr Cys Asn Gly Ser Gln Ile Thr Gly Ser
        95                 100                 105

TCT AAC ATC ACC GTG TAC GGG CTC CCG GAG CGT GTG GAG CTG GCA CCC            387
Ser Asn Ile Thr Val Tyr Gly Leu Pro Glu Arg Val Glu Leu Ala Pro
110                 115                 120

CTG CCT CCT TGG CAG CCG GTG GGC CAG AAC TTC ACC CTG CGC TGC CAA            435
Leu Pro Pro Trp Gln Pro Val Gly Gln Asn Phe Thr Leu Arg Cys Gln
125                 130                 135                 140

GTG GAG GGT GGG TCG CCC CGG ACC AGC CTC ACG GTG GTG CTG CTT CGC            483
Val Glu Gly Gly Ser Pro Arg Thr Ser Leu Thr Val Val Leu Leu Arg
                145                 150                 155

TGG GAG GAG GAG CTG AGC CGG CAG CCC GCA GTG GAG GAG CCA GCG GAG            531
Trp Glu Glu Glu Leu Ser Arg Gln Pro Ala Val Glu Glu Pro Ala Glu
            160                 165                 170

GTC ACT GCC ACT GTG CTG GCC AGC AGA GAC GAC CAC GGA GCC CCT TTC            579
Val Thr Ala Thr Val Leu Ala Ser Arg Asp Asp His Gly Ala Pro Phe
        175                 180                 185

TCA TGC CGC ACA GAA CTG GAC ATG CAG CCC CAG GGG CTG GGA CTG TTC            627
Ser Cys Arg Thr Glu Leu Asp Met Gln Pro Gln Gly Leu Gly Leu Phe
190                 195                 200

GTG AAC ACC TCA GCC CCC CGC CAG CTC CGA ACC TTT GTC CTG CCC GTG            675
Val Asn Thr Ser Ala Pro Arg Gln Leu Arg Thr Phe Val Leu Pro Val
205                 210                 215                 220

ACC CCC CCG CGC CTC GTG GCC CCC CGG TTC TTG GAG GTG GAA ACG TCG            723
Thr Pro Pro Arg Leu Val Ala Pro Arg Phe Leu Glu Val Glu Thr Ser
                225                 230                 235
```

| | | | | | | | | | | | | | | | | |
|---|---|---|---|---|---|---|---|---|---|---|---|---|---|---|---|---|
| TGG | CCG | GTG | GAC | TGC | ACC | CTA | GAC | GGG | CTT | TTT | CCA | GCC | TCA | GAG | GCC | 771 |
| Trp | Pro | Val | Asp | Cys | Thr | Leu | Asp | Gly | Leu | Phe | Pro | Ala | Ser | Glu | Ala | |
| | | | 240 | | | | | 245 | | | | | 250 | | | |
| CAG | GTC | TAC | CTG | GCG | CTG | GGG | GAC | CAG | ATG | CTG | AAT | GCG | ACA | GTC | ATG | 819 |
| Gln | Val | Tyr | Leu | Ala | Leu | Gly | Asp | Gln | Met | Leu | Asn | Ala | Thr | Val | Met | |
| | | 255 | | | | | 260 | | | | | 265 | | | | |
| AAC | CAC | GGG | GAC | ACG | CTA | ACG | GCC | ACA | GCC | ACA | GCC | ACG | GCG | CGC | GCG | 867 |
| Asn | His | Gly | Asp | Thr | Leu | Thr | Ala | Thr | Ala | Thr | Ala | Thr | Ala | Arg | Ala | |
| 270 | | | | | 275 | | | | | 280 | | | | | | |
| GAT | CAG | GAG | GGT | GCC | CGG | GAG | ATC | GTC | TGC | AAC | GTG | ACC | CTA | GGG | GGC | 915 |
| Asp | Gln | Glu | Gly | Ala | Arg | Glu | Ile | Val | Cys | Asn | Val | Thr | Leu | Gly | Gly | |
| 285 | | | | | 290 | | | | | 295 | | | | | 300 | |
| GAG | AGA | CGG | GAG | GCC | CGG | GAG | AAC | TTG | ACG | GTC | TTT | AGC | TTC | CTA | GGA | 963 |
| Glu | Arg | Arg | Glu | Ala | Arg | Glu | Asn | Leu | Thr | Val | Phe | Ser | Phe | Leu | Gly | |
| | | | | 305 | | | | | 310 | | | | | 315 | | |
| CCC | ATT | GTG | AAC | CTC | AGC | GAG | CCC | ACC | GCC | CAT | GAG | GGG | TCC | ACA | GTG | 1011 |
| Pro | Ile | Val | Asn | Leu | Ser | Glu | Pro | Thr | Ala | His | Glu | Gly | Ser | Thr | Val | |
| | | 320 | | | | | 325 | | | | | 330 | | | | |
| ACC | GTG | AGT | TGC | ATG | GCT | GGG | GCT | CGA | GTC | CAG | GTC | ACG | CTG | GAC | GGA | 1059 |
| Thr | Val | Ser | Cys | Met | Ala | Gly | Ala | Arg | Val | Gln | Val | Thr | Leu | Asp | Gly | |
| | | 335 | | | | | 340 | | | | | 345 | | | | |
| GTT | CCG | GCC | GCG | GCC | CCG | GGG | CAG | ACA | GCT | CAA | CTT | CAG | CTA | AAT | GCT | 1107 |
| Val | Pro | Ala | Ala | Ala | Pro | Gly | Gln | Thr | Ala | Gln | Leu | Gln | Leu | Asn | Ala | |
| 350 | | | | | 355 | | | | | 360 | | | | | | |
| ACC | GAG | AGT | GAC | GAC | GGA | CGC | AGC | TTC | TTC | TGC | AGT | GCC | ACT | CTC | GAG | 1155 |
| Thr | Glu | Ser | Asp | Asp | Gly | Arg | Ser | Phe | Phe | Cys | Ser | Ala | Thr | Leu | Glu | |
| 365 | | | | | 370 | | | | | 375 | | | | | 380 | |
| GTG | GAC | GGC | GAG | TTC | TTG | CAC | AGG | AAC | AGT | AGC | GTC | CAG | CTG | CGA | GTC | 1203 |
| Val | Asp | Gly | Glu | Phe | Leu | His | Arg | Asn | Ser | Ser | Val | Gln | Leu | Arg | Val | |
| | | | | 385 | | | | | 390 | | | | | 395 | | |
| CTG | TAT | GGT | CCC | AAA | ATT | GAC | CGA | GCC | ACA | TGC | CCC | CAG | CAC | TTG | AAA | 1251 |
| Leu | Tyr | Gly | Pro | Lys | Ile | Asp | Arg | Ala | Thr | Cys | Pro | Gln | His | Leu | Lys | |
| | | | 400 | | | | | 405 | | | | | 410 | | | |
| TGG | AAA | GAT | AAA | ACG | AGA | CAC | GTC | CTG | CAG | TGC | CAA | GCC | AGG | GGC | AAC | 1299 |
| Trp | Lys | Asp | Lys | Thr | Arg | His | Val | Leu | Gln | Cys | Gln | Ala | Arg | Gly | Asn | |
| | | | 415 | | | | | 420 | | | | | 425 | | | |
| CCG | TAC | CCC | GAG | CTG | CGG | TGT | TTG | AAG | GAA | GGC | TCC | AGC | CGG | GAG | GTG | 1347 |
| Pro | Tyr | Pro | Glu | Leu | Arg | Cys | Leu | Lys | Glu | Gly | Ser | Ser | Arg | Glu | Val | |
| | 430 | | | | | 435 | | | | | 440 | | | | | |
| CCG | GTG | GGG | ATC | CCG | TTC | TTC | GTC | AAC | GTA | ACA | CAT | AAT | GGT | ACT | TAT | 1395 |
| Pro | Val | Gly | Ile | Pro | Phe | Phe | Val | Asn | Val | Thr | His | Asn | Gly | Thr | Tyr | |
| 445 | | | | | 450 | | | | | 455 | | | | | 460 | |
| CAG | TGC | CAA | GCG | TCC | AGC | TCA | CGA | GGC | AAA | TAC | ACC | CTG | GTC | GTG | GTG | 1443 |
| Gln | Cys | Gln | Ala | Ser | Ser | Ser | Arg | Gly | Lys | Tyr | Thr | Leu | Val | Val | Val | |
| | | | | 465 | | | | | 470 | | | | | 475 | | |
| ATG | GAC | ATT | GAG | GCT | GGG | AGC | TCC | CAC | TTT | GTC | CCC | GTC | TTC | GTG | GCG | 1491 |
| Met | Asp | Ile | Glu | Ala | Gly | Ser | Ser | His | Phe | Val | Pro | Val | Phe | Val | Ala | |
| | | | 480 | | | | | 485 | | | | | 490 | | | |
| GTG | TTA | CTG | ACC | CTG | GGC | GTG | GTG | ACT | ATC | GTA | CTG | GCC | TTA | ATG | TAC | 1539 |
| Val | Leu | Leu | Thr | Leu | Gly | Val | Val | Thr | Ile | Val | Leu | Ala | Leu | Met | Tyr | |
| | | | | 495 | | | | | 500 | | | | | 505 | | |
| GTC | TTC | AGG | GAG | CAC | CAA | CGG | AGC | GGC | AGT | TAC | CAT | GTT | AGG | GAG | GAG | 1587 |
| Val | Phe | Arg | Glu | His | Gln | Arg | Ser | Gly | Ser | Tyr | His | Val | Arg | Glu | Glu | |
| | | 510 | | | | | 515 | | | | | 520 | | | | |
| AGC | ACC | TAT | CTG | CCC | CTC | ACG | TCT | ATG | CAG | CCG | ACA | GAA | GCA | ATG | GGG | 1635 |
| Ser | Thr | Tyr | Leu | Pro | Leu | Thr | Ser | Met | Gln | Pro | Thr | Glu | Ala | Met | Gly | |
| 525 | | | | | 530 | | | | | 535 | | | | | 540 | |
| GAA | GAA | CCG | TCC | AGA | GCT | GAG | TGACGCTGGG | | ATCCGGGATC | | AAAGTTGGCG | | | | | 1686 |
| Glu | Glu | Pro | Ser | Arg | Ala | Glu | | | | | | | | | | |
| | | | | 545 | | | | | | | | | | | | |

GGGGCTTGGC TGTGCCCTCA GATTCCGCAC CAATAAAGCC TTCAAACTCC CAAAAAAAAA 1746

AAAAAAAAAA AAAAAAAAA AAAAAAAAAA AAAA 1781

( 2 ) INFORMATION FOR SEQ ID NO:5:

( i ) SEQUENCE CHARACTERISTICS:
      ( A ) LENGTH: 4900 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

```
CCGAACGCTC CTCGGCCTCT GGTCTNCTCT GGNCCTGGGG ATCCTAGGCA TCTCAGGTAA    60
GAAGAGCCCG CCCGTGGAGC NAGGTGGATA AGGCGGGGGC GGAATTGAAG GACCAGAGAG   120
GGCGGCCCGG GTGTCCCCCT CCAGGCTCCG CCCTCTTCTA GCTTCCACG  CTTCTGTCAC   180
CACCTGGAGN TCGGGGCTTC TCCCCGTCCT TCCTCCACCC CAACACACCT CAATCTTTCA   240
GANCTGAACC CAGCACCTTT TCTGGANTNG GGGNNTTGCA CCTAACCTGT CTCAGGAGAN   300
ACTGTGGCTC TCCTGTCCTC TCCTGCTCTG TNATGCCCTA TGGTTCACAG ACTGGCATCA   360
TCCCTATTCA TGATCCTCAA AGACNCCATC TCCTCAACTG TCATAACTCA GAGCTCTATT   420
CCCCCTCCAC CTGGAGCCCT GGAAACCGGC TTTCTAGGGC TTTTCTCCGC GGTTCTTTCC   480
CGGAGTTCAG CGTTGTGGCT TTTTGTCCAA GTTACTCAAG TTTGGGGACA ATCTCCTTTA   540
AGCCTTTGAC TCAGTCTCAT TTCCACTTTG CTTTGCCCC  AAGCCTCTGT GTCTCTCCCC   600
CATTTCCTGA CGATCTGTCA GAGTCTTAAG AGTGATTTGG TTCCCCATCC CCCTCCAAC    660
TGGAGTCTCC TCCTCACTAT TGATGTGTGC ATCTGAGACC CCATCCCCG  CACCGAGTTT   720
CCCCATCTCT GTCAGTAAAG AGCAAGGCTT CCAGAGACAA CCCTCTAATA GCGCGTCAGT   780
CCCGAATCTT GAGTGGGATG CGGGACTCCC GTGCTATTTC TTGGCGGAGG TCTTTCCTGG   840
TCCTTATGGA CACCCCTGGT TTGGGATATG GGGCCGCTA  AGATTTCAGA GATGGGGTCC   900
CTAGGCTGAG NCCGCGTTTT CCCGGGCAGC GGTCGCGCTA GAACCTTTCT GGGCGGACCT   960
TCAGCCCCGC GTGGCGCTCG TGGAGCGCGG GGCTCGCTG  TGGCTCAACT GCAGCACTAA  1020
CTGTCCGAGG CCGGAGCGCG GTGGCCTGGA GACCTCGCTA CGCCGAAACG GGACCCAGAG  1080
GGGTCTGNAC TGNCTGGCTC GACAGCTGGT GGACATCCGA GANCCTGAAA CCCAGCCGGT  1140
CTGCTTCTTC CNCTGCGCGC GCCGCACACT CCAAGCGCGT GGGCTCATCC GAACTTTCCG  1200
TGAGTTCAGG GTGGGCACNC CCCTTGGGTC TCTGGACCTC CCCCTCAAGC TCCTCCCACC  1260
CGCCCTCTGA TCCTCCTGCT TGTTCTGAAA GTACTACAGC TGGCTAGAGC GGAGTTTTG   1320
GTCCCTTGCA GAGCGACCGG ATCGGGTAGA GCTAGTGCCT CTGCCTCCTT GGCAGCCTGT  1380
AGGTGAGAAC TTCACCTTGA GCTGCAGGGT CCCGGGGGCA GGACCCCGAG CGAGCCTCAC  1440
ATTGACCTTG CTGCGAGGCG GCCAGGAGCT GATTCGCCGA AGTTTCGTAG GCGAGCCACC  1500
CCGAGCTCGG GGTGCGATGC TCACCGCCAC GGTCCTGGCG CGCAGAGAGG ATCACAGGGC  1560
CAATTTCTCA TGCCTCGCGG AGCTTGACCT GCGNCCACAC GGCTTGGGAC TGTTTGCANA  1620
CAGCTCAGCC CCAGACAGC  TCCGCACGTT TGGTGAGTGT GGACCCTAAC TGACAGATTT  1680
TAAGAAGTTT AGGGCAGCCA GGCGTGGTGG CATGGTGTCG TAGGCCCTAA GTCCCAGCCC  1740
AAGCAGANCT AAGNCGGATC TCTTGTGAAT TAAAAGTCTA GCTCGTCTAC ATAACGAGGN  1800
CTGCATAGTT AAATCCCCCA AAAGTCTAAG CAGCTAGCCC TTACTTCCAA CACAAGTACT  1860
```

```
-continued
AGCTTAAGTA  CTTTCTCCTG  TGAGCTTTTT  CCTTTATGTA  TTTACTCGTT  GAGAGAAAAA  1920
GAGAGTGTGT  GTACGTGCCT  TTATGCACAT  GCCGCAGTGC  TTGTATGGAA  GTTAAAGAAT  1980
AAGGAGGCGT  TCTGCCCTTC  CATCCTGTGG  GTCCTAGGGG  TGGTATTAGC  TCCTCAGGCT  2040
TTGTTAGTNA  CAAGCGCCTA  GGCTTGGGGA  GCCATCTCGC  CCGCTCCTCT  GTATCTTTAG  2100
GGTGAAACCA  GACAATGCAT  GCAAATTGGT  TGATCAACAC  TGAATGTTTA  GTTCGTAAAT  2160
TCAAGCTCTG  TTCTTTGTCT  TCCTCAGCCA  TGCCTCCACT  TTCCCCCGAG  CCTTATTGCC  2220
CCACGATTCT  TAGAAGTGGG  CTCAGAAAGG  CCGGTGACKT  GCACTTTGGA  TGGACTGTTT  2280
CCTGCCCCAG  AAGCGGGGT   TTACTTCTCT  CTGGGAGATC  AGAGGCTTCA  TCCTAATGTG  2340
ACCCTCGACG  GGGAGAGCCT  TGTGGCCACT  GCCACAGCTA  CAGCAAGTGA  AGAACAGGAA  2400
GGCACCAAAC  AGCTGATGTG  CATCGTGACC  CTCGGGGGCG  AAAGCAGGGA  GACCCAGGAA  2460
AACCTGACTG  TCTACAGTAA  GGGGAATCCA  ACAAGACCTT  CAATAGCTCA  GACTGGGGCT  2520
GGGGCTGGGT  CTGGGTCTGG  GGCCAGAGTC  TCACAAAGGC  GGAGCCTATA  AAGTGGGCGG  2580
GACCTCCACA  CCAGAACAAG  CCGGGCGGGA  GAGTTCCAGG  GCAGGAGCAG  ATAGAAGTTG  2640
GAAATTAATA  GATTGGGTTG  AGTTCCCTGA  GTGGGAGTG   AACCCCACCC  AATTCTCTGT  2700
CCCCAGGCTT  CCCGGCTCCT  CTTCTGACTT  TAAGTGAGCC  AGAAGCCCCC  GAGGGAAAGA  2760
TGGTGACCGT  AAGCTGCTGG  GCAGGGGCCC  GAGCCCTTGT  CACCTTGGAG  GGAATTCCAA  2820
GGACCCTCTT  ACCGGCCCCA  TCTTTAACCT  TATCGTATCC  CCTCTGCCTC  ATGCCCGCAG  2880
ACGCACCTCG  GCTGGATGAC  TTGGACTGTC  CCAGGAGCTG  GACGTGGCCA  GAGGGTCCAG  2940
AGCAGACCCT  CCACTGCGAG  GCCCGTGGAA  ACCCTGAGCC  CTCCGTGCAC  TGTGCAAGGC  3000
CTGACGGTGG  GGCGGTGCTA  GCGCTGGGCC  TGTTGGGTCC  AGTGACCCGT  GCCCTCGCGG  3060
GCACTTACCG  ATGTACAGCA  ATCAATGGGC  AAGGCCAGGC  GGTCAAGGAT  GTGACCCTGA  3120
CTGTGGAATG  TGAGTAGGGG  GAGGTGGGCA  TGCTTATCCC  TTTAAGGTCA  CGGAGTGTAC  3180
TGGGAGACTG  GCTATACGGA  AAGGAAAGAA  GCCTAGGTTC  AGCAGGGATT  GGGAAAACAC  3240
TGAAGGAAAG  TGGTGTGGTG  TTTACAAACT  TAACGGTGGT  AACTGGGCAC  GGTCTGGCAA  3300
AAACAGACAG  CCAAGAGAGT  GTGCCTGGGA  AGCTGCAATG  GGGGCTTTGT  GGGAATTGGT  3360
CAACAGCACC  CTGAGATCTC  AGGAAAGGGG  CCTGAAGTTA  TCTCCAGAAC  CCATGTGAAG  3420
GCAGGAAGAG  AGAACGCCCA  CCTTTTCCTG  CTCCCCCCAA  CCCCCCCCCA  CATATCACAC  3480
GGAGTATATA  AATAAATAAA  ATGGCTCCTG  CCGGAGGGAG  TGAGAAGCTG  TCTCCTGCAG  3540
GCTCAGAGCA  GTGGTAGTGC  ATGCCTTTAA  TCCCAGCACT  CGGTAGGCAA  AGGCAGGCAG  3600
ATCTCTGTGA  ATGTGGGGCC  AGCCTGGTCT  GTACAGAGAA  ATCCTGTCTC  AAAACAAACC  3660
AGCAAAGAAA  CAAAACCAAA  ATCAATTCCA  GATGCCCCAG  CGCTGGACAG  TGTAGGCTGC  3720
CCANGACGTA  TTACTTGNCT  GGAGGGGACA  GAGGCATCGC  TTAGCTGTGT  GGCACACGGG  3780
GTCCCACCAC  CTAGCGTGAG  CTGTGTGCGC  TCTGGAAAGG  AGGAAGTCAT  GGAAGGGCCC  3840
CTGCGTGTGG  CCCGGGAGCA  CGCTGGCACT  TACCGATGCG  AAGCCATCAA  CGCCAGGGGA  3900
TCAGCGGNCA  AAAATGTGGC  TGTCACGGTG  GAATGTGAGT  AGGGGTGGCT  ACGGAAATGT  3960
CCACACCTGC  GTCCTCTGTC  CTCAGTGTGA  ACTCCTATTT  CCCTGCTTCC  TAGATGGTCC  4020
CAGTTNTGAG  GAGTTGGGCT  GCCCCAGCAA  CTGGACTTGG  GTAGAAGGAT  CTGGAAAACT  4080
GTTTTCCTGT  GAAGTTGATG  GGAAGCCGGA  ACCACGCGTG  GAGTGCGTGG  GCTCGGAGGG  4140
TGCAAGCGAA  GGGGTAGTGT  TGCCCCTGGT  GTCCTCGAAC  TCTGGTTCCA  GAAACTCTAT  4200
GACTCCTGGT  AACCTGTCAC  CGGGTATTTA  CCTCTGCAAC  GCCACCAACC  GGCATGGCTC  4260
```

| | | | | | |
|---|---|---|---|---|---|
| CACAGTCAAA | ACAGTCGTCG | TGAGCGCGGA | ATGTGAGCAG | GGGCCCAGGT | GGGCGGAGAG | 4320
| TACCGGGTGT | CCCAGGATCT | TTTCTTTCCC | TGATGCCCCT | CCTTATGGTG | GCTGATCTGC | 4380
| AGCACCGCCA | CAGATGGATG | AATCCAGTTG | CCCGAGTCAC | CAGACATGGC | TGGAAGGAGC | 4440
| CGAGGCTACT | GCGCTGGCCT | GCAGTGACAG | GGGNCGCCCC | TCTCCACGCG | TGCGCTGTTC | 4500
| CAGGGAAGGT | GCAGCCAGGC | TGGAGAGGCT | ACAGGTGTCC | CGAGAGGATG | CGGGGACCTA | 4560
| CCTGTGTGTG | GCTACCAACG | CGCATGGCAC | GGATTCACGG | ACCGTCACTG | TGGGTGTGGA | 4620
| ATGTGAGTGA | GGACAGCGCT | GAATGAAGAC | GACTCAGACC | GCCAGAAAAG | TGCCTTGAGG | 4680
| CCTGGGATGT | ATGATCCAGT | GGGTAGAGTG | CTCAATTAGC | ACTCACTAAA | ATGTATATTC | 4740
| TATTCCTAAT | ACTCTTTAAT | TTTANCCTTT | GGGAGGCAGA | GACAGGCAGA | TCTCTGTTCC | 4800
| GGGATAACCT | GCTCTCTGTC | TAGGACAGCT | TGGTCTACAG | AGGGGNTACA | GGCCCCCCCT | 4860
| CCCAAGATTG | NATAGCAACC | CTCTGGCTCC | CTGTCTCTCT | | | 4900

( 2 ) INFORMATION FOR SEQ ID NO:6:

( i ) SEQUENCE CHARACTERISTICS:
        ( A ) LENGTH: 1295 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| NGAATTCCGG | CGGATCGGGT | AGAGCTAGTG | CCTCTGCCTC | CTTGGCAGCC | TGTAGGTGAG | 60
| AACTTCACCT | TGAGCTGCAG | GGTCCCGGGG | GCAGGACCCC | GAGCGAGCCT | CACATTGACC | 120
| TTGCTGCGAG | GCGGCCAGGA | GCTGATTCGC | CGAAGTTTCG | TAGGCGAGCC | ACCCCGAGCT | 180
| CGGGGTGCGA | TGCTCACCGC | CACGGTCCTG | GCGCGCAGAG | AGGATCACAG | GGCCAATTTC | 240
| TCATGCCTCG | CGGAGCTTGA | CCTGCGGCCA | CACGGCTTGG | GACTGTTTGC | AAACAGCTCA | 300
| GCCCCCAGAC | AGCTCCGCAC | GTTTGCCATG | CCTCCACTTT | CCCCGAGCCT | TATTGCCCCA | 360
| CGATTCTTAG | AAGTGGGCTC | AGAAAGGCCG | GTGACTTGCA | CTTTGGATGG | ACTGTTTCCT | 420
| GCCCCAGAAG | CCGGGGTTTA | CCTCTCTCTG | GGAGATCAGA | GGCTTCATCC | TAATGTGACC | 480
| CTCGACGGGG | AGAGCCTTGT | GGCCACTGCC | ACAGCTACAG | CAAGTGAAGA | ACAGGAAGGC | 540
| ACCAAACAGC | TGATGTGCAT | CGTGACCCTC | GGGGGCGAAA | GCAGGGAGAC | CCAGGAAAAC | 600
| CTGACTGTCT | ACAGCTTCCC | GGCTCCTCTT | CTGACTTTAA | GTGAGCCAGA | AGCCCCGAG | 660
| GGAAAGATGG | TGACCGTAAG | CTGCTGGGCA | GGGGCCCGAG | CCCTTGTCAC | CTTGGAGGGA | 720
| ATTCCAAGGA | CCCTCTTACC | GGCCCCATCT | TTAACCTTAT | CGTATCCCCT | CTGCCTCATG | 780
| CCCGCAGACG | CACCTCGGCT | GGATGACTTG | GACTGTCCCA | GGAGCTGGAC | GTGGCCAGAG | 840
| GGTCCAGAGC | AGACCCTCCA | CTGCGAGGCC | CGTGGAAACC | CTGAGCCCTC | CGTGCACTGT | 900
| GCAAGGCCTG | ACGGTGGGGC | GGTGCTAGCG | CTGGGCCTGT | TGGGTCCAGT | GACCCGTGCC | 960
| CTCGCGGGCA | CTTACCGATG | TACAGCAATC | AATGGGCAAG | GCCAGGCGGT | CAAGGATGTG | 1020
| ACCCTGACTG | TGGAATATGC | CCCAGCGCTG | GACAGTGTAG | GCTGCCCAGA | ACGTATTACT | 1080
| TGGCTGGAGG | GGACAGAGGC | ATCGCTTAGC | TGTGTGGCAC | ACGGGGTCCC | ACCACCTAGC | 1140
| GTGAGCTGTG | TGCGCTCTGG | AAAGGAGGAA | GTCATGGAAG | GGCCCCTGCG | TTTTGGCCGG | 1200
| GAGCACGCTG | GCACTTACCG | ATGCGAAGCC | ATCAACGCCA | GGGATCAGC | GGCCAAAAAT | 1260
| GTGGCTGTCA | CGGTGGAATA | TGGTCCCCGG | AATTC | | | 1295

( 2 ) INFORMATION FOR SEQ ID NO:7:

( i ) SEQUENCE CHARACTERISTICS:
        ( A ) LENGTH: 2214 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
CGAATCTTGA GTGGGATGCG GGACTCCCGT GCTATTTCTT GGCGGAGGTC TTTCCTGGTC      60
CTTATGGACA CCCCTGGTTT GGGATATGGG GGCCGCTAAG ATTTCAGAGA TGGGGTCCCT     120
AGGCTGAGCC CGCGTTTTCC CGGGCAGCGG TCGCGCTAGA ACCTTTCTGG GCGGACCTTC     180
AGCCCCGCGT GGCGCTCGTG GAGCGCGGGG GCTCGCTGTG GCTCAACTGC AGCACTAACT     240
GTCCGAGGCC GGAGCGCGGT GGYCTGGAGA CCTCGCTACG CCGAAACGGG ACCCAGAGGG     300
GTCTGCGCTG GCTGGCTCGA CAGMTGGTGG ACATCCGAGA GCCTGAAACC CAGTCGGTCT     360
GCTTCTTCCG CTGGGCGCGC CGCACACTCC AAGNGAGTGG GCTCATCCGA ACTTTCCAGC     420
GACCGGATCG GGTAGAGCTA GTGCCTCTGN CTCCTTGGCA GCCTGTAGGT GAGAACTTCA     480
CCTTGAGCTG CAGGGTCCCG GGGGCAGGAC CCCGAGCGAG CCTCACATTG ACCTTGCTGC     540
GAGGCGGCCA GGAGCTGATT CGCCGAAGTT TCGTAGGCGA GCCACCCCGA GCTCGGGGTG     600
CGATGCTCAC CGCCACGGTC CTGGCGCGCA GAGAGGATCA CAGGGCCAAT TTCTCATGCC     660
TCGCGGAGCT TGACCTGCGG ACACACGGCT TGGGACTGTT TGCAAACAGC TCAGCCCCCA     720
GACAGCTCCG CACGTTTGGC ATGCCTCCAC TTTCCCCGAG CCTTATTGNC CCACGATTCT     780
TAGAAGTGGG CTCAGAAAGG CCGGTGACTT GCACTTTGGA TGGACTGTTT CCTGCCCCAG     840
AAGCCGGGGT TTACCTCTCT CTGGGAGATC AGAGGCTTCA TCCTAATGTG ACCCTCGACG     900
GGGAGAGCCT TGTGGCCACT GNCACAGMTA CAGCAAGTGA AGAACAGGAA GGCACCAAAC     960
AGCTGATGTG CATCGTGACC CTCGGGGGCG AAAGCAGGGA GACCCAGGAA AACCTGACTG    1020
TCTACAGCTT CCCGGCTCCT CTTCTGACTT TAAGTGAGCC AGAAGCCCCC GAGGGAAAGA    1080
TGGTGACCGT AAGCTGCTGG GCAGGGGCCC GAGCCCTTGT CACCTTGGAG GGAATTCCAG    1140
CTGCGGTCCC TGGGCAGCCC GCTGAGCTCC AGTTAAATGT CACAAAGAAT GACGACAAGC    1200
GGGGCTTCTT CTGCGACGCT GCCCTCGATG TGGACGGGGA AACTCTGAGA AAGAACCAGA    1260
GCTCTGAGCT TCGTGTTCTG TACGCACCTC GGCTGGATGA CTTGGACTGT CCCAGGAGCT    1320
GGACGTGGCC AGAGGGTCCA GAGCAGACCC TCCACTGCGA GGCCCGTGGA AACCCTGAGC    1380
CCTCCGTGCA CTGTGCAAGG CCTGACGGTG GGGCGGTGCT AGCGCTGGGC CTGTTGGGTC    1440
CAGTGACCCG TGCCCTCGCG GGAACTTACC GATGTACAGC AATCAATGGG CAAGGCCAGG    1500
CGGTCAAGGA TGTGACCCTG ACTGTGGAAT ATGCCCAGC GCTGGACAGT GTAGGCTGCC    1560
CAGAACGTAT TACTTGGCTG GAGGGACAG AGGCATCGCT TAGCTGTGTG GCACACGGGG    1620
TCCCACCACC TAGCGTGAGC TGTGTGCGCT CTGGAAAGGA GGAAGTCATG GAAGGGCCCC    1680
TGCGTGTGGC CCGGAGCAC GCTGGCACTT ACCGATGCGA AGCCATCAAC GNCAGGGGAT    1740
CAGCGGWCAA AAATGTGGCT GTCACGGTGG AATATGGTCC CAGTTTGGAG GAGTTGGGCT    1800
GCCCCAGYAA CTGGACTTGG GTAGAAGGAT CTGGAAAACT GTTTCCTGT GAAGTTGATG    1860
GGAAGCCGGA ACCACGCGTG GAGTGCGTGG GCTCGGAGGG TGCAAGCGAA GGGGTAGTGT    1920
TGCCCCTGGT GTCCTCGAAC TCTGGTTCCA GAAACTCTAT GACTCCTGGT AACCTGTCAC    1980
CGGGTATTTA CCTCTGCAAC GCCACCAACC GGMATGGNTC CACAGTCAAA ACAGTCGTCG    2040
```

5,702,917

49 50
-continued

| TGAGCGCGGA | ATCACCGCCA | CAGATGGATG | AATCCAGTTG | CCCGAGTCAC | CAGACATGGN | 2100 |
| TGGAAGGAGC | CGAGGNTACT | GCGCTGGCCT | GCAGTGCCAG | AGGNCGCCCC | TCTCCACGCG | 2160 |
| TGCGCTGTTC | CAGGGAAGGT | GCAGMCAGGC | TGGAGAGGNT | ACAGGTGTCC | CGAG | 2214 |

( 2 ) INFORMATION FOR SEQ ID NO:8:

( i ) SEQUENCE CHARACTERISTICS:
        ( A ) LENGTH: 5077 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| CCGAACGCTC | CTCGGCCTCT | GGTCTNCTCT | GGNCCTGGGG | ATCCTAGGCA | TCTCAGGTAA | 60 |
| GAAGAGCCCG | CCCGTGGAGC | NAGGTGGATA | AGGCGGGGGC | GGAATTGAAG | GACCAGAGAG | 120 |
| GGCGGCCCGG | GTGTCCCCCT | CCAGGCTCCG | CCCTCTTCTA | GCTTCCACG | CTTCTGTCAC | 180 |
| CACCTGGAGN | TCGGGGCTTC | TCCCCGTCCT | TCCTCCACCC | CAACACACCT | CAATCTTTCA | 240 |
| GANCTGAACC | CAGCACCTTT | TCTGGANTNG | GGGNNTTGCA | CCTAACCTGT | CTCAGGAGAN | 300 |
| ACTGTGGCTC | TCCTGTCCTC | TCCTGCTCTG | TNATGCCCTA | TGGTTCACAG | ACTGGCATCA | 360 |
| TCCCTATTCA | TGATCCTCAA | AGACNCCATC | TCCTCAACTG | TCATAACTCA | GAGCTCTATT | 420 |
| CCCCCTCCAC | CTGGAGCCCT | GGAAACCGGC | TTTCTAGGGC | TTTTCTCCGC | GGTTCTTTCC | 480 |
| CGGAGTTCAG | CGTTGTGGCT | TTTTGTCCAA | GTTACTCAAG | TTTGGGGACA | ATCTCCTTTA | 540 |
| AGCCTTTGAC | TCAGTCTCAT | TTCCACTTTG | CTTTTGCCCC | AAGCCTCTGT | GTCTCTCCCC | 600 |
| CATTTCCTGA | CGATCTGTCA | GAGTCTTAAG | AGTGATTTGG | TTCCCCATCC | CCCTCCAAC | 660 |
| TGGAGTCTCC | TCCTCACTAT | TGATGTGTGC | ATCTGAGACC | CCCATCCCCG | CACCGAGTTT | 720 |
| CCCCATCTCT | GTCAGTAAAG | AGCAAGGCTT | CCAGAGACAA | CCCTCTAATA | GCGCGTCAGT | 780 |
| CCCGAATCTT | GAGTGGGATG | CGGGACTCCC | GTGCTATTTC | TTGGCGGAGG | TCTTTCCTGG | 840 |
| TCCTTATGGA | CACCCCTGGT | TTGGGATATG | GGGGCCGCTA | AGATTTCAGA | GATGGGGTCC | 900 |
| CTAGGCTGAG | NCCGCGTTTT | CCCGGGCAGC | GGTCGCGCTA | GAACCTTTCT | GGGCGGACCT | 960 |
| TCAGCCCCGC | GTGGCGCTCG | TGGAGCGCGG | GGGCTCGCTG | TGGCTCAACT | GCAGCACTAA | 1020 |
| CTGTCCGAGG | CCGGAGCGCG | GTGGCCTGGA | GACCTCGCTA | CGCCGAAACG | GGACCCAGAG | 1080 |
| GGGTCTGNAC | TGNCTGGCTC | GACAGCTGGT | GGACATCCGA | GANCCTGAAA | CCCAGCCGGT | 1140 |
| CTGCTTCTTC | CNCTGCGCGC | GCCGCACACT | CCAAGCGCGT | GGGCTCATCC | GAACTTTCCG | 1200 |
| TGAGTTCAGG | GTGGGCACNC | CCCTTGGGTC | TCTGGACCTC | CCCCTCAAGC | TCCTCCCACC | 1260 |
| CGCCCTCTGA | TCCTCCTGCT | TGTTCTGAAA | GTACTACAGC | TGGCTAGAGC | GGAGTTTTTG | 1320 |
| GTCCTTGCA | GAGCGACCGG | ATCGGGTAGA | GCTAGTGCCT | CTGCCTCCTT | GGCAGCCTGT | 1380 |
| AGGTGAGAAC | TTCACCTTGA | GCTGCAGGGT | CCCGGGGGCA | GGACCCCGAG | CGAGCCTCAC | 1440 |
| ATTGACCTTG | CTGCGAGGCG | GCCAGGAGCT | GATTCGCCGA | AGTTTCGTAG | GCGAGCCACC | 1500 |
| CCGAGCTCGG | GGTGCGATGC | TCACCGCCAC | GGTCCTGGCG | CGCAGAGAGG | ATCACAGGGC | 1560 |
| CAATTTCTCA | TGCCTCGCGG | AGCTTGACCT | GCGNCCACAC | GGCTTGGGAC | TGTTTGCANA | 1620 |
| CAGCTCAGCC | CCCAGACAGC | TCCGACGTT | TGGTGAGTGT | GGACCCTAAC | TGACAGATTT | 1680 |
| TAAGAAGTTT | AGGGCAGCCA | GGCGTGGTGG | CATGGTGTCG | TAGGCCCTAA | GTCCCAGCCC | 1740 |
| AAGCAGANCT | AAGNCGGATC | TCTTGTGAAT | TAAAAGTCTA | GCTCGTCTAC | ATAACGAGGN | 1800 |
| CTGCATAGTT | AAATCCCCCA | AAAGTCTAAG | CAGCTAGCCC | TTACTTCCAA | CACAAGTACT | 1860 |

```
AGCTTAAGTA CTTTCTCCTG TGAGCTTTTT CCTTTATGTA TTTACTCGTT GAGAGAAAAA    1920
GAGAGTGTGT GTACGTGCCT TTATGCACAT GCCGCAGTGC TTGTATGGAA GTTAAAGAAT    1980
AAGGAGGCGT TCTGCCCTTC CATCCTGTGG GTCCTAGGGG TGGTATTAGC TCCTCAGGCT    2040
TTGTTAGTNA CAAGCGCCTA GGCTTGGGGA GCCATCTCGC CCGCTCCTCT GTATCTTTAG    2100
GGTGAAACCA GACAATGCAT GCAAATTGGT TGATCAACAC TGAATGTTTA GTCGTAAAT     2160
TCAAGCTCTG TTCTTTGTCT TCCTCAGCCA TGCCTCCACT TTCCCCGAG CCTTATTGCC     2220
CCACGATTCT TAGAAGTGGG CTCAGAAAGG CCGGTGACKT GCACTTTGGA TGGACTGTTT    2280
CCTGCCCCAG AAGCCGGGGT TTACTTCTCT CTGGGAGATC AGAGGCTTCA TCCTAATGTG    2340
ACCCTCGACG GGGAGAGCCT TGTGGCCACT GCCACAGCTA CAGCAAGTGA GAACAGGAA     2400
GGCACCAAAC AGCTGATGTG CATCGTGACC CTCGGGGCG AAAGCAGGGA GACCCAGGAA     2460
AACCTGACTG TCTACAGTAA GGGGAATCCA ACAAGACCTT CAATAGCTCA GACTGGGCT     2520
GGGGCTGGGT CTGGGTCTGG GGCCAGAGTC TCACAAAGGC GGAGCCTATA AAGTGGGCGG    2580
GACCTCCACA CCAGAACAAG CCGGGCGGGA GAGTTCCAGG GCAGGAGCAG ATAGAAGTTG    2640
GAAATTAATA GATTGGGTTG AGTTCCCTGA GTGGGGAGTG AACCCCACCC AATTCTCTGT    2700
CCCCAGGCTT CCCGGCTCCT CTTCTGACTT TAAGTGAGCC AGAAGCCCCC GAGGGAAAGA    2760
TGGTGACCGT AAGCTGCTGG GCAGGGGCCC GAGCCCTTGT CACCTTGGAG GGAATTCCAG    2820
CTGCGGTCCC TGGGCAGCCC GCTGAGCTCC AGTTAAATGT CACAAAGAAT GACGACAAGC    2880
GGGGCTTCTT CTGCGACGCT GCCCTCGATG TGGACGGGGA AACTCTGAGA AAGAACCAGA    2940
GCTCTGAGCT TCGTGTTCTG TGTGAGTGGA TGTTCACTTT ATCTCTGTGA ATTCCAAGGA    3000
CCCTCTTACC GGCCCCATCT TTAACCTTAT CGTATCCCCT CTGCCTCATG CCCGCAGACG    3060
CACCTCGGCT GGATGACTTG GACTGTCCCA GGAGCTGGAC GTGGCCAGAG GGTCCAGAGC    3120
AGACCCTCCA CTGCGAGGCC CGTGGAAACC CTGAGCCCTC CGTGCACTGT GCAAGGCCTG    3180
ACGGTGGGGC GGTGCTAGCG CTGGGCCTGT TGGGTCCAGT GACCCGTGCC CTCGCGGGCA    3240
CTTACCGATG TACAGCAATC AATGGGCAAG GCCAGGCGGT CAAGGATGTG ACCCTGACTG    3300
TGGAATGTGA GTAGGGGGAG GTGGGCATGC TTATCCCTTT AAGGTCACGG AGTGTACTGG    3360
GAGACTGGCT ATACGGAAAG GAAAGAAGCC TAGGTTCAGC AGGGATTGGG AAAACACTGA    3420
AGGAAAGTGG TGTGGTGTTT ACAAACTTAA CGGTGGTAAC TGGGCACGGT CTGGCAAAAA    3480
CAGACAGCCA AGAGAGTGTG CCTGGGAAGC TGCAATGGGG GCTTTGTGGG AATTGGTCAA    3540
CAGCACCCTG AGATCTCAGG AAAGGGGCCT GAAGTTATCT CCAGAACCCA TGTGAAGGCA    3600
GGAAGAGAGA ACGCCCACCT TTTCCTGCTC CCCCCAACCC CCCCCCACAT ATCACACGGA    3660
GTATATAAAT AAATAAAATG GCTCCTGCCG GAGGGAGTGA GAAGCTGTCT CCTGCAGGCT    3720
CAGAGCAGTG GTAGTGCATG CCTTTAATCC CAGCACTCGG TAGGCAAAGG CAGGCAGATC    3780
TCTGTGAATG TGGGGCCAGC CTGGTCTGTA CAGAGAAATC CTGTCTCAAA ACAAACCAGC    3840
AAAGAAACAA AACCAAAATC AATTCCAGAT GCCCCAGCGC TGGACAGTGT AGGCTGCCCA    3900
NGACGTATTA CTTGNCTGGA GGGGACAGAG GCATCGCTTA GCTGTGTGGC ACACGGGGTC    3960
CCACCACCTA GCGTGAGCTG TGTGCGCTCT GGAAGGAGG AAGTCATGGA AGGGCCCCTG     4020
CGTGTGGCCC GGGAGCACGC TGGCACTTAC CGATGCGAAG CCATCAACGC CAGGGGATCA    4080
GCGGNCAAAA ATGTGGCTGT CACGGTGGAA TGTGAGTAGG GGTGGCTACG GAAATGTCCA    4140
CACCTGCGTC CTCTGTCCTC AGTGTGAACT CCTATTTCCC TGCTTCCTAG ATGGTCCCAG    4200
TTNTGAGGAG TTGGGCTGCC CCAGCAACTG GACTTGGGTA GAAGGATCTG GAAAACTGTT    4260
```

-continued

```
TTCCTGTGAA GTTGATGGGA AGCCGGAACC ACGCGTGGAG TGCGTGGGCT CGGAGGGTGC    4320
AAGCGAAGGG GTAGTGTTGC CCCTGGTGTC CTCGAACTCT GGTTCCAGAA ACTCTATGAC    4380
TCCTGGTAAC CTGTCACCGG GTATTTACCT CTGCAACGCC ACCAACCGGC ATGGCTCCAC    4440
AGTCAAAACA GTCGTCGTGA GCGCGGAATG TGAGCAGGGG CCCAGGTGGG CGGAGAGTAC    4500
CGGGTGTCCC AGGATCTTTT CTTTCCCTGA TGCCCCTCCT TATGGTGGCT GATCTGCAGC    4560
ACCGCCACAG ATGGATGAAT CCAGTTGCCC GAGTCACCAG ACATGGCTGG AAGGAGCCGA    4620
GGCTACTGCG CTGGCCTGCA GTGACAGGGG NCGCCCTCT CCACGCGTGC GCTGTTCCAG    4680
GGAAGGTGCA GCCAGGCTGG AGAGGCTACA GGTGTCCCGA GAGGATGCGG GGACCTACCT    4740
GTGTGTGGCT ACCAACGCGC ATGGCACGGA TTCACGGACC GTCACTGTGG GTGTGGAATG    4800
TGAGTGAGGA CAGCGCTGAA TGAAGACGAC TCAGACCGCC AGAAAAGTGC CTTGAGGCCT    4860
GGGATGTATG ATCCAGTGGG TAGAGTGCTC AATTAGCACT CACTAAAATG TATATTCTAT    4920
TCCTAATACT CTTTAATTTT ANCCTTTGGG AGGCAGAGAC AGGCAGATCT CTGTTCCGGG    4980
ATAACCTGCT CTCTGTCTAG GACAGCTTGG TCTACAGAGG GGNTACAGGC CCCCCTCCC    5040
AAGATTGNAT AGCAACCCTC TGGCTCCCTG TCTCTCT                             5077
```

( 2 ) INFORMATION FOR SEQ ID NO:9:

( i ) SEQUENCE CHARACTERISTICS:
        ( A ) LENGTH: 1472 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
NGAATTCCGG CGGATCGGGT AGAGCTAGTG CCTCTGCCTC CTTGGCAGCC TGTAGGTGAG      60
AACTTCACCT TGAGCTGCAG GGTCCGGGG GCAGGACCCC GAGCGAGCCT CACATTGACC      120
TTGCTGCGAG GCGGCCAGGA GCTGATTCGC CGAAGTTTCG TAGGCGAGCC ACCCCGAGCT    180
CGGGGTGCGA TGCTCACCGC CACGGTCCTG GCGCGCAGAG AGGATCACAG GGCCAATTTC    240
TCATGCCTCG CGGAGCTTGA CCTGCGGCCA CACGGCTTGG GACTGTTTGC AAACAGCTCA    300
GCCCCAGAC AGCTCCGCAC GTTTGCCATG CCTCCACTTT CCCCGAGCCT TATTGCCCCA     360
CGATTCTTAG AAGTGGGCTC AGAAAGGCCG GTGACTTGCA CTTTGGATGG ACTGTTTCCT    420
GCCCCAGAAG CCGGGGTTTA CCTCTCTCTG GGAGATCAGA GGCTTCATCC TAATGTGACC    480
CTCGACGGGG AGAGCCTTGT GGCCACTGCC ACAGCTACAG CAAGTGAAGA ACAGGAAGGC    540
ACCAAACAGC TGATGTGCAT CGTGACCCTC GGGGCGAAA GCAGGGAGAC CCAGGAAAAC     600
CTGACTGTCT ACAGCTTCCC GGCTCCTCTT CTGACTTTAA GTGAGCCAGA AGCCCCGAG     660
GGAAAGATGG TGACCGTAAG CTGCTGGGCA GGGGCCCGAG CCCTTGTCAC CTTGGAGGGA    720
ATTCCAGCTG CGGTCCCTGG GCAGCCCGCT GAGCTCCAGT TAAATGTCAC AAAGAATGAC    780
GACAAGCGGG GCTTCTTCTG CGACGCTGCC CTCGATGTGG ACGGGGAAAC TCTGAGAAAG    840
AACCAGAGCT CTGAGCTTCG TGTTCTGTGT GAGTGGATGT TCACTTTATC TCTGTGAATT    900
CCAAGGACCC TCTTACCGGC CCATCTTTA ACCTTATCGT ATCCCTCTG CCTCATGCCC      960
GCAGACGCAC CTCGGCTGGA TGACTTGGAC TGTCCCAGGA GCTGGACGTG GCCAGAGGGT    1020
CCAGAGCAGA CCCTCCACTG CGAGGCCCGT GGAAACCCTG AGCCCTCCGT GCACTGTGCA    1080
AGGCCTGACG GTGGGGCGGT GCTAGCGCTG GGCCTGTTGG GTCCAGTGAC CCGTGCCCTC    1140
```

| | | | | | |
|---|---|---|---|---|---|
| GCGGGCACTT | ACCGATGTAC | AGCAATCAAT | GGGCAAGGCC | AGGCGGTCAA | GGATGTGACC | 1200 |
| CTGACTGTGG | AATATGCCCC | AGCGCTGGAC | AGTGTAGGCT | GCCCAGAACG | TATTACTTGG | 1260 |
| CTGGAGGGGA | CAGAGGCATC | GCTTAGCTGT | GTGGCACACG | GGGTCCCACC | ACCTAGCGTG | 1320 |
| AGCTGTGTGC | GCTCTGGAAA | GGAGGAAGTC | ATGGAAGGGC | CCCTGCGTTT | GGCCGGGAG | 1380 |
| CACGCTGGCA | CTTACCGATG | CGAAGCCATC | AACGCCAGGG | GATCAGCGGC | CAAAAATGTG | 1440 |
| GCTGTCACGG | TGGAATATGG | TCCCCGGAAT | TC | | | 1472 |

( 2 ) INFORMATION FOR SEQ ID NO:10:

( i ) SEQUENCE CHARACTERISTICS:
        ( A ) LENGTH: 2550 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | | | | | |
|---|---|---|---|---|---|
| CCTCTGCCTC | CTTGGCAGCC | TGTAGGTGAG | AACTTCACCT | TGAGCTGCAG | GGTCCCGGGG | 60 |
| GCAGGACCCC | GAGCGAGCCT | CACATTGACC | TTGCTGCGAG | GCGGCCAGGA | GCTGATTCGC | 120 |
| CGAAGTTTCG | TAGGCGAGCC | ACCCCGAGCT | CGGGGTGCGA | TGCTCACCGC | CACGGTCCTG | 180 |
| GCGCGCAGAG | AGGATCACAG | GGCCAATTTC | TCATGCCTCG | GGAGCTTGA | CCTGCGGCCA | 240 |
| CACGGCTTGG | GACTGTTTGC | AAACAGCTCA | GCCCCAGAC | AGCTCCGCAC | GTTTGCCATG | 300 |
| CCTCCACTTT | CCCCGAGCCT | TATTGCCCCA | CGATTCTTAG | AAGTGGGCTC | AGAAAGGCCG | 360 |
| GTGACTTGCA | CTTTGGATGG | ACTGTTTCCT | GCCCCAGAAG | CCGGGGTTTA | CCTCTCTCTG | 420 |
| GGAGATCAGA | GGCTTCATCC | TAATGTGACC | CTCGACGGGG | AGAGCCTTGT | GGCCACTGCC | 480 |
| ACAGCTACAG | CAAGTGAAGA | ACAGGAAGGC | ACCAAACAGC | TGATGTGCAT | CGTGACCCTC | 540 |
| GGGGGCGAAA | GCAGGGAGAC | CCAGGAAAAC | CTGACTGTCT | ACAGCTTCCC | GGCTCCTCTT | 600 |
| CTGACTTTAA | GTGAGCCAGA | AGCCCCCGAG | GGAAAGATGG | TGACCGTAAG | CTGCTGGGCA | 660 |
| GGGGCCCGAG | CCCTTGTCAC | CTTGGAGGGA | ATTCCAGCTG | CGGTCCCTGG | GCAGCCCGCT | 720 |
| GAGCTCCAGT | TAAATGTCAC | AAAGAATGAC | GACAAGCGGG | GCTTCTTCTG | CGACGCTGCC | 780 |
| CTCGATGTGG | ACGGGGAAAC | TCTGAGAAAG | AACCAGAGCT | CTGAGCTTCG | TGTTCTGTAC | 840 |
| GCACCTCGGC | TGGATGACTT | GGACTGTCCC | AGGAGCTGGA | CGTGGCCAGA | GGGTCCAGAG | 900 |
| CAGACCCTCC | ACTGCGAGGC | CCGTGGAAAC | CCTGAGCCCT | CCGTGCACTG | TGCAAGGCCT | 960 |
| GACGGTGGGG | CGGTGCTAGC | GCTGGGCCTG | TTGGGTCCAG | TGACCCGTGC | CCTCGCGGGC | 1020 |
| ACTTACCGAT | GTACAGCAAT | CAATGGGCAA | GGCCAGGCGG | TCAAGGATGT | GACCCTGACT | 1080 |
| GTGGAATATG | CCCCAGCGCT | GGACAGTGTA | GGCTGCCCAG | AACGTATTAC | TTGGCTGGAG | 1140 |
| GGGACAGAGG | CATCGCTTAG | CTGTGTGGCA | CACGGGGTCC | CACCACCTAG | CGTGAGCTGT | 1200 |
| GTGCGCTCTG | GAAAGGAGGA | AGTCATGGAA | GGGCCCCTGC | GTGTGGCCCG | GAGCACGCT | 1260 |
| GGCACTTACC | GATGCGAAGC | CATCAACGCC | AGGGGATCAG | CGGCCAAAAA | TGTGGCTGTC | 1320 |
| ACGGTGGAAT | ATGGTCCCAG | TTTTGAGGAG | TTGGGCTGCC | CCAGCAACTG | GACTTGGGTA | 1380 |
| GAAGGATCTG | GAAAACTGTT | TTCCTGTGAA | GTTGATGGGA | AGCCGGAACC | ACGCGTGGAG | 1440 |
| TGCGTGGGCT | CGGAGGGTGC | AAGCGAAGGG | GTAGTGTTGC | CCCTGGTGTC | CTCGAACTCT | 1500 |
| GGTTCCAGAA | ACTCTATGAC | TCCTGGTAAC | CTGTCACCGG | GTATTTACCT | CTGCAACGCC | 1560 |
| ACCAACCGGC | ATGGCTCCAC | AGTCAAAACA | GTCGTCGTGA | GCGCGGAATC | ACCGCCACAG | 1620 |
| ATGGATGAAT | CCAGTTGCCC | GAGTCACCAG | ACATGGCTGG | AAGGAGCCGA | GGCTACTGCG | 1680 |

```
CTGGCCTGCA  GTGCCAGAGG  CCGCCCCTCT  CCACGCGTGC  GCTGTTCCAG  GGAAGGTGCA    1740

GCCAGGCTGG  AGAGGCTACA  GGTGTCCCGA  GAGGATGCGG  GGACCTACCT  GTGTGTGGCT    1800

ACCAACGCGC  ATGGCACGGA  TTCACGGACC  GTCACTGTGG  GTGTGGAATA  CCGGCCTGTG    1860

GTGGCTGAGC  TGGCAGCCTC  GCCCCAAGC   GTGCGGCCTG  GCGGAAACTT  CACTCTGACC    1920

TGCCGTGCAG  AGGCCTGGCC  TCCAGCCCAG  ATCAGCTGGC  GCGCGCCCCC  GGGAGCTCTC    1980

AACCTCGGTC  TCTCCAGCAA  CAACAGCACG  CTGAGCGTGG  CGGGTGCCAT  GGGCAGCCAT    2040

GGTGGCGAGT  ATGAGTGCGC  AGCCACCAAT  GCGCATGGGC  GCCACGCACG  GCGCATCACG    2100

GTGCGCGTGG  CCGGTCCATG  GCTGTGGGTC  GCTGTGGGCG  GTGCGGCAGG  GGGCGCGGCG    2160

CTGCTGGCCG  CAGGGGCCGG  CCTGGCCTTC  TACGTGCAGT  CCACCGCTTG  CAAGAAGGGA    2220

GAGTACAACG  TCCAGGAGGC  TGAGAGCTCA  GGCGAGGCGG  TGTGTCTCAA  TGGCGCGGGC    2280

GGGACACCGG  GTGCAGAAGG  CGGAGCAGAG  ACCCCCGGCA  CTGCCGAGTC  ACCTGCAGAT    2340

GGCGAGGTTT  TCGCCATCCA  GCTGACATCT  TCCTGAGCCT  GTATCCAGCT  CCCCCAGGGG    2400

CCTCGAAAGC  ACAGGGGTGG  ACGTATGTAT  TGTTCACTCT  CTATTTATTC  AACTCCAGGG    2460

GCGTCGTCCC  CGTTTCTAC   CCATTCCCTT  AATAAAGTTT  TTATAGGAGA  AAAAAAAAA    2520

AAAAAAAAAA  AAAAAAAAAA  AAAAAAAAA                                       2550
```

( 2 ) INFORMATION FOR SEQ ID NO:11:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
AATTCGATCA  CTCGCGCTCC  CCTCGCCTTC  TGCGCTCTCC  CCTCCCTGGC  AGCGGCGGCA     60

ATGCCGGGGC  CTTCACCAGG  GCTGCGCCGA  ACGCTCCTCG  GCCTCTGGGC  TGCCCTGGGC    120

CTGGGGATCC  TAGGCATCTC  AGCGGTCGCG  CTAGAACCTT  TCTGGGCGGA  CCTTCAGCCC    180

CGCGTGGCGC  TCGTGGAGCG  CGGGGGCTCG  CTGTGGCTCA  AC                        222
```

( 2 ) INFORMATION FOR SEQ ID NO:12:

( i ) SEQUENCE CHARACTERISTICS:
        ( A ) LENGTH: 292 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
TGTGGAGCTG  GCACCCCTGC  CTCCTTGGCA  GCCGGTGGGC  CAGAACTTCA  CCCTGCGCTG     60

CCAAGTGGAG  GGTGGGTCGC  CCCGGACCAG  CCTCACGGTG  GTGCTGCTTC  GCTGGGAGGA    120

GGAGCTGAGC  CGGCAGCCCG  CAGTGGAGGA  GCCAGCGGAG  GTCACTGCCA  CTGTGCTGGC    180

CAGCAGAGAC  GACCACGGAG  CCCCTTTCTC  ATGCCGCACA  GAACTGGACA  TGCAGCCCCA    240

GGGGCTGGGA  CTGTTCGTGA  ACACCTCAGC  CCCCGCCAG   CTCCGAACCT  TT            292
```

( 2 ) INFORMATION FOR SEQ ID NO:13:

( i ) SEQUENCE CHARACTERISTICS:
        ( A ) LENGTH: 105 amino acids ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

Pro Asp Arg Val Glu Leu Val Pro Leu Pro Pro Trp Gln Pro Val Gly
 1               5                  10                  15

Glu Asn Phe Thr Leu Ser Cys Arg Val Pro Gly Ala Gly Pro Arg Ala
                20                  25                  30

Ser Leu Thr Leu Thr Leu Leu Arg Gly Gly Gln Glu Leu Ile Arg Arg
            35                  40                  45

Ser Phe Val Gly Glu Pro Pro Arg Ala Arg Cys Ala Met Leu Thr Ala
        50                  55                  60

Thr Val Leu Ala Arg Arg Glu Asp His Arg Asp Asn Phe Ser Cys Leu
 65                  70                  75                  80

Ala Glu Leu Asp Leu Arg Thr His Gly Leu Gly Leu Phe Ala Asn Ser
                85                  90                  95

Ser Ala Pro Arg Gln Leu Arg Thr Phe
                100                 105

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GAACTCGAGG CCATGCCTCC ACTTTCC                                                   27

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CCATAAGCTT TATTCCACCG TGACAGCCAC                                                30

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

AACGTGCGGA GCTGTCTG                                                             18

( 2 ) INFORMATION FOR SEQ ID NO:17:

( i ) SEQUENCE CHARACTERISTICS:
        ( A ) LENGTH: 27 base pairs
        ( B ) TYPE: nucleic acid ( C ) STRANDEDNESS: single
        ( D ) TOPOLOGY: linear ( i i ) MOLECULE TYPE: cDNA ( x i ) SEQUENCE DESCRIPTION: SEQ ID NO:17:

ACGGAATTCG AAGCCATCAA CGCCAGG                27

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CATGAATTCC GAATCTTGAG TGGGATG                27

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

ATAGAATTCC TCGGGACACC TGTAGCC                27

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

CARGGTGACA AGGGCTCG                18

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

TATGAATTCA GTTGAGCCAC AGCGAGC                27

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA

5,702,917

63                                64

-continued ( x i ) SEQUENCE DESCRIPTION: SEQ ID NO:22:

```
CCGGGTCCTA GAGGTGGACA CGCA                                              24
```

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
TGCAGTGTCT CCTGGCTCTG GTTC                                              24
```

( 2 ) INFORMATION FOR SEQ ID NO:24:

( i ) SEQUENCE CHARACTERISTICS:
        ( A ) LENGTH: 992 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
GCGAAAACCG GGAGACCCGG GAGAACGTGA CCATCTACAG CTTCCCGGCA CCACTCCTGA        60
CCCTGAGCGA ACCCAGCGTC TCCGAGGGGC AGATGGTGAC AGTAACCTGC GCAGCTGGGG       120
CCCAAGCTCT GGTCACACTG GAGGGAGTTC CAGCCGCGGT CCCGGGGCAG CCCGCCCAGC       180
TTCAGCTAAA TGCCACCGAG AACGACGACA GACGCAGCTT CTTCTGCGAC GCCACCCTCG       240
ATGTGGACGG GGAGACCCTG ATCAAGAACA GGAGCGCAGA GCTTCGTGTC CTATACGCTC       300
CCCGGCTAGA CGATTCGGAC TGCCCCAGGA GTTGGACGTG GCCCGAGGGC CAGAGCAGA        360
CGCTGCGCTG CGAGGCCCGC GGGAACCCAG AACCCTCAGT GCACTGTGCG CGCTCCGACG       420
GCGGGGCCGT GCTGGCTCTG GGCCTGCTGG GTCCAGTCAC TCGGGCGCTC TCAGGCACTT       480
ACCGCTGCAA GGCGGCCAAT GATCAAGGCG AGGCGGTCAA GGACGTAACG CTAACGGTGG       540
AGTACGCACC AGCGCTGGAC AGCGTGGGCT GCCCAGAACG CATTACTTGG CTGGAGGGAA       600
CAGAAGCCTC GCTGAGCTGT GTGGCGCACG GGTACCGCC GCCTGATGTG ATCTGCGTGC        660
GCTCTGGAGA ACTCGGGGCC GTCATCGAGG GGCTGTTGCG TGTGGCCCGG GAGCATGCGG       720
GCACTTACCG CTGCGAAGCC ACCAACCCTC GGGGCTCTGC GGCCAAAAAT GTGGCCGTCA       780
CGGTGGAATA TGGCCCCAGG TTTGAGGAGC CGAGCTGCCC CAGCAATTGG ACATGGGTGG       840
AAGGATCTGG GCGCCTGTTT TCCTGTGAGG TCGATGGGAA GCCACAGCCA AGCGTGAAGT       900
GCGTGGGCTC CGGGGCACC ACTGAGGGGG TGCTGCTGCC GCTGGCACCC CCAGACCCTA        960
GTCCAGAGC TCCCAGAATC CCTAGAGTCC TG                                      992
```

( 2 ) INFORMATION FOR SEQ ID NO:25:

( i ) SEQUENCE CHARACTERISTICS:
        ( A ) LENGTH: 2775 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
GCAGCCTCGC GTGGCGTTCG TGGAGCGCGG GGGCTCGCTG TGGCTGAATT GCAGCACCAA        60
```

| | | | | | |
|---|---|---|---|---|---|
|CTGCCCTCGG|CCGGAGCGCG|GTGGCCTGGA|GACCTCGCTG|CGCCGAAACG|GGACCCAGAG|120
|GGGTTTGCGT|TGGTTGGCGC|GGCAGCTGGT|GGACATTCGC|GAGCCGGAGA|CTCAGCCCGT|180
|CTGCTTCTTC|CGCTGCGCGC|GGCGCACACT|ACAGGCGCGT|GGGCTCATTC|GCACTTTCCA|240
|GCGACCAGAT|CGCGTAGAGC|TGATGCCGCT|GCCTCCCTGG|CAGCCGGTGG|GCGAGAACTT|300
|CACCCTGAGC|TGTAGGGTCC|CCGGCGCCGG|GCCCCGTGCG|AGCCTCACGC|TGACCCTGCT|360
|GCGGGGCGCC|CAGGAGCTGA|TCCGCCGCAG|CTTCGCCGGT|GAACCACCCC|GAGCGCGGGG|420
|CGCGGTGCTC|ACAGCCACGG|TACTGGCTCG|GAGGGAGGAC|CATGGAGCCA|ATTTCTCGTG|480
|TCGCGCCGAG|CTGGACCTGC|GGCCGCACGG|ACTGGGACTG|TTTGAAAACA|GCTCGGCCCC|540
|CAGAGAGCTC|CGAACCTTCT|CCCTGTCTCC|GGATGCCCCG|CGCCTCGCTG|CTCCCCGGCT|600
|CTTGGAAGTT|GGCTCGGAAA|GGCCCGTGAG|CTGCACTCTG|GACGGACTGT|TTCCAGCCTC|660
|AGAGGCCAGG|GTCTACCTCG|CACTGGGGGA|CCAGAATCTG|AGTCCTGATG|TCACCCTCGA|720
|AGGGGACGCA|TTCGTGGCCA|CTGCCACAGC|CACAGCTAGC|GCAGAGCAGG|AGGGTGCCAG|780
|GCAGCTGGTC|TGCAACGTCA|CCCTGGGGGG|CGAAAACCGG|GAGACCCGGG|AGAACGTGAC|840
|CATCTACAGC|TTCCCGGCAC|CACTCCTGAC|CCTGAGCGAA|CCCAGCGTCT|CCGAGGGGCA|900
|GATGGTGACA|GTAACCTGCG|CAGCTGGGGC|CCAAGCTCTG|GTCACACTGG|AGGGAGTTCC|960
|AGCCGCGGTC|CCGGGGCAGC|CCGCCCAGCT|TCAGCTAAAT|GCCACCGAGA|ACGACGACAG|1020
|ACGCAGCTTC|TTCTGCGACG|CCACCCTCGA|TGTGGACGGG|GAGACCCTGA|TCAAGAACAG|1080
|GAGCGCAGAG|CTTCGTGTCC|TATACGCTCC|CCGGCTAGAC|GATTCGGACT|GCCCCAGGAG|1140
|TTGGACGTGG|CCCGAGGGCC|CAGAGCAGAC|GCTGCGCTGC|GAGGCCCGCG|GAACCCAGA|1200
|ACCCTCAGTG|CACTGTGCGC|GCTCCGACGG|CGGGGCCGTG|CTGGCTCTGG|GCCTGCTGGG|1260
|TCCAGTCACT|CGGGCGCTCT|CAGGCACTTA|CCGCTGCAAG|GCGGCCAATG|ATCAAGGCGA|1320
|GGCGGTCAAG|GACGTAACGC|TAACGGTGGA|GTACGCACCA|GCGCTGGACA|GCGTGGGCTG|1380
|CCCAGAACGC|ATTACTTGGC|TGGAGGGAAC|AGAAGCCTCG|CTGAGCTGTG|TGGCGCACGG|1440
|GGTACCGCCG|CCTGATGTGA|TCTGCGTGCG|CTCTGGAGAA|CTCGGGGCCG|TCATCGAGGG|1500
|GCTGTTGCGT|GTGGCCCGGG|AGCATGCGGG|CACTTACCGC|TGCGAAGCCA|CCAACCCTCG|1560
|GGGCTCTGCG|GCCAAAAATG|TGGCCGTCAC|GGTGGAATAT|GGCCCCAGGT|TTGAGGAGCC|1620
|GAGCTGCCCC|AGCAATTGGA|CATGGGTGGA|AGGATCTGGG|CGCCTGTTTT|CCTGTGAGGT|1680
|CGATGGGAAG|CCACAGCCAA|GCGTGAAGTG|CGTGGGCTCC|GGGGGCACCA|CTGAGGGGGT|1740
|GCTGCTGCCG|CTGGCACCCC|CAGACCCTAG|TCCAGAGCT|CCCAGAATCC|CTAGAGTCCT|1800
|GGCACCCGGT|ATCTACGTCT|GCAACGCCAC|CAACCGCCAC|GGCTCCGTGG|CCAAAACAGT|1860
|CGTCGTGAGC|GCGGAGTCGC|CACCGGAGAT|GGATGAATCT|ACCTGCCCAA|GTCACCAGAC|1920
|GTGGCTGGAA|GGGGCTGAGG|CTTCCGCGCT|GGCCTGCGCC|GCCCGGGGTC|GCCCTTCCCC|1980
|AGGAGTGCGC|TGCTCTCGGG|AAGGCATCCC|ATGGCCTGAG|CAGCAGCGCG|TGTCCCGAGA|2040
|GGACGCGGGC|ACTTACCACT|GTGTGGCCAC|CAATGCGCAT|GGCACGGACT|CCCGGACCGT|2100
|CACTGTGGGC|GTGGAATACC|GGCCAGTGGT|GGCCGAACTT|GCTGCCTCGC|CCCCTGGAGG|2160
|CGTGCGCCCA|GGAGGAAACT|TCACGTTGAC|CTGCCGCGCG|GAGGCCTGGC|CTCCAGCCCA|2220
|GATCAGCTGG|CGCGCGCCCC|CGAGGGCCCT|CAACATCGGC|CTGTCGAGCA|ACAACAGCAC|2280
|ACTGAGCGTG|GCAGGCGCCA|TGGAAGCCA|CGGCGGCGAG|TACGAGTGCG|CACGCACCAA|2340
|CGCGCACGGG|CGCCACGCGC|GGCGCATCAC|GGTGCGCGTG|GCCGGTCCGT|GGCTATGGGT|2400
|CGCCGTGGGC|GGCGCGGCGG|GGGCGCGGC|GCTGCTGGCC|GCGGGGCCG|GCCTGGCCTT|2460

| | | | | | |
|---|---|---|---|---|---|
| CTACGTGCAG | TCCACCGCCT | GCAAGAAGGG | CGAGTACAAC | GTGCAGGAGG | CCGAGAGCTC | 2520 |
| AGGCGAGGCC | GTGTGTCTGA | ACGGAGCGGG | CGGCGGCGCT | GGCGGGGCGG | CAGGCGCGGA | 2580 |
| GGGCGGACCC | GAGGCGGCGG | GGGGCGCGGC | CGAGTCGCCG | GCGGAGGGCG | AGGTCTTCGC | 2640 |
| CATACAGCTG | ACATCGGCGT | GAGCCCGCTC | CCCTCTCCGC | GGGCCGGGAC | GCCCCCCAGA | 2700 |
| CTCACACGGG | GGCTTATTTA | TTGCTTTATT | TATTTACTTA | TTCATTTATT | TATGTATTCA | 2760 |
| ACTCCAAGGG | AATTC | | | | | 2775 |

( 2 ) INFORMATION FOR SEQ ID NO:26:

( i ) SEQUENCE CHARACTERISTICS:
        ( A ) LENGTH: 1557 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

| | | | | | |
|---|---|---|---|---|---|
| CGCGCTCTCC | TCGCCTCCTG | TGCTTTCCCC | GCCGCGGCGA | TGCCAGGGCC | TTCGCCAGGG | 60 |
| CTGCGCCGGG | CGCTACTCGG | CCTCTGGGCT | GCTCTGGGCC | TGGGGCTCTT | CGGCCTCTCA | 120 |
| GCGGTCTCGC | AGGAGCCCTT | CTGGGCGGAC | CTGCAGCCTC | GCGTGGCGTT | CGTGGAGCGC | 180 |
| GGGGGCTCGC | TGTGGCTGAA | TTGCAGCACC | AACTGCCCTC | GGCCGGAGCG | CGGTGGCCTG | 240 |
| GAGACCTCGC | TGCGCCGAAA | CGGGACCCAG | AGGGGTTTGC | GTTGGTTGGC | GCGGCAGCTG | 300 |
| GTGGACATTC | GCGAGCCGGA | GACTCAGCCC | GTCTGCTTCT | TCCGCTGCGC | GCGGCGCACA | 360 |
| CTACAGGCGC | GTGGGCTCAT | TCGCACTTTC | CAGCGACCAG | ATCGCGTAGA | GCTGATGCCG | 420 |
| CTGCCTCCCT | GGCAGCCGGT | GGGCGAGAAC | TTCACCCTGA | GCTGTAGGGT | CCCCGGCGCC | 480 |
| GGGCCCCGTG | CGAGCCTCAC | GCTGACCCTG | CTGCGGGGCG | CCCAGGAGCT | GATCCGCCGC | 540 |
| AGCTTCGCCG | GTGAACCACC | CCGAGCGCGG | GGCGCGGTGC | TCACAGCCAC | GGTACTGGCT | 600 |
| CGGAGGGAGG | ACCATGGAGC | CAATTTCTCG | TGTCGCGCCG | AGCTGGACCT | GCGGCCGCAC | 660 |
| GGACTGGGAC | TGTTTGAAAA | CAGCTCGGCC | CCAGAGAGC | TCCGAACCTT | CTCCCTGTCT | 720 |
| CCGGATGCCC | CGCGCCTCGC | TGCTCCCCGG | CTCTTGGAAG | TTGGCTCGGA | AAGGCCCGTG | 780 |
| AGCTGCACTC | TGGACGGACT | GTTTCCAGCC | TCAGAGGCCA | GGGTCTACCT | CGCACTGGGG | 840 |
| GACCAGAATC | TGAGTCCTGA | TGTCACCCTC | GAAGGGACG | CATTCGTGGC | CACTGCCACA | 900 |
| GCCACAGCTA | GCGCAGAGCA | GGAGGGTGCC | AGGCAGCTGG | TCTGCAACGT | CACCCTGGGG | 960 |
| GGCGAAAACC | GGGAGACCCG | GGAGAACGTG | ACCATCTACA | GCTTCCCGGC | ACCACTCCTG | 1020 |
| ACCCTGAGCG | AACCCAGCGT | CTCCGAGGGG | CAGATGGTGA | CAGTAACCTG | CGCAGCTGGG | 1080 |
| GCCCAAGCTC | TGGTCACACT | GGAGGGAGTT | CCAGCCGCGG | TCCCGGGGCA | GCCCGCCCAG | 1140 |
| CTTCAGCTAA | ATGCCACCGA | GAACGACGAC | AGACGCAGCT | TCTTCTGCGA | CGCCACCCTC | 1200 |
| GATGTGGACG | GGAGACCCT | GATCAAGAAC | AGGAGCGCAG | AGCTTCGTGT | CCTATACGCT | 1260 |
| CCCCGGCTAG | ACGATTCGGA | CTGCCCCAGG | AGTTGGACGT | GGCCCGAGGG | CCCAGAGCAG | 1320 |
| ACGCTGCGCT | GCGAGGCCCG | CGGGAACCCA | GAACCCTCAG | TGCACTGTGC | GCGCTCCGAC | 1380 |
| GGCGGGGCCG | TGCTGGCTCT | GGGCCTGCTG | GGTCCAGTCA | CTCGGGCGCT | CTCAGGCACT | 1440 |
| TACCGCTGCA | AGGCGGCCAA | TGATCAAGGC | GAGGCGGTCA | AGGACGTAAC | GCTAACGGTG | 1500 |
| GAGTACGCAC | CAGCGCTGGA | CAGCGTGGGC | TGCCCAGAAC | GCATTACTTG | GCTGGAG | 1557 |

( 2 ) INFORMATION FOR SEQ ID NO:27:

(i) SEQUENCE CHARACTERISTICS:
    (A) LENGTH: 2927 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 40..2814

(xi) SEQUENCE DESCRIPTION: SEQ ID NO:27:

```
CGCGCTCTCC TCGCCTCCTG TGCTTTCCCC GCCGCGGCG ATG CCA GGG CCT TCG        54
                                            Met Pro Gly Pro Ser
                                            1               5

CCA GGG CTG CGC CGG GCG CTA CTC GGC CTC TGG GCT GCT CTG GGC CTG      102
Pro Gly Leu Arg Arg Ala Leu Leu Gly Leu Trp Ala Ala Leu Gly Leu
            10                  15                  20

GGG CTC TTC GGC CTC TCA GCG GTC TCG CAG GAG CCC TTC TGG GCG GAC      150
Gly Leu Phe Gly Leu Ser Ala Val Ser Gln Glu Pro Phe Trp Ala Asp
        25                  30                  35

CTG CAG CCT CGC GTG GCG TTC GTG GAG CGC GGG GGC TCG CTG TGG CTG      198
Leu Gln Pro Arg Val Ala Phe Val Glu Arg Gly Gly Ser Leu Trp Leu
    40                  45                  50

AAT TGC AGC ACC AAC TGC CCT CGG CCG GAG CGC GGT GGC CTG GAG ACC      246
Asn Cys Ser Thr Asn Cys Pro Arg Pro Glu Arg Gly Gly Leu Glu Thr
55                  60                  65

TCG CTG CGC CGA AAC GGG ACC CAG AGG GGT TTG CGT TGG TTG GCG CGG      294
Ser Leu Arg Arg Asn Gly Thr Gln Arg Gly Leu Arg Trp Leu Ala Arg
70                  75                  80                  85

CAG CTG GTG GAC ATT CGC GAG CCG GAG ACT CAG CCC GTC TGC TTC TTC      342
Gln Leu Val Asp Ile Arg Glu Pro Glu Thr Gln Pro Val Cys Phe Phe
                90                  95                 100

CGC TGC GCG CGG CGC ACA CTA CAG GCG CGT GGG CTC ATT CGC ACT TTC      390
Arg Cys Ala Arg Arg Thr Leu Gln Ala Arg Gly Leu Ile Arg Thr Phe
            105                 110                 115

CAG CGA CCA GAT CGC GTA GAG CTG ATG CCG CTG CCT CCC TGG CAG CCG      438
Gln Arg Pro Asp Arg Val Glu Leu Met Pro Leu Pro Pro Trp Gln Pro
        120                 125                 130

GTG GGC GAG AAC TTC ACC CTG AGC TGT AGG GTC CCC GGC GCC GGG CCC      486
Val Gly Glu Asn Phe Thr Leu Ser Cys Arg Val Pro Gly Ala Gly Pro
135                 140                 145

CGT GCG AGC CTC ACG CTG ACC CTG CTG CGG GGC GCC CAG GAG CTG ATC      534
Arg Ala Ser Leu Thr Leu Thr Leu Leu Arg Gly Ala Gln Glu Leu Ile
150                 155                 160                 165

CGC CGC AGC TTC GCC GGT GAA CCA CCC CGA GCG CGG GGC GCG GTG CTC      582
Arg Arg Ser Phe Ala Gly Glu Pro Pro Arg Ala Arg Gly Ala Val Leu
            170                 175                 180

ACA GCC ACG GTA CTG GCT CGG AGG GAG GAC CAT GGA GCC AAT TTC TCG      630
Thr Ala Thr Val Leu Ala Arg Arg Glu Asp His Gly Ala Asn Phe Ser
        185                 190                 195

TGT CGC GCC GAG CTG GAC CTG CGG CCG CAC GGA CTG GGA CTG TTT GAA      678
Cys Arg Ala Glu Leu Asp Leu Arg Pro His Gly Leu Gly Leu Phe Glu
    200                 205                 210

AAC AGC TCG GCC CCC AGA GAG CTC CGA ACC TTC TCC CTG TCT CCG GAT      726
Asn Ser Ser Ala Pro Arg Glu Leu Arg Thr Phe Ser Leu Ser Pro Asp
215                 220                 225

GCC CCG CGC CTC GCT GCT CCC CGG CTC TTG GAA GTT GGC TCG GAA AGG      774
Ala Pro Arg Leu Ala Ala Pro Arg Leu Leu Glu Val Gly Ser Glu Arg
230                 235                 240                 245

CCC GTG AGC TGC ACT CTG GAC GGA CTG TTT CCA GCC TCA GAG GCC AGG      822
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Pro | Val | Ser | Cys | Thr | Leu | Asp | Gly | Leu | Phe | Pro | Ala | Ser | Glu | Ala | Arg |      |
|     |     |     |     | 250 |     |     |     | 255 |     |     |     |     | 260 |     |     |      |
| GTC | TAC | CTC | GCA | CTG | GGG | GAC | CAG | AAT | CTG | AGT | CCT | GAT | GTC | ACC | CTC | 870  |
| Val | Tyr | Leu | Ala | Leu | Gly | Asp | Gln | Asn | Leu | Ser | Pro | Asp | Val | Thr | Leu |      |
|     |     |     | 265 |     |     |     | 270 |     |     |     |     | 275 |     |     |     |      |
| GAA | GGG | GAC | GCA | TTC | GTG | GCC | ACT | GCC | ACA | GCC | ACA | GCT | AGC | GCA | GAG | 918  |
| Glu | Gly | Asp | Ala | Phe | Val | Ala | Thr | Ala | Thr | Ala | Thr | Ala | Ser | Ala | Glu |      |
|     |     | 280 |     |     |     |     | 285 |     |     |     |     | 290 |     |     |     |      |
| CAG | GAG | GGT | GCC | AGG | CAG | CTG | GTC | TGC | AAC | GTC | ACC | CTG | GGG | GGC | GAA | 966  |
| Gln | Glu | Gly | Ala | Arg | Gln | Leu | Val | Cys | Asn | Val | Thr | Leu | Gly | Gly | Glu |      |
|     | 295 |     |     |     |     | 300 |     |     |     |     | 305 |     |     |     |     |      |
| AAC | CGG | GAG | ACC | CGG | GAG | AAC | GTG | ACC | ATC | TAC | AGC | TTC | CCG | GCA | CCA | 1014 |
| Asn | Arg | Glu | Thr | Arg | Glu | Asn | Val | Thr | Ile | Tyr | Ser | Phe | Pro | Ala | Pro |      |
| 310 |     |     |     |     | 315 |     |     |     |     | 320 |     |     |     |     | 325 |      |
| CTC | CTG | ACC | CTG | AGC | GAA | CCC | AGC | GTC | TCC | GAG | GGG | CAG | ATG | GTG | ACA | 1062 |
| Leu | Leu | Thr | Leu | Ser | Glu | Pro | Ser | Val | Ser | Glu | Gly | Gln | Met | Val | Thr |      |
|     |     |     |     |     | 330 |     |     |     |     | 335 |     |     |     |     | 340 |      |
| GTA | ACC | TGC | GCA | GCT | GGG | GCC | CAA | GCT | CTG | GTC | ACA | CTG | GAG | GGA | GTT | 1110 |
| Val | Thr | Cys | Ala | Ala | Gly | Ala | Gln | Ala | Leu | Val | Thr | Leu | Glu | Gly | Val |      |
|     |     |     | 345 |     |     |     | 350 |     |     |     |     | 355 |     |     |     |      |
| CCA | GCC | GCG | GTC | CCG | GGG | CAG | CCC | GCC | CAG | CTT | CAG | CTA | AAT | GCC | ACC | 1158 |
| Pro | Ala | Ala | Val | Pro | Gly | Gln | Pro | Ala | Gln | Leu | Gln | Leu | Asn | Ala | Thr |      |
|     |     | 360 |     |     |     |     | 365 |     |     |     |     | 370 |     |     |     |      |
| GAG | AAC | GAC | GAC | AGA | CGC | AGC | TTC | TTC | TGC | GAC | GCC | ACC | CTC | GAT | GTG | 1206 |
| Glu | Asn | Asp | Asp | Arg | Arg | Ser | Phe | Phe | Cys | Asp | Ala | Thr | Leu | Asp | Val |      |
|     | 375 |     |     |     |     | 380 |     |     |     |     | 385 |     |     |     |     |      |
| GAC | GGG | GAG | ACC | CTG | ATC | AAG | AAC | AGG | AGC | GCA | GAG | CTT | CGT | GTC | CTA | 1254 |
| Asp | Gly | Glu | Thr | Leu | Ile | Lys | Asn | Arg | Ser | Ala | Glu | Leu | Arg | Val | Leu |      |
| 390 |     |     |     |     | 395 |     |     |     |     | 400 |     |     |     |     | 405 |      |
| TAC | GCT | CCC | CGG | CTA | GAC | GAT | TCG | GAC | TGC | CCC | AGG | AGT | TGG | ACG | TGG | 1302 |
| Tyr | Ala | Pro | Arg | Leu | Asp | Asp | Ser | Asp | Cys | Pro | Arg | Ser | Trp | Thr | Trp |      |
|     |     |     |     | 410 |     |     |     |     | 415 |     |     |     |     | 420 |     |      |
| CCC | GAG | GGC | CCA | GAG | CAG | ACG | CTG | CGC | TGC | GAG | GCC | CGC | GGG | AAC | CCA | 1350 |
| Pro | Glu | Gly | Pro | Glu | Gln | Thr | Leu | Arg | Cys | Glu | Ala | Arg | Gly | Asn | Pro |      |
|     |     |     | 425 |     |     |     |     | 430 |     |     |     |     | 435 |     |     |      |
| GAA | CCC | TCA | GTG | CAC | TGT | GCG | CGC | TCC | GAC | GGC | GGG | GCC | GTG | CTG | GCT | 1398 |
| Glu | Pro | Ser | Val | His | Cys | Ala | Arg | Ser | Asp | Gly | Gly | Ala | Val | Leu | Ala |      |
|     |     | 440 |     |     |     |     | 445 |     |     |     |     | 450 |     |     |     |      |
| CTG | GGC | CTG | CTG | GGT | CCA | GTC | ACT | CGG | GCG | CTC | TCA | GGC | ACT | TAC | CGC | 1446 |
| Leu | Gly | Leu | Leu | Gly | Pro | Val | Thr | Arg | Ala | Leu | Ser | Gly | Thr | Tyr | Arg |      |
|     | 455 |     |     |     |     | 460 |     |     |     |     | 465 |     |     |     |     |      |
| TGC | AAG | GCG | GCC | AAT | GAT | CAA | GGC | GAG | GCG | GTC | AAG | GAC | GTA | ACG | CTA | 1494 |
| Cys | Lys | Ala | Ala | Asn | Asp | Gln | Gly | Glu | Ala | Val | Lys | Asp | Val | Thr | Leu |      |
| 470 |     |     |     | 475 |     |     |     |     | 480 |     |     |     |     | 485 |     |      |
| ACG | GTG | GAG | TAC | GCA | CCA | GCG | CTG | GAC | AGC | GTG | GGC | TGC | CCA | GAA | CGC | 1542 |
| Thr | Val | Glu | Tyr | Ala | Pro | Ala | Leu | Asp | Ser | Val | Gly | Cys | Pro | Glu | Arg |      |
|     |     |     |     | 490 |     |     |     |     | 495 |     |     |     |     | 500 |     |      |
| ATT | ACT | TGG | CTG | GAG | GGA | ACA | GAA | GCC | TCG | CTG | AGC | TGT | GTG | GCG | CAC | 1590 |
| Ile | Thr | Trp | Leu | Glu | Gly | Thr | Glu | Ala | Ser | Leu | Ser | Cys | Val | Ala | His |      |
|     |     |     |     | 505 |     |     |     |     | 510 |     |     |     |     | 515 |     |      |
| GGG | GTA | CCG | CCG | CCT | GAT | GTG | ATC | TGC | GTG | CGC | TCT | GGA | GAA | CTC | GGG | 1638 |
| Gly | Val | Pro | Pro | Pro | Asp | Val | Ile | Cys | Val | Arg | Ser | Gly | Glu | Leu | Gly |      |
|     |     | 520 |     |     |     |     | 525 |     |     |     |     | 530 |     |     |     |      |
| GCC | GTC | ATC | GAG | GGG | CTG | TTG | CGT | GTG | GCC | CGG | GAG | CAT | GCG | GGC | ACT | 1686 |
| Ala | Val | Ile | Glu | Gly | Leu | Leu | Arg | Val | Ala | Arg | Glu | His | Ala | Gly | Thr |      |
|     |     | 535 |     |     |     |     | 540 |     |     |     |     | 545 |     |     |     |      |
| TAC | CGC | TGC | GAA | GCC | ACC | AAC | CCT | CGG | GGC | TCT | GCG | GCC | AAA | AAT | GTG | 1734 |
| Tyr | Arg | Cys | Glu | Ala | Thr | Asn | Pro | Arg | Gly | Ser | Ala | Ala | Lys | Asn | Val |      |
| 550 |     |     |     | 555 |     |     |     |     | 560 |     |     |     |     | 565 |     |      |
| GCC | GTC | ACG | GTG | GAA | TAT | GGC | CCC | AGG | TTT | GAG | GAG | CCG | AGC | TGC | CCC | 1782 |

-continued

| | | | | | | | | | | | | | | | | |
|---|---|---|---|---|---|---|---|---|---|---|---|---|---|---|---|---|
| Ala | Val | Thr | Val | Glu 570 | Tyr | Gly | Pro | Arg 575 | Phe | Glu | Glu | Pro | Ser 580 | Cys | Pro | |
| AGC Ser | AAT Asn | TGG Trp | ACA Thr 585 | TGG Trp | GTG Val | GAA Glu | GGA Gly | TCT Ser 590 | GGG Gly | CGC Arg | CTG Leu | TTT Phe | TCC Ser 595 | TGT Cys | GAG Glu | 1830 |
| GTC Val | GAT Asp | GGG Gly 600 | AAG Lys | CCA Pro | CAG Gln | CCA Pro | AGC Ser 605 | GTG Val | AAG Lys | TGC Cys | GTG Val | GGC Gly 610 | TCC Ser | GGG Gly | GGC Gly | 1878 |
| ACC Thr | ACT Thr 615 | GAG Glu | GGG Gly | GTG Val | CTG Leu 620 | CTG Leu | CCG Pro | CTG Leu | GCA Ala | CCC Pro 625 | CCA Pro | GAC Asp | CCT Pro | AGT Ser | CCC Pro | 1926 |
| AGA Arg 630 | GCT Ala | CCC Pro | AGA Arg | ATC Ile | CCT Pro 635 | AGA Arg | GTC Val | CTG Leu | GCA Ala | CCC Pro 640 | GGT Gly | ATC Ile | TAC Tyr | GTC Val | TGC Cys 645 | 1974 |
| AAC Asn | GCC Ala | ACC Thr | AAC Asn | CGC Arg 650 | CAC His | GGC Gly | TCC Ser | GTG Val | GCC Ala 655 | AAA Lys | ACA Thr | GTC Val | GTC Val | GTG Val 660 | AGC Ser | 2022 |
| GCG Ala | GAG Glu | TCG Ser | CCA Pro 665 | CCG Pro | GAG Glu | ATG Met | GAT Asp | GAA Glu 670 | TCT Ser | ACC Thr | TGC Cys | CCA Pro | AGT Ser 675 | CAC His | CAG Gln | 2070 |
| ACG Thr | TGG Trp | CTG Leu 680 | GAA Glu | GGG Gly | GCT Ala | GAG Glu | GCT Ala 685 | TCC Ser | GCG Ala | CTG Leu | GCC Ala | TGC Cys 690 | GCC Ala | GCC Ala | CGG Arg | 2118 |
| GGT Gly | CGC Arg 695 | CCT Pro | TCC Ser | CCA Pro | GGA Gly | GTG Val 700 | CGC Arg | TGC Cys | TCT Ser | CGG Arg | GAA Glu 705 | GGC Gly | ATC Ile | CCA Pro | TGG Trp | 2166 |
| CCT Pro 710 | GAG Glu | CAG Gln | CAG Gln | CGC Arg | GTG Val 715 | TCC Ser | CGA Arg | GAG Glu | GAC Asp | GCG Ala 720 | GGC Gly | ACT Thr | TAC Tyr | CAC His | TGT Cys 725 | 2214 |
| GTG Val | GCC Ala | ACC Thr | AAT Asn | GCG Ala 730 | CAT His | GGC Gly | ACG Thr | GAC Asp | TCC Ser 735 | CGG Arg | ACC Thr | GTC Val | ACT Thr | GTG Val 740 | GGC Gly | 2262 |
| GTG Val | GAA Glu | TAC Tyr | CGG Arg 745 | CCA Pro | GTG Val | GTG Val | GCC Ala | GAA Glu 750 | CTT Leu | GCT Ala | GCC Ala | TCG Ser | CCC Pro 755 | CCT Pro | GGA Gly | 2310 |
| GGC Gly | GTG Val | CGC Arg 760 | CCA Pro | GGA Gly | GGA Gly | AAC Asn | TTC Phe 765 | ACG Thr | TTG Leu | ACC Thr | TGC Cys | CGC Arg 770 | GCG Ala | GAG Glu | GCC Ala | 2358 |
| TGG Trp | CCT Pro 775 | CCA Pro | GCC Ala | CAG Gln | ATC Ile | AGC Ser 780 | TGG Trp | CGC Arg | GCG Ala | CCC Pro | CCG Pro 785 | AGG Arg | GCC Ala | CTC Leu | AAC Asn | 2406 |
| ATC Ile 790 | GGC Gly | CTG Leu | TCG Ser | AGC Ser | AAC Asn 795 | AAC Asn | AGC Ser | ACA Thr | CTG Leu | AGC Ser 800 | GTG Val | GCA Ala | GGC Gly | GCC Ala | ATG Met 805 | 2454 |
| GGA Gly | AGC Ser | CAC His | GGC Gly | GGC Gly 810 | GAG Glu | TAC Tyr | GAG Glu | TGC Cys | GCA Ala 815 | CGC Arg | ACC Thr | AAC Asn | GCG Ala | CAC His 820 | GGG Gly | 2502 |
| CGC Arg | CAC His | GCG Ala | CGG Arg 825 | CGC Arg | ATC Ile | ACG Thr | GTG Val | CGC Arg 830 | GTG Val | GCC Ala | GGT Gly | CCG Pro | TGG Trp 835 | CTA Leu | TGG Trp | 2550 |
| GTC Val | GCC Ala | GTG Val 840 | GGC Gly | GGC Gly | GCG Ala | GCG Ala | GGG Gly 845 | GGC Gly | GCG Ala | GCG Ala | CTG Leu | CTG Leu 850 | GCC Ala | GCG Ala | GGG Gly | 2598 |
| GCC Ala | GGC Gly | CTG Leu 855 | GCC Ala | TTC Phe | TAC Tyr | GTG Val | CAG Gln 860 | TCC Ser | ACC Thr | GCC Ala | TGC Cys | AAG Lys 865 | AAG Lys | GGC Gly | GAG Glu | 2646 |
| TAC Tyr | AAC Asn 870 | GTG Val | CAG Gln | GAG Glu | GCC Ala | GAG Glu 875 | AGC Ser | TCA Ser | GGC Gly | GAG Glu | GCC Ala 880 | GTG Val | TGT Cys | CTG Leu | AAC Asn 885 | 2694 |
| GGA Gly | GCG Ala | GGC Gly | GGC Gly | GGC Gly | GCT Ala | GGC Gly | GGG Gly | GCG Ala | GCA Ala | GGC Gly | GCG Ala | GAG Glu | GGC Gly | GGA Gly | CCC Pro | 2742 |

-continued

```
Gly Ala Gly Gly Gly Ala Gly Gly Ala Ala Gly Ala Glu Gly Gly Pro
                890                 895                 900

GAG GCG GCG GGG GGC GCG GCC GAG TCG CCG GCG GAG GGC GAG GTC TTC    2790
Glu Ala Ala Gly Gly Ala Ala Glu Ser Pro Ala Glu Gly Glu Val Phe
                905                 910                 915

GCC ATA CAG CTG ACA TCG GCG TGAGCCCGCT CCCCTCTCCG CGGGCCGGGA       2841
Ala Ile Gln Leu Thr Ser Ala
                920             925

CGCCCCCAG ACTCACACGG GGGCTTATTT ATTGCTTTAT TTATTACTT ATTCATTTAT    2901

TTATGTATTC AACTCCAAGG GAATTC                                       2927
```

(2) INFORMATION FOR SEQ ID NO:28:

(i) SEQUENCE CHARACTERISTICS:
        (A) LENGTH: 924 amino acids
        (B) TYPE: amino acid
        (D) TOPOLOGY: linear (ii) MOLECULE TYPE: protein (xi) SEQUENCE DESCRIPTION: SEQ ID NO:28:

```
Met Pro Gly Pro Ser Pro Gly Leu Arg Arg Ala Leu Leu Gly Leu Trp
 1               5                  10                  15

Ala Ala Leu Gly Leu Gly Leu Phe Gly Leu Ser Ala Val Ser Gln Glu
                20                  25                  30

Pro Phe Trp Ala Asp Leu Gln Pro Arg Val Ala Phe Val Glu Arg Gly
                35                  40                  45

Gly Ser Leu Trp Leu Asn Cys Ser Thr Asn Cys Pro Arg Pro Glu Arg
    50                  55                  60

Gly Gly Leu Glu Thr Ser Leu Arg Arg Asn Gly Thr Gln Arg Gly Leu
65                  70                  75                  80

Arg Trp Leu Ala Arg Gln Leu Val Asp Ile Arg Glu Pro Glu Thr Gln
                85                  90                  95

Pro Val Cys Phe Phe Arg Cys Ala Arg Arg Thr Leu Gln Ala Arg Gly
                100                 105                 110

Leu Ile Arg Thr Phe Gln Arg Pro Asp Arg Val Glu Leu Met Pro Leu
                115                 120                 125

Pro Pro Trp Gln Pro Val Gly Glu Asn Phe Thr Leu Ser Cys Arg Val
    130                 135                 140

Pro Gly Ala Gly Pro Arg Ala Ser Leu Thr Leu Thr Leu Leu Arg Gly
145                 150                 155                 160

Ala Gln Glu Leu Ile Arg Arg Ser Phe Ala Gly Glu Pro Pro Arg Ala
                165                 170                 175

Arg Gly Ala Val Leu Thr Ala Thr Val Leu Ala Arg Arg Glu Asp His
                180                 185                 190

Gly Ala Asn Phe Ser Cys Arg Ala Glu Leu Asp Leu Arg Pro His Gly
                195                 200                 205

Leu Gly Leu Phe Glu Asn Ser Ser Ala Pro Arg Glu Leu Arg Thr Phe
    210                 215                 220

Ser Leu Ser Pro Asp Ala Pro Arg Leu Ala Ala Pro Arg Leu Leu Glu
225                 230                 235                 240

Val Gly Ser Glu Arg Pro Val Ser Cys Thr Leu Asp Gly Leu Phe Pro
                245                 250                 255

Ala Ser Glu Ala Arg Val Tyr Leu Ala Leu Gly Asp Gln Asn Leu Ser
                260                 265                 270

Pro Asp Val Thr Leu Glu Gly Asp Ala Phe Val Ala Thr Ala Thr Ala
                275                 280                 285
```

```
Thr  Ala  Ser  Ala  Glu  Gln  Glu  Gly  Ala  Arg  Gln  Leu  Val  Cys  Asn  Val
290                 295                 300
Thr  Leu  Gly  Gly  Glu  Asn  Arg  Glu  Thr  Arg  Glu  Asn  Val  Thr  Ile  Tyr
305                 310                 315                           320
Ser  Phe  Pro  Ala  Pro  Leu  Leu  Thr  Leu  Ser  Glu  Pro  Ser  Val  Ser  Glu
               325                 330                      335
Gly  Gln  Met  Val  Thr  Val  Thr  Cys  Ala  Ala  Gly  Ala  Gln  Ala  Leu  Val
               340                 345                      350
Thr  Leu  Glu  Gly  Val  Pro  Ala  Ala  Val  Pro  Gly  Gln  Pro  Ala  Gln  Leu
          355                 360                      365
Gln  Leu  Asn  Ala  Thr  Glu  Asn  Asp  Asp  Arg  Arg  Ser  Phe  Phe  Cys  Asp
370                      375                 380
Ala  Thr  Leu  Asp  Val  Asp  Gly  Glu  Thr  Leu  Ile  Lys  Asn  Arg  Ser  Ala
385                 390                 395                           400
Glu  Leu  Arg  Val  Leu  Tyr  Ala  Pro  Arg  Leu  Asp  Asp  Ser  Asp  Cys  Pro
                    405                 410                 415
Arg  Ser  Trp  Thr  Trp  Pro  Glu  Gly  Pro  Glu  Gln  Thr  Leu  Arg  Cys  Glu
               420                 425                      430
Ala  Arg  Gly  Asn  Pro  Glu  Pro  Ser  Val  His  Cys  Ala  Arg  Ser  Asp  Gly
          435                 440                      445
Gly  Ala  Val  Leu  Ala  Leu  Gly  Leu  Leu  Gly  Pro  Val  Thr  Arg  Ala  Leu
450                      455                 460
Ser  Gly  Thr  Tyr  Arg  Cys  Lys  Ala  Ala  Asn  Asp  Gln  Gly  Glu  Ala  Val
465                      470                 475                           480
Lys  Asp  Val  Thr  Leu  Thr  Val  Glu  Tyr  Ala  Pro  Ala  Leu  Asp  Ser  Val
                    485                 490                      495
Gly  Cys  Pro  Glu  Arg  Ile  Thr  Trp  Leu  Glu  Gly  Thr  Glu  Ala  Ser  Leu
               500                 505                      510
Ser  Cys  Val  Ala  His  Gly  Val  Pro  Pro  Asp  Val  Ile  Cys  Val  Arg
          515                 520                      525
Ser  Gly  Glu  Leu  Gly  Ala  Val  Ile  Glu  Gly  Leu  Leu  Arg  Val  Ala  Arg
530                      535                 540
Glu  His  Ala  Gly  Thr  Tyr  Arg  Cys  Glu  Ala  Thr  Asn  Pro  Arg  Gly  Ser
545                      550                 555                           560
Ala  Ala  Lys  Asn  Val  Ala  Val  Thr  Val  Glu  Tyr  Gly  Pro  Arg  Phe  Glu
               565                 570                      575
Glu  Pro  Ser  Cys  Pro  Ser  Asn  Trp  Thr  Trp  Val  Glu  Gly  Ser  Gly  Arg
               580                 585                      590
Leu  Phe  Ser  Cys  Glu  Val  Asp  Gly  Lys  Pro  Gln  Pro  Ser  Val  Lys  Cys
          595                 600                      605
Val  Gly  Ser  Gly  Gly  Thr  Thr  Glu  Gly  Val  Leu  Leu  Pro  Leu  Ala  Pro
610                      615                 620
Pro  Asp  Pro  Ser  Pro  Arg  Ala  Pro  Arg  Ile  Pro  Arg  Val  Leu  Ala  Pro
625                      630                 635                           640
Gly  Ile  Tyr  Val  Cys  Asn  Ala  Thr  Asn  Arg  His  Gly  Ser  Val  Ala  Lys
                    645                 650                      655
Thr  Val  Val  Val  Ser  Ala  Glu  Ser  Pro  Pro  Glu  Met  Asp  Glu  Ser  Thr
               660                 665                      670
Cys  Pro  Ser  His  Gln  Thr  Trp  Leu  Glu  Gly  Ala  Glu  Ala  Ser  Ala  Leu
          675                 680                      685
Ala  Cys  Ala  Ala  Arg  Gly  Arg  Pro  Ser  Pro  Gly  Val  Arg  Cys  Ser  Arg
690                      695                 700
Glu  Gly  Ile  Pro  Trp  Pro  Glu  Gln  Gln  Arg  Val  Ser  Arg  Glu  Asp  Ala
```

```
705                    710                    715                    720
Gly Thr Tyr His Cys Val Ala Thr Asn Ala His Gly Thr Asp Ser Arg
             725                730                735

Thr Val Thr Val Gly Val Glu Tyr Arg Pro Val Val Ala Glu Leu Ala
             740                745                750

Ala Ser Pro Pro Gly Gly Val Arg Pro Gly Gly Asn Phe Thr Leu Thr
             755                760                765

Cys Arg Ala Glu Ala Trp Pro Pro Ala Gln Ile Ser Trp Arg Ala Pro
             770                775                780

Pro Arg Ala Leu Asn Ile Gly Leu Ser Ser Asn Asn Ser Thr Leu Ser
785                790                795                800

Val Ala Gly Ala Met Gly Ser His Gly Gly Glu Tyr Glu Cys Ala Arg
                 805                810                815

Thr Asn Ala His Gly Arg His Ala Arg Arg Ile Thr Val Arg Val Ala
             820                825                830

Gly Pro Trp Leu Trp Val Ala Val Gly Gly Ala Ala Gly Gly Ala Ala
             835                840                845

Leu Leu Ala Ala Gly Ala Gly Leu Ala Phe Tyr Val Gln Ser Thr Ala
    850                855                860

Cys Lys Lys Gly Glu Tyr Asn Val Gln Glu Ala Glu Ser Ser Gly Glu
865                870                875                880

Ala Val Cys Leu Asn Gly Ala Gly Gly Ala Gly Gly Ala Ala Gly
             885                890                895

Ala Glu Gly Gly Pro Glu Ala Ala Gly Gly Ala Ala Glu Ser Pro Ala
             900                905                910

Glu Gly Glu Val Phe Ala Ile Gln Leu Thr Ser Ala
        915                920
```

( 2 ) INFORMATION FOR SEQ ID NO:29:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

```
GTACTTACAG GATCCGCGGT CTCGCAGGAG CCCTTCTGGG CGGACCTACA GCCTGCGTGG        60

CGTTC                                                                    65
```

( 2 ) INFORMATION FOR SEQ ID NO:30:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

```
ATTTCTCTCG AGGATGGTCA CGTTCTCCCG G                                       31
```

( 2 ) INFORMATION FOR SEQ ID NO:31:

( i ) SEQUENCE CHARACTERISTICS:
        ( A ) LENGTH: 33 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:31:

ATTTCTGGAT CCTACAGCTT CCCGGCACCA CTC  33

( 2 ) INFORMATION FOR SEQ ID NO:32:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:32:

ATTTCTCTCG AGTTCCACGC CCACAGTGAC GG  32

POLYNUCLEOTIDES ENCODING HUMAN ICAM-4

This application is a continuation-in-part of U.S. patent application Ser. No. 08/245,295, filed May 18, 1994, which in turn is a continuation-in-part of U.S. patent application Ser. No. 08/102,852, filed Aug. 5, 1993 now abandoned, as a continuation-in-part of U.S. patent application Ser. No. 08/009,266, filed Jan. 22, 1993, now abandoned, as a continuation-in-part of U.S. patent application Ser. No. 07/894,061, filed Jun. 5, 1992, now abandoned, as a continuation-in-part of U.S. patent application Ser. No. 07/889,724, filed May 26, 1992, now abandoned, as a continuation-in-part of U.S. patent application Ser. No. 07/827,689, filed Jan. 27, 1992 now abandoned.

FIELD OF THE INVENTION

The present invention relates generally to cellular adhesion molecules and more particularly to the cloning and expression of DNA encoding a heretofore unknown polypeptide designated "ICAM-4" which possesses structural relatedness to the intercellular adhesion molecules ICAM-1, ICAM-2, and ICAM-R.

BACKGROUND OF THE INVENTION

Research spanning the last decade has significantly elucidated the molecular events attending cell-cell interactions in the body, especially those events involved in the movement and activation of cells in the immune system, and more recently, those involved in development and normal physiological function of cells in the nervous system. See generally, Springer, *Nature*, 346: 425–434 (1990) regarding cells of the immune system, and Yoshihara, et al. *Neurosci. Res.* 10:83–105 (1991) and Sonderegger and Rathjen, *J. Cell Biol.* 119:1387–1394 (1992) regarding cells of the nervous system. Cell surface proteins, and especially the so-called Cellular Adhesion Molecules ("CAMs") have correspondingly been the subject of pharmaceutical research and development having as its goal intervention in the processes of leukocyte extravasation to sites of inflammation and leukocyte movement to distinct target tissues, as well as neuronal differentiation and formation of complex neuronal circuitry. The isolation and characterization of cellular adhesion molecules, the cloning and expression of DNA sequences encoding such molecules, and the development of therapeutic and diagnostic agents relevant to inflammatory processes and development and function of the nervous system have also been the subject of numerous U.S. and foreign applications for Letters Patent. See Edwards, *Current Opinion in Therapeutic Patents*, 1(11): 1617–1630 (1991) and particularly the published "patent literature references" cited therein.

Of fundamental interest to the background of the present invention are the prior identification and characterization of certain mediators of cell adhesion events, the "leukointegrins," LFA-1, MAC-1 and gp 150.95 (referred to in WHO nomenclature as CD18/CD11a, CD18/CD11b, and CD18/CD11c, respectively) which form a subfamily of heterodimeric "integrin" cell surface proteins present on B lymphocytes, T lymphocytes, monocytes and granulocytes. See, e.g., Table 1 of Springer, supra, at page 429. Also of interest are other single chain adhesion molecules (CAMs) that have been implicated in leukocyte activation, adhesion, motility and the like, which are events attendant to the inflammatory process. For example, it is presently believed that prior to the leukocyte extravasation which characterizes inflammatory processes, activation of integrins constitutively expressed on leukocytes occurs and is followed by a tight ligand/receptor interaction between the integrins (e.g., LFA-1) and one or both of two distinct intercellular adhesion molecules (ICAMs) designated ICAM-1 and ICAM-2 which are expressed on blood vessel endothelial cell surfaces and on other leukocytes.

Like the other CAMs characterized to date, [e.g., vascular adhesion molecule (VCAM-1) as described in PCT WO 90/13300 published Nov. 15, 1990; and platelet endothelial cell adhesion molecule (PECAM-1) as described in Newman et at., *Science*, 247:1219–1222 (1990) and PCT WO 91/10683 published Jul. 25, 1991], ICAM-1 and ICAM-2 are structurally homologous to other members of the immunoglobulin gene superfamily in that the extracellular portion of each is comprised of a series of domains sharing a similar carboxy terminal motif. A "typical" immunoglobulin-like domain contains a loop structure usually anchored by a disulfide bond between two cysteines at the extremity of each loop. ICAM-1 includes five immunoglobulin-like domains; ICAM-2, which differs from ICAM-1 in terms of cell distribution, includes two such domains; PECAM-1 includes six; VCAM includes six or seven, depending on splice variations, and so on. Moreover, CAMs typically include a hydrophobic "transmembrane" region believed to participate in orientation of the molecule at the cell surface and a carboxy terminal "cytoplasmic" region. Graphic models of the operative disposition of CAMs generally show the molecule anchored in the cell membrane at the transmembrane region with the cytoplasmic "tail" extending into the cell cytoplasm and one or more immunoglobulin-like loops extending outward from the cell surface.

A number of neuronal cells express surface receptors with extracellular Ig-like domains, structurally similarity to the ICAMs. See for example, Yoshihara, et al., supra. In addition to Ig-like domains, many adhesion molecules of the nervous system also contain tandemly repeated fibronectin-like sequences in the extracellular domain.

A variety of therapeutic uses has been projected for intercellular adhesion molecules, including uses premised on the ability of ICAM-1 to bind human rhinovirus. European Patent Application 468 257 A published Jan. 29, 1992, for example, addresses the development of multimeric configurations and forms of ICAM-1 (including full length and truncated molecular forms) proposed to have enhanced ligand/receptor binding activity, especially in binding to viruses, lymphocyte associated antigens and pathogens such as *Plasmodium falciparum*.

In a like manner, a variety of uses has been projected for proteins immunologically related to intercellular adhesion molecules. WO91/16928, published Nov. 14, 1991, for example, addresses humanized chimeric anti-ICAM-1 antibodies and their use in treatment of specific and non-specific inflammation, viral infection and asthma. Anti-ICAM-1 antibodies and fragments thereof are described as useful in treatment of endotoxic shock in WO92/04034, published Mar. 19, 1992. Inhibition of ICAM-1 dependent inflammatory responses with anti-ICAM-1 anti-idiotypic antibodies and antibody fragments is addressed in WO92/06119, published Apr. 16, 1992.

Despite the fundamental insights into cell adhesion phenomena which have been gained by the identification and characterization of intercellular adhesion proteins such as ICAM-1 and lymphocyte interactive integrins such as LFA-1, the picture is far from complete. It is generally believed that numerous other proteins are involved in inflammatory processes and in targeted lymphocyte movement throughout the body. For example, U.S. patent application Ser. Nos. 07/827,689, 07/889,724, 07/894,061 and 08/009,266 all now abandoned, and corresponding published PCT Application WO 93/14776 (published Aug. 5, 1993) disclose the cloning and expression of an ICAM-Related protein, ICAM-R. The disclosures of these applications are specifically incorporated by reference herein and the DNA and amino acid sequences of ICAM-R are set out in SEQ ID NO. 4 herein. This new ligand has been found to be expressed on human lymphocytes, monocytes and granulocytes.

Of particular interest to the present application, still another ICAM-like surface molecule was identified which has a tissue specific expression unlike that of any known ICAM molecule. Mori, et al., [*Proc. Natl. Acad. Sci.(USA)* 84:3921–3925 (1987)] reported identification of a telencephalon-specific antigen in rabbit brain, specifically immunoreactive with monoclonal antibody 271A6. This surface antigen was named telencephalin. Imamura, et al., [*Neurosci. Letts.* 119:118–121 (1990)], using a polyclonal antibody to assess localized expression, asserted that expression of telencephalin in visual cortex of cats showed variation in layers of the tissue, and also reported telencephalin expression was variable as a function of development. Oka, et al., [*Neuroscience* 35:93–103 (1990)] subsequently reported isolation of telencephalin using monoclonal antibody 271A6. The publication reports a molecular weight for the surface molecule of about 500 kD and that the molecule was composed of four subunits, each with a native molecular weight of 130 kD and approximately 100 kD following N-glycanase treatment. Yoshihiro, et al., [*Neuroscience, Research Supplement* 18, p. S83 (1994)], reported the cDNA and amino acid sequences for rabbit telencephalin at the 17th Annual Meeting of the Japan Neuroscience Society in Nagoya, Japan, Dec. 7–9, 1993, and the 23rd Annual Meeting of the Society for Neuroscience in Washington, D.C., Nov. 9, 1993 [Society for Neuroscience Abstracts 19 (1–3) p. 646 (1993)]. The deduced amino acid sequence reported suggested that the 130 kD telencephalon is an integral membrane protein with nine extracellular immunoglobulin (Ig)-like domains. The distal eight of these domains showed homology to other ICAM Ig-like domains. This same information was reported by Yoshihara, et al., in *Neuron* 12:543–553 (1994).

There thus continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Such seminal information would inter alia, provide for the large scale production of the proteins, allow for the identification of cells naturally producing them, and permit the preparation of antibody substances or other novel binding proteins specifically reactive therewith and/or inhibitory of ligand/receptor binding reactions in which they are involved.

BRIEF SUMMARY OF THE INVENTION

In one of its aspects, the present invention provides purified and isolated polynucleotides (e.g., DNA sequences, RNA transcripts and anti-sense oligonucleotides thereof) encoding a novel polypeptide, "ICAM-4," as well as polypeptide variants (including fragments and deletion, substitution, and addition analogs) thereof which display one or more ligand/receptor binding biological activities and/or immunological properties specific to ICAM-4. ICAM-4-specific ligand/receptor binding biological activities encompass interactions of both the ICAM-4 extracellular and cytoplasmic domains with other molecules (e.g., in processes of cell—cell adhesion and/or signal transduction). Preferred DNA sequences of the invention include genomic and cDNA sequences as well as wholly or partially chemically synthesized DNA sequences. A presently preferred polynucleotide is set out in SEQ ID NO: 1 and encodes rat species ICAM-4. Biological replicas (i.e., copies of isolated DNA sequences made in vivo or in vitro) of DNA sequences of the invention are contemplated. Also provided are autonomously replicating recombinant constructions such as plasmid and viral DNA vectors incorporating ICAM-4 sequences and especially vectors wherein DNA encoding ICAM-4 or an ICAM-4 variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such ICAM-4 and ICAM-4 variant products can serve a variety of useful purposes. To the extent that the expressed products are "displayed" on host cell surfaces, the cells may constitute a valuable immunogen for the development of antibody substances specifically immunoreactive with ICAM-4 and ICAM-4 variants. Host cells of the invention are conspicuously useful in methods for the large scale production of ICAM-4 and ICAM-4 variants wherein the cells are grown in a suitable culture medium and the desired polypeptide products are isolated from the cells or from the medium in which the cells are grown.

Novel ICAM-4 of the invention may be obtained as isolates from natural cell sources, but, along with ICAM-4 variant products, are preferably produced by recombinant procedures involving host cells of the invention. A presently preferred amino acid sequence for an ICAM-4 polypeptide is set out in SEQ ID NO: 2. The products may be obtained in fully or partially glycosylated, partially or wholly de-glycosylated, or non-glycosylated forms, depending on the host cell selected for recombinant production and/or post-isolation processing. ICAM-4 variants of the invention may comprise water soluble or insoluble monomeric, multimeric or cyclic ICAM-4 fragments which include all or part of one or more of the domain regions specified above and having a biological or immunological property of ICAM-4 including, e.g., the ability to bind to a binding partner of ICAM-4 and/or inhibit binding of ICAM-4 to a natural binding partner. ICAM-4 variants of the invention may also comprise polypeptide analogs wherein one or more of the specified amino acids is deleted or replaced: (1) without loss, and preferably with enhancement, of one or more biological activities or immunological characteristics specific for ICAM-4; or (2) with specific disablement of a particular ligand/receptor binding function. Analog polypeptides including additional amino acid (e.g., lysine or cysteine) residues that facilitate multimer formation are contemplated.

Also comprehended by the present invention are antibody substances (e.g., monoclonal and polyclonal antibodies, antibody fragments, single chain antibodies, chimeric antibodies, CDR-grafted antibodies and the like) and other binding proteins (e.g., polypeptides and peptides) which are specific (i.e., non-reactive with the ICAM-1, ICAM-2, and ICAM-R intercellular adhesion molecules to which ICAM-4 is structurally related) for ICAM-4 or ICAM-4 variants. Antibody substances can be developed using isolated natural or recombinant ICAM-4 or ICAM-4 variants or cells expressing such products on their surfaces. Binding proteins of the invention are additionally useful for characterization of binding site structure(s) (e.g., epitopes and/or sensitivity of binding properties to modifications in ICAM-4 amino acid sequence).

Binding proteins useful, in turn, in compositions for immunization as well as for purifying polypeptides of the invention and identifying cells displaying the polypeptides on their surfaces. They are also manifestly useful in modulating (i.e., blocking, inhibiting or stimulating) ligand/receptor binding biological activities involving ICAM-4, especially those ICAM-4 effector functions involved in specific and non-specific immune system responses. Anti-idiotypic antibodies specific for anti-ICAM-4 antibody substances and uses of such anti-idiotypic antibody substances in modulating immune responses are also contemplated. Assays for the detection and quantification of ICAM-4 on cell surfaces and in body fluids, such as serum or cerebrospinal fluid, may involve, for example, a single antibody substance or multiple antibody substances in a "sandwich" assay format.

The scientific value of the information contributed through the disclosures of DNA and amino acid sequences of the present invention is manifest. As one series of examples, knowledge of the sequence of a cDNA for ICAM-4 makes possible the isolation by DNA/DNA hybridization of genomic DNA sequences encoding ICAM-4 and specifying ICAM-4 expression control regulatory sequences such as promoters, operators and the like. DNA/DNA hybridization procedures carried out with DNA sequences of the invention and under stringent conditions are likewise expected to allow the isolation of DNAs encoding allelic variants of ICAM-4, other structurally related proteins sharing one or more of the biological and/or immunological properties specific to ICAM-4, and proteins homologous to ICAM-4 from other species. DNAs of the invention are useful in DNA/RNA hybridization assays to detect the capacity of cells to synthesize ICAM-4. Also made available by the invention are anti-sense polynucleotides relevant to regulating expression of ICAM-4 by those cells which ordinarily express the same. As another series of examples, knowledge of the DNA and amino acid sequences of ICAM-4 makes possible the generation by recombinant means of ICAM-4 variants such as hybrid fusion proteins (sometimes referred to as "immunoadhesions") characterized by the presence of ICAM-4 protein sequences and immunoglobulin heavy chain constant regions and/or hinge regions. See, Capon et al., *Nature*, 337:525–531 (1989); Ashkenazi et al., P.N.A.S. (USA), 88:10535–10539 (1991); and PCT WO 89/02922, published Apr. 6, 1989. ICAM-4 variant fusion proteins may also include, for example, selected extracellular domains of ICAM-4 and portions of other cell adhesion molecules.

The DNA and amino acid sequence information provided by the present invention also makes possible the systematic analysis of the structure and function of ICAM-4 and definition of those molecules with which it will interact on extracellular and intracellular levels. The idiotypes of anti-ICAM-4 monoclonal antibodies of the invention are representative of such molecules and may mimic natural binding proteins (peptides and polypeptides) through which ICAM-4 intercellular and intracellular activities are modulated or by which ICAM-4 modulates intercellular and intracellular events. Alternately, they may represent new classes of modulators of ICAM-4 activities. Anti-idiotypic antibodies, in turn, may represent new classes of biologically active ICAM-4 equivalents. In vitro assays for identifying antibodies or other compounds that modulate the activity of ICAM-4 may involve, for example, immobilizing ICAM-4 or a natural ligand to which ICAM-4 binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of ICAM-4 binding. The DNA sequence information provided by the present invention also makes possible the development, by homologous recombination or "knockout" strategies [see, e.g., Capecchi, *Science*, 244:1288–1292 (1989)], of rodents that fail to express a functional ICAM-4 protein or that express a variant ICAM-4 protein. Such rodents are useful as models for studying the activities of ICAM-4 and ICAM-4 modulators in vivo.

DETAILED DESCRIPTION OF THE INVENTION

The disclosures of parent U.S. patent application Ser. No. 08/102,852, filed Aug. 5, 1993, now abandoned, are specifically incorporated by reference. The examples of that application address, inter alia: design and construction of oligonucleotide probes for PCR amplification of ICAM related DNAs; use of the probes to amplify a human genomic fragment homologous to, but distinct from DNAs encoding ICAM-1 and ICAM-2; screening of cDNA libraries with the genomic fragment to isolate additional ICAM-R coding sequences; screening of cDNA libraries to isolate a full length human cDNA sequence encoding ICAM-R; characterization of DNA and amino acid sequence information for ICAM-R, especially as related to ICAM-1 and ICAM-2; development of mammalian host cells expressing ICAM-R; assessment of indications of ICAM-R participation in adhesion events involving CD18-dependent and CD18-independent pathways; inhibition of cell adhesion to ICAM-R by ICAM-R-derived peptides; expression of variants of ICAM-R; preparation and characterization of anti-ICAM-R antibodies and fragments thereof; mapping of ICAM-R epitopes recognized by anti-ICAM-R monoclonal antibodies; assessment of the distribution and biochemical characterization of ICAM-R and RNA encoding the same; assessment of ICAM-R in homotypic cell-cell adhesion and immune cell activation/proliferation; characterization of ICAM-R monoclonal antibodies; and assessment of differential phosphorylation and cytoskeletal associations of the cytoplasmic domain of ICAM-R. Also disclosed was the identification of a rodent ICAM-encoding DNA that, at the time, appeared to be the rat homolog of human ICAM-R, and the use of this DNA to construct and express DNAs encoding glutathione-S-transferase fusion proteins. The detailed description of how this rodent DNA was identified can be found in the parent application U.S. Ser. No.(08/102, 852 now abandoned) in Example 6, and is reproduced herein as Example 1. As more of the rodent ICAM-coding sequence was identified, it became apparent that the rodent ICAM DNA did not encode a rat species homolog of human ICAM-R, but, in fact, encoded a novel ICAM polypeptide, herein named ICAM-4. In order to appreciate the events which led to the identification of ICAM-4, a chronology is provided which is followed by a detailed description of the invention.

A first rodent genomic ICAM-4 sequence was identified which encoded a region homologous to domain 2 (herein SEQ ID NO: 3, and SEQ ID NO: 23 of U.S. Ser. No. 08/102,852 now abandoned) of human ICAM-R (herein as SEQ ID NO: 4). A second, overlapping genomic DNA (herein SEQ ID NO: 5, and SEQ ID NO: 26 of U.S. Ser. No. 08/102,852 now abandoned) was also identified which encoded both the domain 2 region of SEQ ID NO: 3, and sequences for ICAM-1. Using SEQ ID NO: 3 as a probe, a rodent spleen cDNA (herein SEQ ID NO: 6, and SEQ ID NO: 25 in U.S. Ser. No. 08/102,852 now abandoned) was identified which encoded domains 2 through 5 as well as a fifth domain not previously observed as an ICAM domain. At this time, these newly identified rodent DNAs appeared to encode a rodent homolog of human ICAM-R, however alignment of 3' regions of these DNAs with other ICAMs proved difficult.

The subsequent isolation of a 1 kb cDNA clone from a rat spleen library, and amplification of an RT-PCR fragment indicated that a portion of both the cDNA and genomic clones had not been sequenced. Another RT-PCR amplification product (SEQ ID NO: 7) confirmed this omission. It was determined that a fragment of 177 bp was excised from the genomic and cDNA clones by EcoRI digestion of the clones to isolate these sequences from λ phage for DNA sequencing studies. Reanalysis of SEQ ID NOs: 5 and 6 in light of these other sequences permitted identification of more accurate and complete sequences for the originally isolated genomic and cDNA clones, presented in corrected form herein as SEQ ID NOs: 8 and 9.

In order to identify a complete coding sequence for ICAM-4, a rat brain cDNA (SEQ ID NO: 10) was isolated, and 5' end sequence determined by 5' rapid amplification of cDNA ends (5' RACE), the amplification product set forth in SEQ ID NO: 11. Combining information from the RT-PCR clone (SEQ ID NO: 7), the brain cDNA (SEQ ID NO: 10) and the RACE amplification product (SEQ ID NO: 11) permitted identification of the complete coding sequence for ICAM-4 (SEQ ID NO: 1).

The present invention is thus illustrated by the following examples. More particularly, Example 1 addresses cloning of a partial rodent ICAM-4 DNA. Example 2 describes Northern blot analysis of rodent ICAM-4 transcription. Example 3 describes isolation of a full length rodent ICAM-4 cDNA. Example 4 relates the in situ hybridization of rodent ICAM-4 in brain tissue. Example 5 addresses generation of ICAM-4 fusion proteins in prokaryotes. Example 6 describes production of monoclonal antibodies specific for rat ICAM-4/GST fusion proteins. Example 7 describes expression of soluble rat ICAM-4 proteins in a baculovirus expression system. Example 8 addresses production of monoclonal antibodies specific for rat ICAM-4 expressed in a baculovirus system. Example 9 describes immunocytochemical analysis of rat ICAM-4 expression. Example 10 relates cloning of a human genomic ICAM-4-encoding DNA. Example 11 addresses cloning of a human ICAM-4-encoding cDNA. Example 12 describes Northern analysis of human ICAM-4 expression. Example 13 describes generation of human ICAM-4/GST fusion proteins. Example 14 addresses production of monoclonal antibodies immunospecific for human ICAM-4.

EXAMPLE 1

Cloning of Rat ICAM-Related DNA

A. Isolation of a Rat Genomic ICAM-Related Domain 2 DNA

A rat genomic library constructed in λ EMBL3 was screened a with [$^{32}$P]-labeled probe generated by PCR from DNA encoding human ICAM-3 domain 2 The sequence of the probe is set forth in SEQ ID NO: 12. Library plaques were transferred to Hybond N+ nylon membranes (Amersham, Arlington Heights, Ill.). Screening of all cDNA and genomic libraries was performed according to standard protocols. Prehybridization and hybridizations were carried out in a solution of 40–50% formamide, 5X Denhardt's, 5X SSPE and 1.0% SDS at 42° C. Probes ([$^{32}$P]-labeled) were added at a concentration of $10^5$–$10^6$ cpm/ml of hybridization solution. Following 16–18 hours of hybridization, nylon membranes were washed extensively at room temperature in 2X SSPE with 0.1% SDS and subsequently exposed to X-ray film at −80° C. overnight. Positive plaques were subjected to one or more rounds of hybridization to obtain clonal phage. DNA prepared from lysate of the positive clones was subcloned into pBS+ and sequenced.

A first genomic clone encoding a rat ICAM-related domain 2 was identified that was determined to be homologous to domain 2 regions in other ICAM family members (see for example, Table 1 of U.S. patent application Ser. No. 08/102,852 now abandoned), yet was distinct from the previously reported nucleotide sequences for rat ICAM-1 [Kita, et al., *Biochem. Biophys. Acta* 1131:108–110 (1992)] or mouse ICAM-2 [Xu, et al., *J. Immunol.* 149:2560–2565 (1992)]. The nucleic acid and deduced amino acid sequences for this clone were disclosed in the co-pending parents to the present application as purportedly variant forms of rat ICAM-R and were set forth as SEQ ID NOs: 23 and 24, respectively, in U.S. Ser. No. 08/102,852 now abandoned. Herein, these same sequences are set out in SEQ ID NOs: 3 and 13, respectively.

A second, overlapping clone was also identified with the same probes and was determined to contain the ICAM domain 2 sequence of SEQ ID NO: 3 and 5' DNA encoding at least part of rat ICAM-1. The nucleic acid sequence for this clone was set forth in the co-pending parent to the present application as SEQ ID NO: 26 and is set forth herein as SEQ ID NO: 5. This second clone indicated that the ICAM-related gene fragment of the first clone and the gene encoding rat ICAM-1 are located on the same rat chromosome within 5 kb of each other.

B. Isolation of Rat ICAM-Related cDNA

In order to identify a more complete protein coding sequence for the ICAM-related polypeptide, [$^{32}$P]-labeled DNA encoding the domain 2 sequence from the rat genomic clone identified in Section A (SEQ ID NO: 3), supra, was used to screen a number of cDNA libraries from various rat and mouse cell types, including rat macrophage (Clontech, Palo Alto, Calif.), peripheral blood lymphocyte (PBL) (Clontech), T cell (constructed in-house), and spleen (Clontech), and mouse PBL (Clontech), T cell (constructed in-house), and B cell (constructed in-house).

A single clone was identified in a rat spleen cDNA library (Clontech) which contained five Ig-like domains, four of which were homologous to domains 2 through 5 in both ICAM-1 and ICAM-R. Moreover, this clone included 3' DNA encoding an apparent fifth Ig-like domain which had not been previously identified in any other ICAM polypeptide. In addition, the clone contained an unusual 3' sequence subsequently determined to be a partial intron (discussed infra) located between domains 4 and 5, suggesting that the clone was the product of an immature or aberrantly spliced transcript. The presence of the unique domain and the determination that the 3' region did not properly align with other known ICAMs suggested that the ICAM-related DNA potentially encoded a novel rat ICAM polypeptide. The nucleic acid sequence for this clone was set forth in the parent to the present application as SEQ ID NO: 25; herein the nucleic acid sequence for this spleen cDNA clone is set forth in SEQ ID NO: 6.

C. Re-analysis of Rat cDNA and Genomic DNAs

Subsequent to the Aug. 5, 1993 filing of U.S. patent application Ser. No. 08/102,852, now abandoned, it was determined that the partial rat spleen cDNA clone (SEQ ID NO: 25 in the parent and SEQ ID NO: 6 herein) and the rat liver genomic clone (SEQ ID NO: 26 of the parent and SEQ ID NO: 5 herein) were missing an internal 177 bp EcoRI fragment that was part of each of these clones but lost in a subcloning step when the library inserts were removed from the λ vector with EcoRI digestion and ligated into a sequencing vector. The observation that the cDNA and genomic clones might be missing a coding fragment became apparent upon alignment of the rat genomic and cDNA sequences with various RT-PCR amplification products, including SEQ ID NO: 7, which revealed a gap in the rat sequence.

Subsequent isolation and sequence alignment of a cDNA from a spleen library using the spleen cDNA clone (SEQ ID NO: 6) as a probe provided a first indication that a portion of the spleen cDNA and genomic clones were not sequenced. Further confirmation of this idea became apparent upon amplification of an RT-PCR fragment, spanning domains 3 through 5, using a 5' primer (RRD3 5'Xho, containing a 5' XhoI restriction site to facilitate cloning) set out in SEQ ID NO: 14, and a 3' primer (RRD5 3'Hind, containing a HindIII site to facilitate cloning) set out in SEQ ID NO: 15.

GAACTCGAGGCCATGCCTCCACTTTCC (SEQ ID NO: 14)

CCATAAGCTTTATTCCACCGTGACAGCCAC (SEQ ID NO: 15)

Alignment of these two DNAs clearly revealed that the cDNA and genomic clones had lost a fragment prior to sequencing; this idea was further supported following sequencing of the RT-PCR DNA discussed infra. It was concluded that restriction digestion with EcoRI to remove the cDNA and genomic fragments prior to sequencing resulted in the excision of a 177 bp fragment that was not detected visually in the agarose gel separation of the clones from the λ phage sequences. Subsequent sequence analysis confirmed the location of two EcoRI sites flanking a 177 bp fragment in both of the original clones.

The 177 bp EcoRI fragment is situated between nucleotides 719 and 896 in the rat partial cDNA clone as set out in SEQ ID NO: 9 and between nucleotides 2812 and 2989 in the partial genomic clone as set out in SEQ ID NO: 8.

D. DNA Isolated by RT-PCR Clone

RT-PCR was utilized to generate more complete sequence information for the rat ICAM-related gene. Sequence information from the genomic clone (SEQ ID NO: 3) was used to design sense primers complementary to a region 5' of the protein coding region, as determined from the cDNA clone, and antisense primers designed complementary to coding sequences and regions 3' to the coding sequence in the cDNA clone (SBQ ID NO: 6).

Template cDNA for PCR reactions was prepared as follows. Approximately 2 µg of poly A+RNA isolated from rat spleen cells was denatured by heating at 65° C. in a 10 µl volume. Following denaturation, 0.1 µl RNasin (Invitrogen, San Diego, Calif.), 5 µl 5X RTase Buffer (BRL, Bethesda, Md.), 2 µl random hexamer (pd(N)6 at 100 µg/ml) (Pharmacia, Piscataway, N.J.), 6 µl dNTPs (2 mM each) and 2 µl AMV RTase (BRL) were added and the reaction was incubated at 42° C. for 60–90 min. Reactions were stored at −20° C. until needed.

An initial series of experiments was conducted to identify oligonucleotides primer pairs that produced an amplification product in PCR reactions using rat spleen cDNA as the template. Various 5' sense primers were paired in PCR with a 3' primer which was designed to be complementary to an internal, coding sequence; the 3' primer was designated RRD2 3-1 and is set forth in SEQ ID NO: 16.

AACGTGCGGAGCTGTCTG (SEQ ID NO: 16)

(In the ultimately isolated RT-PCR product, SEQ ID NO: 7, infra, primer RRD2 3-1 corresponded to nucleotides 719 through 736.) Similarly, various 3' antisense primers were paired with a 5' primer designed complementary to another internal, coding sequence; the 5' primer in these reactions was designated RGen3900S and is set forth in SEQ ID NO: 17.

ACGGAATTCGAAGCCATCAACGCCAGG (SEQ ID NO: 17)

(In SEQ ID NO: 7, infra, primer RGen3900S corresponded to nucleotides 1719 through 1736.) Based on the size of the amplification products and the ability of these products to hybridize with the partial cDNA clone, one pair of primers was determined to be most efficient and was used in subsequent PCR amplifications. The 5' primer was designated RGen780S (SEQ ID NO: 18) and the 3' primer was designated RGen4550AS (SEQ ID NO: 19).

CATGAATTCCGAATCTFGAGTGGGATG (SEQ ID NO: 18)

ATAGAATTCCTCGGGACACCTGTAGCC (SEQ ID NO: 19)

(In SEQ ID NO: 7, infra, primer RGen780S corresponded to nucleotides 1 through 18, and primer RGen4550AS corresponded to nucleotides 2197 through 2214.)

This primer pair was used in PCR under a variety of conditions to optimize amplification. A total of 15 different PCR buffers that varied in pH and Mg++ concentration were used at two different annealing temperatures, and a sample of the product from each reaction was separated on a 1% agarose gel. Because no amplification product could be detected by visual inspection of the ethidium bromide stained gel from any of the reaction conditions, more sensitive Southern hybridization was employed to detect the PCR products.

Aliquots of the amplified DNA were separated by electrophoresis, transferred to a Hybond N+ nylon membrane using conventional Southern blotting wicking techniques, and hybridized with the entire rat cDNA which was [$^{32}$P]-labeled. Hybridization conditions were essentially as described for the library screening procedure in Section A, supra. Autoradiography indicated that a small amount of DNA of approximately 2.2 kb had been generated in two of the reactions, and the remainder of the amplification product from the two reactions was separated on an agarose gel. The 2.2 kb region was eluted from the gel, even though no band was evident upon visual inspection, and used as a template in another PCR reaction using the same primers (SEQ ID NOs: 18 and 19), Tris-HCI buffer, pH 8.0, containing 1 mM Mg++, and 55° C. annealing temperature. The amplification product from the secondary PCR was visible in the gel and was eluted and cloned into a pBS+ plasmid (Stratagene, La Jolla, Calif.) for sequence analysis.

The resulting RT-PCR clone was determined to contain 2214 bp as set forth in SEQ ID NO: 7. The clone encoded domains 2 through 6 found in the rat spleen cDNA clone, an additional amino terminal domain 1, an additional carboxy terminal domain 7, and 164 bp of what appeared to be a further carboxy terminal domain 8. Immediately 5' to domain 1 was an additional 144 bp sequence presumed to have been derived from an intron between the leader and the first domain. This clone did not contain a 5' leader sequence or 3' transmembrane and cytoplasmic regions. In addition to the previously identified domain 6 in the spleen cDNA clone, the 7th and 8th domains in the RT-PCR clone supported the hypothesis that this clone was a novel rodent ICAM.

EXAMPLE 2

Northern Blot Analysis

In order to further investigate the possibility that the ICAM-related clones identified in Example 1 encoded a novel ICAM polypeptide as suggested by the unique Ig-like domains, tissue specific expression was examined by Northern blot analysis to permit comparison with the previously reported expression patterns of human ICAMs [ICAM-1, Dustin, et al., *J. Immunol.* 137:245–254 (1986); ICAM-2, Staunton, et al., *Nature* 339:61–64 (1989); ICAM-R, de FourgeroHes and Springer, *J. Exp. Med.* 175:185–190 (1992)].

Total cellular RNA from rat lung, brain, spinal cord, liver, digestive tract, thymus, lymph nedes, and spleen was prepared using STAT60 RNA isolation reagents (Tel-test "B", Inc, Friendswood, Tex.) according to the manufacturer's suggested protocol. Poly $A^+$ RNA was purified from total RNA using oligo dT cellulose columns. Approximately 5 µg of RNA derived from each tissue was separated on a 1% formaldehyde agarose gel, and transferred to hybond-C nitrocellulose membranes (Amersham).

A fragment of the rat spleen cDNA from Example 1 corresponding to domains 2 through 4 (nucleotides 1 through 724 in SEQ ID NO: 6) was subcloned into pBluescript $SK^+$ (Stratagene) and an antisense riboprobe was generated by in vitro transcription using $^{32}$P-labeled UTP and approximately 500 ng of linearized template according to a manufacturer's (Boehringer Mannheim, Indianapolis, Ind.) suggested protocol. The membrane-bound RNA was prehybridized in a solution containing 50% formamide, 5X SSC, 1X PE (50 mM Tris-HCl, pH 7.5, 0.1% sodium pyrophosphate, 0.2% polyvinylpyrrolidone, 0.2% ficoll, 5 mM EDTA, 1% SDS) and 150 µg/ml denatured salmon sperm DNA. The radiolabeled probe was denatured by boiling and added to the prehybridization solution to a final concentration of $1\times10^6$ cpm/ml. Hybridization was allowed to proceed for 16–18 hours at 65° C. The membranes were then washed at 65° C. in 2X SSC containing 0.1% SDS and subsequently exposed to X-ray film for 3–16 hours.

The Northern blot analysis indicated that the ICAM-related cDNA identified in Example 1 was expressed only in rat brain, a tissue specificity not previously reported for any other ICAM polypeptides. This expression pattern, in combination with the unique Ig-like domains not known to exist in other ICAM polypeptides, indicated that the ICAM-related clone was a novel member of the ICAM family of proteins, and was named ICAM-4.

The fact that the initially identified cDNA clones were detected in a rat spleen library suggested that a subset of cells in the spleen may express ICAM-4 at low levels. However, a properly spliced clone could not be detected in numerous hemopoietic cDNA libraries which led to doubt if ICAM-4 protein is actually expressed in tissue other than brain. One explanation for the detection of ICAM-4 cDNA in spleen is that the sensitivity of PCR may have amplified a trace amount of transcript even though these tissues do not express the encoded protein.

EXAMPLE 3

Isolation of Full Length Rat ICAM-4 cDNA

A. Identification of a Rat Brain cDNA Clone

In view of the tissue specific expression of ICAM-4, brain tissue mRNA was utilized in an attempt to isolate a full length cDNA encoding ICAM-4. Two probes, one complementary to domains 1 through 2 and a second complementary to domains 3 through 5 of the spleen cDNA clone identified in Example 1 (SEQ ID NO: 7), were radiolabeled and used to screen a rat brain cDNA library in λgt10 which was previously constructed in-house. Hybridization conditions were as described in Example 1, and positive plaques were subjected to one or more rounds of screening to obtain clonal phage.

Nine positive clones were identified, two of which hybridized to both probes. The longest of the two clones, designated clone 7, contained 2550 bp encoding four of the five Ig-like domains found in the probe cDNA. In addition, clone 7 encoded four other Ig-like domains not found in the probe. Putative transmembrane and cytoplasmic domains were identified which were followed by a stop codon, a polyadenylation signal, and a poly A tail. Clone 7 was lacking at least one 5' Ig-like domain as determined by comparison to the RT-PCR clone (SEQ 113 NO: 7), and also lacked a leader sequence; re-screening of the library did not yield any longer clones which contained these sequences. The nucleic acid sequence for clone 7 is set forth in SEQ ID NO: 10.

B. Determination of the 5' End

In order to isolate domain 1 and other 5' sequences, a PCR technique termed 5' Rapid Amplification of cDNA Ends (RACE) [PCR Protocols: A Guide to Methods and Applications, Innis, et al., (eds) Academic Press: New York (1990) pp:28–38] was employed using a 5' RACE kit (Clontech). This technique utilizes an internal primer paired with a second primer complementary to an adapter sequence ligated to the 5' end of cDNA library molecules. PCR with this primer pair will therefore amplify and facilitate identification of the intervening sequences. Overlapping sequence information can then be used to generate a complete sequence of the gene.

RACE-ready cDNA from rat brain (supplied with kit) was used in a PCR with the kit oligonucleotide and an antisense primer based on an internal ICAM-4 sequence. The 3' antisense primer, designated Spot714AS, was designed according to an ICAM-4 domain 4 sequence and is set forth in SEQ ID NO: 20.

CARGGTGACAAGGGCTCG (SEQ ID NO: 20)

The amplification product resulting from this primer pair was subsequently subjected to a secondary PCR using the same 5' kit primer paired with a 3' primer complementary to a region in ICAM-4 domain 1. The second 3' primer was designated RRACE2 and is set forth in SEQ ID NO: 21.

TATGAATTCAGTTGAGCCACAGCGAGC (SEQ ID NO: 21)

Each primer used in the secondary PCR contained an EcoR1 site to facilitate cloning of the resulting amplification products into $pBS^+$ (Stratagene). The resulting plasmid DNA which contained the 5' end of the gene was identified by hybridization to a rat ICAM-4 domains 1 and 2 probe, corresponding to nucleotides 1 through 736 in SEQ ID NO: 7. Partial sequence information for domain 1 and the hydrophobic leader was determined from the resulting amplification product.

The product from the 5' RACE method was a DNA fragment 222 bp long containing 60 bp upstream of the initiating methionine residue, an 82 bp leader sequence, and an 80 bp sequence from domain 1. The amplification product is set forth in SEQ ID NO: 11.

C. Full Length Sequence of Rat ICAM-4

A composite clone of the full length ICAM-4 was constructed from the sequence infonation derived from the 5' RACE method (SEQ ID NO: 11), the RT-PCR clone (SEQ ID NO: 7) and the brain cDNA clone 7 (SEQ ID NO: 10). The full length gene for rat ICAM-4 was determined to contain 2985 bp with a single open reading frame encoding a deduced 917 amino acid protein. A putative Kozak sequence is located upstream of the methionine residue in the leader sequence. A 27 amino acid hydrophobic leader sequence is followed by nine Ig-like domains, a transmembrane region and a 58 amino acid cytoplasmic tail. The composite ICAM-4 cDNA is set for in SEQ ID NO: 1, and the deduced amino acid sequence is set forth in SEQ ID NO: 2.

Like other ICAM polypeptides, ICAM-4 contains extracellular, transmembrane, and cytoplasmic domains. In the extracellular domain, the amino terminus of ICAM-4 is a leader sequence comprising amino acids 1 through 27 which is followed by nine immunoglobulin (Ig)-like domains, a characteristic unique to ICAM-4 in that ICAM-1, ICAM-2, and ICAM-R contain five, two, and five extracellular Ig-like domain, respectively. In ICAM-4, domain 1 comprises amino acids 28 through 118; domain 2 comprises amino acids 119 through 224; domain 3 comprises amino acids 225 through 321; domain 4 comprises amino acids 322 through 405; domain 5 comprises amino acids 406 through 488; domain 6 comprises amino acids 489 through 569; domain 7 comprises amino acids 570 through 662; domain 8 comprises amino acids 663 through 742; and domain 9 comprises amino acids 743 through 830. Within each domain, a characteristic "loop" structure is formed by a disulfide bond between cysteine residues located generally at opposite ends of the domain amino acid sequence. Other structural features of ICAM-4 include the transmembrane region comprising amino acids 831 through 859 and the cytoplasmic region comprising amino acids 860 through 917.

Comparison of amino acid sequence homology of each domain in rat ICAM-4 with the other members of the ICAM family was limited to the corresponding sequences of human ICAM-1, ICAM-2, and ICAM-R since sequence information for all three rodent homologs has not been previously reported. In the fast domain, the rodent ICAM-4 shows 21, 30, and 28 percent identity with human ICAM-1, ICAM-2, and ICAM-R, respectively. The second domain is more conserved, with the amino acid percent identities being 60, 42 and 62 with ICAM-1, -2, and -3, respectively. Domains 3–5 show percent identities of 48, 49, and 40 with ICAM-1 and 60, 59 and 29 respectively for ICAM-R. Interestingly, rat ICAM-4 domains 6 through 8 are most homologous with domain 5 (ranging from 29–42% identical), possibly arising from a gene segment duplication event. The ninth and final extracellular domain aligns poorly with other ICAM domains but has 22% identity with the 3rd and 6th domains of human VCAM-1, another member of the Ig family of protein which participate in cell adhesion. The cytoplasmic tail is 58 amino acids long. This is longer than the other members of the ICAM family wherein human ICAM-1, 2, and 3 contain 28, 26, and 37 amino acids,respectively. As with the ninth domain, rat ICAM-4 cytoplasmic tail is most homologous with the cytoplasmic tail of human VCAM-1, which contains only 19 amino acids. The membrane proximal 19 amino acids of rat ICAM-4 share 7 amino acid residues with VCAM-1 (37%).

Finally, functional binding to LFA-1 (CD11a/CD18) maps to the first domain in the ICAMs. Vonderheide et al.,[*J. Cell. Biol.*, 125:215–222 (1994)] identified a sequence motif purportedly involved in integrin binding. Despite the relatively low homology between rat ICAM-4 and other ICAMs in domain 1, this binding sequence motif is conserved, suggesting that rat ICAM-4 may be a ligand for LFA-1 and perhaps other integrins.

EXAMPLE 4

In Situ Hybridization in Brain Tissue

In order to localize the specific brain tissue which expressed ICAM-4, in situ hybridization with ICAM-4 domain 1 and ICAM-4 domains 3 through 4 anti-sense riboprobes was employed. The probes were labeled by in vitro transcription using $^{35}$S-labeled UTP.

Frozen tissue sections of normal rat brain were fixed in 4% paraformaldehyde for 20 minutes, rinsed and dehydrated, and the fixed RNA denatured for 2 minutes in 2X SSC, 70% formamide at 70° C. prior to hybridization. Tissue sections were hybridized overnight at 50° C. in a solution containing 50% formamide, 0.3M NaCl 20 mM Tris-HCl, pH 7.4, 5 mM EDTA, 10% dextran sulfate, 1X Denhardt, 0.5 mg/ml yeast RNA, 100 mM and a probe concentration of 50,000 cpm/μl. Slides were washed once in 4X SSC, 10 mM DTT at room temperature for 60 minutes, once in 50% formamide, 2X SSC, 10 mM DTT at 60° C. for 40 minutes, and once in each 2X SSC and 1X SSC for 30 minutes each at room temperature. Specificity of hybridization was determined in parallel experiments performed with the same protocol but also including a more stringent wash in 50% formamide, 1X SSC, 10 mM DTF at 60° C. for 40 minutes. After washing, the slides were dipped in NTB2 emulsion (Kodak, Rochester, N.Y.) and exposed from 2 to 21 days before being developed and counter-stained. Negative controls included sense probes generated from ICAM-4 domain 1 and ICAM-4 domain 3 through 4 sense riboprobes, in addition to a human immunedeficiency virus (HIV-1) riboprobe.

The signal detected in brain tissue was primarily localized in the gray matter with the strongest signal in the cerebral cortex and hippocampus. The hybridization profile was consistent with ICAM-4 expression primarily in cerebral neurons.

EXAMPLE 5

Generation of ICAM-4 Fusion Proteins

Rat ICAM-4/glutathione S-transferase (GST) fusion proteins were generated using the prokaryote expression vector pGEX (Pharmacia, Alameda, Calif.) in order to generate monoclonal antibodies against specific ICAM-4 polypeptide fragments.

PCR primers corresponding to the 5' and 3' ends of domain 1 and the 5' and 3' ends of domain 2 were used to amplify DNA fragments encoding the individual domains. The resulting fragments were separately cloned into an EcoRI site of pGEX-2T; DNA sequence analysis confirmed the correct orientation and reading frame. Transformants were subsequently screened for their ability to produce fusion protein of the appropriate molecular weight.

Both ICAM-4 domain 1/GST and ICAM-4 domain 2/GST fusion proteins remained in the insoluble fraction after the bacteria were lysed by sonjcation in PBS containing 1% SDS. The insoluble protein fraction from 100 ml cultures were boiled in SDS loading dye and separated on a 10% preparetire polyacrylamide-SDS gel. The gel was stained in ice cold 0.4M KCl and the fusion protein bands were excised. Fusion proteins were electroeluted from the gel slices in dialysis tubing in buffer containing 25 mM Tris-HCl and 192 mM glycine. Approximate protein concentration was determined by $OD_{280}$ and purity of the preparation was determined on SDS-PAGE stained with Coomasie blue.

EXAMPLE 6

Production of Monoclonal Antibodies Against Rat ICAM-4/GST Fusion Proteins

Balb/c mice were immunized by subcutaneous injection with 40–50 µg ICAM-4 domain-2/GST fusion protein (described in Example 5) emulsified in Freund's complete adjuvant (FCA). Two weeks later, the mice were again immunized by subcutaneous injection with the same protein, emulsified however in Freund's incomplete adjuvant. Two final intrapefitoneal immunizations given two weeks after the second immunization included soluble antigen with no adjuvant given at two week intervals. Serum from each immunized mouse was assayed by ELISA for its ability to specifically react with rat ICAM-4 produced by the baculovirus expression system described infra.

The spleen from mouse #1654 was sterilely removed and placed in 10 ml serum-free RPMI 1640. A single-cell suspension was formed by grinding the spleen tissue between frosted ends of two glass microscope slides submerged in serum free RPMI 1640 (Gibco, Buffington, Ottawa, Canada) supplemented with 2 mM L-glutamine, 1 mM sodium pyruvate, 100 units/ml penicillin, and 100 µg/ml streptomycin. The cell suspension was faltered through a sterile 70-mesh Nitex cell strainer (Beeton Dickinson, Parsippany, N.J.), and washed twice with RPMI followed by centrifuging at 200×g for 5 minutes. The resulting pellet from the final wash was resuspended in 20 ml serum-free RPMI. Thymocytes taken from three naive Balb/c mice were prepared in an identical manner.

Prior to fusion, NS-1 myeloma cells were maintained in log phase growth in RPMI with 11% Fetalclone serum (FBS) (Hyclone Laboratories, Logan, Utah) for three days. Once harvested, the cells were centrifuged at 200×g for 5 minutes, and the pellet was washed twice as described in the foregoing paragraph. After washing, the cell suspension was brought to a final volume of 10 ml in serum free RPMI. A 20 µl aliquot was removed and diluted 1:50 with serum free RPMI, and a 20 µl aliquot of this dilution was removed, mixed with 20 µl 0.4% trypan blue stain in 0.85% saline (Gibco), loaded onto a hemacytometer (Baxter Healthcare, Deerfield, Ill.) and the cells counted. Approximately $2.425 \times 10^8$ spleen cells were combined with $4.85 \times 10^7$ NS-1 cells, the mixture centrffuged and the supernatant removed. The resulting pellet was dislodged by tapping the tube and 2 ml of 50% PEG 1500 in 75 mM Hepes, pH 8.0, (Boehringer Mannheim, Indianapolis, Ind.) was added with stirring over the course of 1 minute. Subsequently, an additional 14 ml serum free RPMI was added over 7 minutes. The cell suspension was centrifuged at 200×g for 10 minutes and the supernatant discarded. The pellet was resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and 1.5×106 thymocytes/ml. The suspension was first placed in a 225 $cm^2$ flask (Corning, Essex, United Kingdom) at 37° C. for four hours before being dispensed into ten 96-well flat bottom tissue culture plates (Corning) at 200 µl/well. Cells in the plates were fed on days 3, 4, 5, and 6 post fusion by aspirating approximately 100 µl from each well with a 20 G needle (Becton Dickinson), and adding 100 µl/well plating medium described above except containing 10 units/ml IL-6 and lacking thymocytes.

The fusion plates were screened initially by antigen capture ELISA as follows. Immulon 4 plates (Dynatech, Cambridge, Mass.) were coated overnight at 4° C. with 100 ng/well of either domain 2-GST or domain 2-GST fusion protein in 50 mM carbonate buffer. The plates were blocked with 100 µl/well 0.5% fish skin gelatin (Sigma, St. Louis, Mo.) in PBS for 30 minutes at 37° C. After blocking, the plates were washed 3X with PBS containing 0.05% Tween 20 (PBST) and 50 µl/well of hybridoma supernatant from each fusion was added. After incubation at 37° C. for 30 minutes, the plates were washed as described above, and 50 µl of a 1:3500 dilution of horseradish peroxidase-conjugated goat anti-mouse IgG (Fc) (Jackson ImmunoResearch, West Grove, Pa.) was added. Plates were again incubated for 30 minutes and washed 4X with PBST. Substrate, 100 µl/well, consisting of 1 mg/ml o-phenylene diamine (Sigma) and 0.1 µl/ml 30% $H_2O_2$ in 100 mM citrate, pH 4.5, was added. The color reaction was allowed to proceed 10 minutes and quenched with the addition of 50 µl/well of 15% $H_2SO_4$. Absorbance at 490 nm was then determined on an automated plate reader (Dynatech).

Wells which were positive for domain 2-GST protein, but not for domain 1-GST protein, were then screened by ELISA against a Baculovirus supernatant (described infra). ELISA was performed as described above except that the Immulon 4 plates were initially coated overnight with Baculovirus supernatant diluted 1:4 in 50 mM carbonate buffer. Three wells (103A, 103B and 103F) were cloned two to three times, successively, by doubling dilution in RPMI, 15% FBS, 100 µM sodium hypoxanthine, 16 µM thymidine, and 10 units/ml IL-6. Wells of clone plates were scored visually after 4 days and the number of colonies in the least dense wells was recorded. Selected wells of each cloning were again assayed by ELISA after 7 to 10 days against either domain 1-GST protein and domain 2-GST protein, or Baculovirus supernatant.

The monoclonal antibodies produced by the hybridomas were isotyped by ELISA. Immulon 4 plates (Dynatech) were coated at 4° C. with 50 µl/well goat anti-mouse IgA, IgG, or IgM (Organon Teknika, Durham, NC) diluted 1:5000 in 50 mM carbonate buffer, pH 9.6. Wells were blocked for 30 minutes at 37° C. with 1% BSA in PBS, washed 3X with PBST. A 1:10 dilution of hybridoma culture supernatant (50 µl) was added to each plate, incubated, and washed as above. After removal of the last wash, 50 µl horseradish peroxidase-conjugated rabbit anti-mouse IgG1, $G_{2a}$, $G_{2b}$, or $G_3$ (Zymed, San Francisco, Calif.) (diluted 1:1000 in PBST with 1% normal goat serum) was added. Plates were incubated as above, washed 4X with PBST and 100 µl substrate, was added. The color reaction was quenched after 5 minutes with addition of 50 µl 15% $H_2SO_4$, and absorbance at 490 nm determined on a plate reader (Dynatech).

Results indicated that antibodies 103A, 103B, and 103F were all $IgG_1$ isotype. These antibodies were subsequently used in immunocytochemical analyses, Western blotting, and for purification of protein expressed in baculovirus.

EXAMPLE 7

Baculovirus Expression of Rat ICAM-4

A baculovirus expression system (Invitrogen) was used to generate soluble protein corresponding to domains 1 through 6 of ICAM-4. Because the leader sequence for ICAM-4 was not known at the time, the expression construct was made containing the coding sequence for ICAM-4 fused 3' to the ICAM-1 leader sequence in proper reading frame. Specific details regarding construction of the ICAM-1/ICAM-4 expression plasmid is as follows.

Rat ICAM-1 DNA encoding the five Ig-like domains was amplified by PCR using primers which incorporated several features to facilitate construction of the fusion plasmid. The 5' oligonucleotide primer included HindIII and BglII sites, in addition to a consensus Kozak sequence upstream of the first methionine in the leader sequence. The 3' oligonucleotide primer included a coding sequence for six histidines followed by a stop codon and a HindIII cloning site. The PCR amplification product was cloned into a HindIII-digested pBS+ vector and sequence analysis confirmed the appropriate construction. An internal SmaI site in the ICAM-1 leader sequence and another SmaI site in the vector's multiple cloning region (3' to ICAM-1 Ig-like domain 5) were digested which removed most of the ICAM-1 coding sequence. After these manipulations, the linearized, blunt-ended vector contained a portion of the upstream multiple cloning region (those restriction simms 5' of the original HindIII site in the multiple cloning region), the Kozak sequence and most of the ICAM-1 leader sequence.

The coding sequence for rat ICAM-4 domains 1 through 6 was amplified by PCR utilizing primers designed to permit cloning of this sequence into the linearized vector described above. The 5' oligonucleotide primer included an EcoRV site and the codons needed to complete the ICAM-1 leader sequence. The 3' oligonucleotide primer included codons for six histidine residues, a stop codon, and HindIII and EcoRV restriction sites. The amplification product from this PCR was digested with EcoRV to produce a blunt-ended sequence which was then ligated intlinearized -ended SmaI-digested pBS+ linearized vector. The entire sequence containing the ICAM-1 leader sequence 5' to the ICAM-4 domains 1 through 6 was removed from the construct with BglII and HindIII digestion and the purified ICAM-1/ICAM-4 fusion sequence cloned directly into a BglII/HindIII-digested pBluesac III vector (Invitrogen).

Protein production by the recombinant virus was assayed for by ELISA, initially using immune sera from mice immunized with rat ICAM-4 domain-2/GST fusion protein described in Example 5. In later work, monoclonal antibodies generated from those mice were used to purify ICAM-4 protein produced by the recombinant baculovirus in SF9 cells.

EXAMPLE 8

Production of Monoclonal Antibodies Against Baculovirus-Expressed Rat ICAM-4

Rat ICAM-4 domains 1-6 were expressed in the baculovirus expression system as described in Example 7. The recombinant protein was purified using monoclonal antibody 103A (as described in Example 6).

Briefly, 30 mg of purified monoclonal 103A (in 100 mM sodium borate, 500 mM sodium chloride) were coupled to three grams of Activated Cyanogen Bromide Sepharose 4B (Pharmacia, Piscataway, N.J.). Baculovirus supernatant containing recombinant rat ICAM-4 (domains 1-6) was loaded on the Sepharose column overnight at 4° C. The column was washed in calcium-magnesium-free phosphate buffered saline (CMF-PBS) and bound material was eluted in 50 mM citric acid, 500 mM NaCl pH 4.0. The sample was neutralized with 1/10 volume Tris pH 10 and stored at -20° C. The purified protein separated on SDS-PAGE appeared greater than 90% pure and migrated at approximately 80 kD.

Mice were immunized with the purified recombinant rat ICAM-4 domains 1-6 protein in a similar manner as described in Example 6. The spleen from mouse #1945 was used for fusion #127. The fusion protocol was as described in Example 6. The fusion wells were screened by FJISA on the recombinant ICAM-4 protein. The secondary screen included immunocytochemistry on rat brain sections (as below described in Example 9). Four additional antibodies specific for rat ICAM-4 were cloned out of this fusion: 127A, 127E, 127F and 1271-1. The immunocytochemical staining pattern of each antibody on rat brain sections was the same as observed with monoclonal antibody 103A (see Example 9). The monoclonal antibodies were tested for their ability to bind the D1/GST and D2/GST fusion proteins (described in Example 5). Monoclonal antibody 127A recognized the D1/GST fusion protein and 127H recognized the D2/GST fusion protein. These two distinct binding specificities along with the others that did not bind either GST protein suggest that at least 3 different epitopes were being recognized by the panel of antibodies. Hybridomas 127A and 127H were deposited May 31, 1995 and Jun. 1, 1995, respectively, with the American Type Culture Collection, 12301 Parklawn Drive, Rockville, Md. 20852, and assigned Accession Numbers HB11905 and HB11911, respectively.

EXAMPLE 9

Immunocytochemistry of Rat ICAM-4 Expression

Immunocytochemistry with monocional antibody 103A was performed to localize the protein production within the rat brain.

A brain was harvested from a normal adult female Lewis rat, sagittally sectioned, and washed in RNase-free 1X PBS on ice for 30 min. The brain sections were then placed in Tissue Tek H cryomolds (Miles Laboratories, Inc., Naperville, Ill.) with a small amount of O.C.T. compound (Miles, Inc., Elkhart, Ind.). The brains were centered in the cryomold, the cryomold filed with OCT compound, then placed in a container with 2-methylbutane (Aldrich Chemical Company, Inc., Milwaukee, Wisc.) and the container placed in liquid nitrogen. Once the tissue and OCT compound in the cryomold were frozen, the blocks were stored at -80° C. until sectioning.

The tissue was sectioned at 6 µm thickness, adhered to Vectabond (Vector Laboratories, Inc., Burlingame, Calif.) coated slides and allowed to air-dry at room temperature overnight until use. The sections were fixed in ethyl ether (Malinckrodt, Pads, Ky.) for 5 minutes at room temperature. Once the slides were removed from the ether, the reagent was allowed to evaporate. Each tissue section was blocked with 150 µl 50% Normal rat serum (Sigma) and 2% bovine serum albumin (BSA) (Sigma) in 1X PBS (made with sodium phosphates only) for 30 minutes at room temperature. After blocking, the solution was gently blotted from the sections and the purified superuatant antibody 103A (1.65 mg/ml) was diluted 1:10 in the blocking solution and 150 µl applied to each tissue section. The slides were placed in a humidity chamber and incubated at 4° C. overnight.

The next day the antibody solution was blotted gently from the section and the slides washed three times in 1X PBS for four minutes in each wash. The excess PBS was aspirated from the slide and 100 µl of the secondary, rat anti mouse-biotin conjugated antibody (Jackson ImmunoResearch Laboratories), diluted 1:100 in a solution of 10% normal rat serum and 2% BSA in 1X PBS, applied to the tissues. Incubation was allowed to proceed for one hour at room temperature. The sections were washed two times in 1X PBS for four minutes in each wash, then 100 μl of ABC reagent from an Elite Rat IgG Vectastain ABC kit (Vector Laboratories, Inc., Burlingame, Calif.), prepared according to the product insert, was applied to each section. Incubation was allowed to proceed for 30 minutes at room temperature. After incubation, the slides were washed two times in 1X PBS (four minutes each wash) and 150 μl of Vector VIP Peroxidase Substrate Solution (Vector Laboratories, Inc., Burlingame, Calif.) applied to each section for approximately ten minutes. After color development, the sections were rinsed under running tap water for five minutes, counterstained with Mayer's hematoxylin (Sigma) for 20 seconds, and rinsed again in gently running tap water for five minutes. The slides were dehydrated across a graded series of ethanols, passed through xylene and mounted with Accumount 60 (Stephens Scientific, Riverdale, N.J.).

Immunohistochemistry of rat brain sections strained with mAb 103A indicated that rat ICAM-4 is expressed in the neuronal cells of the hippocampus. Staining pattern suggested that the protein might be limited to the neuronal processes (dendrites). Brain sections stained in a similar manner with an irrelevant antibody or second step reagent alone do not show the distinct expression pattern seen with MAb 103A.

EXAMPLE 10

Cloning of a Human ICAM-4 Genomic DNA

During the cloning of rat ICAM-4 from genomic DNA, it was discovered that ICAM-4 and ICAM-1 were located within 5 kb of each other and this information was utilized in an attempt to clone the human homologue of ICAM-4.

Genome Systems Inc. (St. Louis, Mo.) amplified fragments in a human P1 library by PCR using human ICAM-1 domain 3 primers, a sense primer designed complementary to human ICAM-1 domain 3 (H-1/D3 S) and an antisense primer designed complementary to human ICAM-1 domain 3 (H-1/D3 AS). These primers are set forth in SEQ ID NOs: 22 and 23, respectively.

CCGGGTCCTAGAGGTGGACACGCA (SEQ ID NO: 22)

TGCAGTGTCTCCTGGCTCTGGTTC (SEQ ID NO: 23)

Two clones, designated 1566 and 1567, were identified and subjected to further analysis. Both P1 clones contained approximately 75–95 kb genomic DNA inserts. The clones were digested with BamH1, separated with agarose gel electrophoresis, and blotted onto nylon membranes. Southern blots hybridization were performed under either low stringency (30% formamide) or high stringchoy (60% formamide) at 42° C. with human ICAM-1, ICAM-3 or rat ICAM-4 radiolabeled probes; other constituents of the hybridization solution were as described in Example 1. The low stringency hybridization series was washed at room temperature in 2X SSPE containing 0.1% SDS. The high stringency hybridization was washed at 65° C. in 0.2X SSPE containing 0.1% SDS. The washed membranes were exposed to X-ray film for 3.5 hours.

The differential hybridization indicated that human ICAM-1 was contained on a 5.5 kb Barnill fragment while human ICAM-3 was located on a 4.0 kb and a 1.5 kb Barnill fragment. The human ICAM-1 and ICAM-R fragments were subcloned into pBS+ and their identity confirmed by limited sequence analysis.

A 7.0 kb BamH1 fragment that hybridized with rat ICAM-4 under high stringency conditions was subcloned and further fragmented with RsaI restriction digestion. Three RsaI fragments that hybridized with rat ICAM-4 were identified and their sequences determined. Based on homology to rat ICAM-4, these fragments appeared to contain domains 2, 3, 4, 5 and part of domain 6.

EXAMPLE 11

Cloning of a Human ICAM-4 cDNA

The fragments of genomic DNA corresponding to domains 2–5 of human ICAM-4 (described in Example 10) were used as probes to screen a λgt10 Human hippocampus cDNA library (Clontech, Palo Alto, Calif.). The library screening protocol was essentially as described in Example 1.

The longest human ICAM-4 clone (#18) that was found in that library was only 992 bp (SEQ ID: 24) and corresponded to roughly the middle of the predicted 3 kb gene. The 992 bp DNA insert from clone 18 (SEQ ID: 24) was used as a probe to screen a λZAPII human hippocampus cDNA library (Stratagene, La Jolla, Calif.). This library yielded a number of positive clones. The longest clone, #34, was 2775 bp (SEQ ID: 25). Based on alignments to the full length rat ICAM-4, it was predicted that this clone was missing the leader sequence and approximately 30 bp at the 5' end of domain 1. The poly $A^+$ tail at the 3' end was missing, but the translation stop codon was present.

A fragment of DNA corresponding to the first 3 domains (nucleotides 1 to 840 in clone #34) was used as a probe to screen a λgt10 cDNA library derived from human cerebral cortex (Clontech, Palo Alto, Calif.). One clone, 16-1 (SEQ ID: 26), was identified as having 1557 bp, and included 39 bp of 5' untranslated DNA, a leader sequence and sequence information through the fifth domain. Overlapping clones #34 (SEQ ID: 25) and 16-1 (SEQ ID: 26) were used to generate a composite of the full length human ICAM-4 sequence (SEQ ID: 27).

The full length gene is 2927 bp long and encodes a 924 amino acid protein. The ICAM-4 nucleotide sequence is set out in SEQ ID NO: 27 and the amino acid sequence is set out in SEQ ID NO: 28. Sequence alignment with the full length rat ICAM-4 gene (SEQ ID: 11) revealed an overall DNA sequence identity of 82% and 85% identity at the amino acid level. The apparent 9 Ig like extracellular domain structure of the protein is conserved between rat and human. The leader sequence extends from amino acid 1 to 28; domain 1 from amino acid 29 to 117; domain 2 from amino acid 118 to 224; domain 3 from amino acid 225 to 320; domain 4 from amino acid 321 to 405; domain 5 from amino acid 406 to 488; donlain 6 from amino acid 489 to 570; domain 7 from amino acid 571 to 663; domain 8 from amino acid 664 to 743; domain 9 from amino acid 744 to 837; the transmembrane region from amino acid 838 to 857 and the cytoplasmic tail from amino acid 858 to 924.

Human ICAM-4 (HuICAM-4), in addition to being genetically linked to ICAM-1 and ICAM-R, also showed certain common structural features that group them together as a family of molecules. A domain by domain alignment of HuICAM-4 with the other members of the ICAM family shows varying degrees of homology. Domain 1 amino acid sequence of HuICAM-4 is 21, 30 and 26% identical to domain 1 of ICAMs 1, 2 and 3 respectively. Domain 2 of HuICAM-4 is 61, 39 and 62% identical to ICAMs 1, 2 and 3 respectively. Domain 3 of HuICAM-4 is 50 and 65% identical to ICAMs 1 and 3 respectively. Domain 4 of HuICAM-4 is 54 and 64% identical to ICAMs 1 and 3 respectively. Domains 5–8 of HuICAM-4 are most homologous to the fifth domains of ICAM-1 and 3, with percent identities ranging from 33–47 for ICAM-1 domain 5 and 21–31 for ICAM-R domain 5. The ninth domain of HuICAM-4 aligns poorly with the other members of the ICAM family but is homologous to domains 3 (24% identical) and 6 (23% identical) of HuICAM-1.

EXAMPLE 12

Northern Analysis of Human ICAM-4 Expression

Two human multiple tissue Northern (MTN) blots were purchased from Clontech (Palo Alto, Calif.). These contained at least 2 µg of poly A⁺RNA from 16 different human tissues (as shown in Table 1) run on a denaturing formaldehyde 1.2% agarose gel and transferred to nylon membrane. The blots were prehybridized for three hours at 42° C. in 10 ml of a solution containing 5X SSPE, 10X Denhardts solution, 50% formamide, 2% SDS and 100 µg/ml denatured salmon sperm DNA. The blots were hybridized in the above solution with a radiolabeled human ICAM-4 probe (clone #18, SEQ ID: 24) for 16 hours at 42° C. The following day, the blots were washed in a solution of 0.1X SSC/0.1% SDS at room temperature followed by a wash at 50° C. The blots were exposed to x-ray film at –80° C. for 24 hours. Results of the analysis are shown below in Table 1.

Only the lane containing RNA from the brain hybridized to the ICAM-4 probe, giving a single band at approximately 3 kb. Longer exposure (five days) confumed that only the brain had a detectable level of message. In order to determine if all lanes contained comparable mounts of RNA of comparable quality, the same blot was hybridized with a control β-actin probe. Blots were stripped of the ICAM-4 probe by treatment with a boiling solution of 0.1% SDS for 15 minutes, and subsequently probed in a similar manner with a β actin probe provided by the manufacturer. Except for minor variation in mounts, all lanes were shown to have good quality RNA.

TABLE 1

Northern Tissue Analysis of Human ICAM-4 Expression

| Tissue | PROBE | |
|---|---|---|
| | ICAM-4 | β-Actin |
| Heart | – | +++ |
| Brain | + | ++ |
| Placenta | – | +++ |
| Lung | – | +++ |
| Liver | – | +++ |
| Skeletal muscle | – | ++++ |
| Kidney | – | +++ |
| Pancreas | – | ++ |
| Spleen | – | +++ |
| Thymus | – | +++ |
| Prostate | – | +++ |
| Testis | – | +++ |
| Ovary | – | +++ |
| Small intestine | – | +++ |
| Colon | – | +++ |
| Peripheral blood leukocyte | – | +++ |

Two additional Northern blots were purchased from Clontech that contained poly A⁺ RNA from 16 different subregions of human brain (as shown in Table 2). Blots were probed in a manner similar to that used for tissue analysis and results are shown in Table 2. RNA quality and qttantity loaded was checked by probing the blots with a β actin probe.

All of the regions that showed ICAM-4 expression are part of the telencephalon, with the exception of the thalamus which is considered part of the diencephalon. The hippocampus and cerebral cortex appeared to have the highest level of expression. The transcript size in all cases was the same, 3 kb. The exquisite tissue distribution of the ICAM-4 expression suggests that the promoter region may contain elements that coffer the observed developmental and spatial expression of the gene product. The utility of such information may provide insight into the understanding of control of neural gene expression in general.

TBLE 2

Northern Brain Cell Type Analysis of Human ICAM-4 Expression

| Tissue | PROBE | |
|---|---|---|
| | ICAM-4 | β-Actin |
| Amygdala | ++ | +++ |
| Caudate nucleus | ++ | +++ |
| *Corpus callosum* | + | +++ |
| Hippocampus | ++ | +++ |
| Hypothalamus | – | +++ |
| *Substantia nigra* | – | +++ |
| Subthalamic nucleus | + | +++ |
| Thalamus | + | +++ |
| Cerebellum | – | +++ |
| Cerebral cortex | +++ | +++ |
| Medulla | – | +++ |
| Spinal cord | – | +++ |
| Occipital pole | ++ | +++ |
| Frontal lobe | ++ | +++ |
| Temporal lobe | ++ | +++ |
| Putamen | ++ | +++ |

EXAMPLE 13

Generation of Human ICAM-4/IgG Fusion Proteins

Human ICAM-4/IgG1 fusion proteins expression plasmids were constructed to produce proteins for generating monoclonal antibodies and for use in adhesion assays to identify potential ICAM-4 ligands. Two constructs were made; the first included DNA encoding domains 1–3 of HuICAM-4 and the second, domains 4–8. Both were linked to the Fc region of human IgG1 in vector pDCS 1 that uses the cytomegalovirus (CMV) promoter to drive expression and the signal sequence from IgG4 to facilitate secretion of the molecules.

PCR primers (shown below as SEQ ID NOs: 29–32) were designed to generate the necessary DNA fragments for sub-cloning. The "sense" primer for the 5' end of domain 1 (HI4-D1(s), SEQ ID NO: 29) was designed to fill in 30 base pairs of domain 1 missing in clone #34. Primers HI4-D1(S) (SEQ ID NO: 29) and HI4-D3(AS) (SEQ ID NO: 30) were used to generate a DNA fragment encoding domains 1–3 of human ICAM-4, corresponding to a region in SEQ ID NO: 1 from nucleotide 130 to nucleotide 996. Primers HI4-D3(S) (SEQ ID NO: 31) and HI4-D8(AS) (SEQ ID NO: 32) were used to generate a DNA fragment encoding domains 4–8 of human ICAM-4, corresponding to a region in SEQ ID NO: 30 from nucleotide 997 to nucleotide 2268. Each 5' primer encoded a BamHI restriction site (GGATCC, indicated in bold below) and each 3' (antisense) primer contained a XhoI site (CTCGAG, indicated in bold below) to facilitate subcloning 5' to the IgG1 gene. All oligonucleotides contain spacer nucleotides (underlined, below) at the 5' end to permit restriction digestion.

| | |
|---|---|
| HI4-D1(S) | (SEQ ID NO: 29) |
| GTACTTACAGGATCCGCGGTCTCGCAG-GAGCCCTTCTGGGCGGACCTACAGCCTGCGTGGCGTTC | |
| HI4-D3(AS) | (SEQ ID NO: 30) |
| ATTTCTCTCGAGGATGGTCACGTTCTCCCGG | |
| HIR-D4(S) | (SEQ ID NO: 31) |
| ATTTCTGGATCCTACAGCTTCCCGGCACCACTC | |
| HI4-D8(AS) | (SEQ ID NO: 32) |
| ATTTCTCTCGAGTTCCACGCCCACAGTGACGG | |

PCR reactions were carried out in a 50 µl volume using buffers supplied by Perkin Elmer with the AmpliTaq enzyme. Primers were added at a final concentration of 10 µg/ml and all four dNTPs were included at 2 mM. The reactions were continued through 30 cycles of denaturation (94° C. for four minutes), annealing (50° C. for two minutes) and extension (72° C. for one minute). PCR products were visualized on agarose gels and an aliquot of each reaction was used to subclone the PCR products into vector pCRII (Invitrogen, SanDiego, Calif.). Sequence analysis was performed to detect possible errors resulting from the amplification process and to confirm proper orientation. Appropriate clones were digested with BamHI and XhoI and fragments separated with agarose gel electrophoresis. Purified fragments were ligated into a pDCS1 vector previously digested with BamHI and XhoI and the resulting plasmids were sequenced to confirm proper orientation and reading frame.

Human ICAM-4 domains 1–3 and 4–8/IgG1 fusion proteins were obtained following transient transfection of the expression plasmids into COS7 cells and isolation of the secreted protein from the culture media. Transfection was carried out as follows. Adherent COS7 cells at approximately 50–60% confluence were washed with CMF-PBS and subsequently contacted with 10–15 µg of plasmid DNA in 7.5 ml serum-free DMEM media (Gibco, Gaithersburg, Md.) containing 6 µl of 0.25M chloroquine (Sigma, St. Louis, Mo.). An additional 7.5 ml of serum-free media containing 150 µl of DEAE dextran (50 mg/ml) (Sigma, St. Louis, Mo.) were added and the plates incubated 2–3 hours before the media was removed and replaced with 10% DMSO (Mallinckrodt, McGaw Park, Ill.) in PBS. After a one minute incubation, the DMSO solution was removed and replaced with fresh media containing 5% FBS. Each transfection included multiple plates, and media from cells expressing the same protein were pooled for protein isolation.

Media were collected every three days over the course of 3–4 harvests. Proteins were purified using a 0.4–0.8 ml Procep A column (Bioprocessing Ltd, England) pre-equilibrated with 35 mM Tris, 150 mM NaCl, pH 7.5. Culture media was loaded onto the column two times at a flow rate of less than 60 column volumes per hour. The column was washed one time with each of 20 column volumes of Tris/NaCl buffer, 20 column volumes of 0.55M diethanolamine, pH 8.5, and 20 column volumes of 50 mM citric acid, pH 5.0. The fusion proteins were eluted into one ml fractions using 50 mM citric acid pH 3.0 and each fraction was neutralized with $\frac{1}{10}$ volume 1M Tris, pH 9.5. Protein concentration was determined by $OD_{280}$, and purity was determined using SDS-PAGE.

A significant contamination from bovine IgG (present in the FBS) was noted. Even though the domains 1–3 fusion protein was predicted to be smaller than the domains 4–8 fusion protein, both migrated at approximately 90 kD. One possible explanation for the observation is that the smaller domains 1–3 fusion protein may be more heavily glycosylated than the larger domains 4–8 fusion protein.

In addition to use of the purified proteins for monoclonal antibody production, described below, the proteins will also be used in adhesion assays to identify ICAM-4 ligands.

EXAMPLE 14

Monoclonal Antibody Production

The purified protein described in Example 13 was utilized to generate monoclonal antibodies using an immunization protocol as described in Example 6.

The spleen from mouse #2250 (immunized with HuICAM-4 D1-3/IgG1) was used for fusion 172 and the spleen from mouse #2272 (immunized with HuICAM-4 D4–8/IgG1) was used for fusion 173. The fusion protocol utiliized was as described in Example 6. Fusion plates were screened by ELISA (essentially as described in Example 6) using each HuICAM-4/IgG1 fusion protein. Fusion well supernatants that recognized the immunogen protein, and no other, were considered for cloning. Immunocytochemistry on human hippocampus sections was used as a secondary screen.

One primary clone from each fusion was positive by immunocytochemistry and was cloned. One of the two clones failed to grow upon cloning, leaving only one candidate to pursue, clone 173E which was derived from the HuICAM-4 D4–8/IgG1 immunized mouse. Hybridoma 173E was deposited Jun. 1, 1995 with the American Type Culture Collection, 12301 Parklawn Drive, Rockville, Md. 20852, and assigned Accession Number HB11912.

Additional fusions are similarly performed to generate other antibodies specifically immunoreactive with particular ICAM-4 fragments.

---

What is claimed is:

1. A purified and isolated polynucleotide comprising the ICAM-4 protein coding sequence set out in SEQ ID NO: 27 from nucleotide 40 to nucleotide 2811.

2. A purified and isolated polynucleotide encoding the ICAM-4 amino acid sequence set out in SEQ ID NO: 28.

3. The polynucleotide of claim 2 which is a DNA molecule.

4. A DNA expression construct comprising a DNA molecule according to claim 3.

5. A host cell transformed with a DNA molecule according to claim 3.

6. A method for producing an ICAM-4 polypeptide comprising growing a host cell according to claim 5 in a suitable medium, isolating ICAM-4 polypeptide from said host cell or the medium of its growth, and recovering said ICAM-4 polypeptide.

7. The DNA molecule of claim 3 which is a cDNA molecule.

8. The DNA molecule of claim 3 which is a genomic DNA molecule.

9. The DNA molecule of claim 3 which is a wholly or partially chemically synthesized DNA molecule.

10. An anti-sense polynucleotide which hybridizes to the polynucleotide of claim 2 under hybridization conditions of 5X SSPE, 10X Denhardts solution, 50% formamide, 2% SDS, and 100 µg/ml denatured salmon sperm DNA at 42° C. for 16 hours and washing conditions of 0.1X SSC and 0.1% SDS at 50° C.

* * * * *

UNITED STATES PATENT AND TRADEMARK OFFICE
CERTIFICATE OF CORRECTION

Page 1 of 3

PATENT NO. : 5,702,917
DATED : December 30, 1997
INVENTOR(S) : Kilgannon et al.

It is certified that error appears in the above-identified patent and that said Letters Patent is hereby corrected as shown below:

Col. 5, line 9: After "...Binding proteins," please insert - -are- -.

Col. 9, line 57: Please delete "SBQ", and insert - -SEQ- -.

Col. 10, line 26: Please delete "CATGAATTCCGAATCTFGAGTGGGATG", and insert - - CATGAATTCCGAATCTTGAGTGGGATG- -.

Col. 11, line 20: Please delete "Fourgerohes", and insert - -Fourgerolles- -.

Col. 12, line 26: Please delete "113", and insert - -ID--.

Col. 14, line 5: Please delete "hornology", and insert - -homology- -.

Col. 14, line 27: Please delete "DTr", and insert - -DTT- -.

Col. 14, line 28: Please delete DTr", and insert - -DTT- -.

Col. 14, line 33: Please delete "DTF", and insert - -DTT- -.

Col. 14, line 66: Please delete "sonjcation", and insert - -sonication- -.

Col. 15, line 20: Please delete "intrapefitoneal", and insert - -intraperitoneal- -.

Col. 15, line 30: Please delete "Buffington", and insert - -Burlington- -.

Col 15, line 33: Please delete "faltered", and insert - -filtered- -.

UNITED STATES PATENT AND TRADEMARK OFFICE
CERTIFICATE OF CORRECTION

PATENT NO. : 5,702,917

DATED : December 30, 1997

INVENTOR(S) : Kilgannon et al.

It is certified that error appears in the above-identified patent and that said Letters Patent is hereby corrected as shown below:

Col. 15, line 34: Please delete "Beeton", and insert --Becton--.

Col. 15, line 53: Please delete "centrffuged", and insert --centrifuged--.

Col. 15, line 63: Please delete "1.5x106", and insert --$1.5 \times 10^6$--.

Col. 17, line 24: Please delete "Simms", and insert --sites--.

Col. 17, line 37: Please delete "intlinearized", and insert --into the blunt--.

Col. 17, line 39: Please delete "BgIII", and insert --BglII--.

Col. 17, line 42: Please delete "BgIII", and insert --BglII--.

Col. 17, lines 56 & 57 please delete "baculovims", and insert -- baculovirus--.

Col. 18, line 9: Please delete "FJISA", and insert --ELISA--.

Col. 18, line 14: Please delete "1271-1", and insert --127H--.

Col. 18, line 60: Please delete superuatant", and insert --supernatant--.

Col. 19, line 66: Please delete "Barnill", and insert --BamH1--.

Col. 19, line 67: Please delete "Barnill", and insert --BamH1--.

Col. 20, line 9: Please delete "hornology", and insert --homology--.

UNITED STATES PATENT AND TRADEMARK OFFICE
CERTIFICATE OF CORRECTION

PATENT NO.   :   5,702,917
DATED        :   December 30, 1997
INVENTOR(S)  :   Kilgannon et al.

It is certified that error appears in the above-identified patent and that said Letters Patent is hereby corrected as shown below:

Col. 20, line 26: Please delete "hIppocampus", and insert - -hippocampus- -.

Col. 21, line 36: Please delete "mounts", and insert - -amounts- -.

Col. 21, line 42: Please delete "mounts", and insert - -amounts- -.

Col. 22, line 23, Table 2: Please delete "Tissue", and insert - -Brain Region- -.

Col. 23, line 11: Please delete "HIR", and insert - -HI4- -.

Signed and Sealed this

Fourteenth Day of November, 2000

Attest:

Q. TODD DICKINSON

Attesting Officer

Director of Patents and Trademarks